United States Patent [19]

Wickiser

[11] Patent Number: 5,340,804
[45] Date of Patent: Aug. 23, 1994

[54] 1,5-DIPHENYL-3-FORMAZANCARBONI-TRIL PARASITICIDES

[75] Inventor: David I. Wickiser, Indianapolis, Ind.
[73] Assignee: Eli Lilly and Company, Indianapolis, Ind.
[21] Appl. No.: 961,605
[22] Filed: Oct. 15, 1992

Related U.S. Application Data

[63] Continuation-in-part of Ser. No. 792,111, Nov. 14, 1991, abandoned.
[51] Int. Cl.$^5$ .................. C07C 245/04; C07C 245/06; A01N 33/12; A01N 33/26
[52] U.S. Cl. ...................................... 514/150; 534/652
[58] Field of Search .......................... 534/652; 514/150

[56] References Cited

U.S. PATENT DOCUMENTS

| | | | |
|---|---|---|---|
| 3,910,877 | 10/1975 | Prichard et al. | 260/193 |
| 4,069,320 | 1/1978 | Prichard et al. | 424/226 |
| 4,753,890 | 6/1988 | Smith-Lewis et al. | 436/74 |

FOREIGN PATENT DOCUMENTS

| | | | |
|---|---|---|---|
| 2339743 | 2/1974 | Fed. Rep. of Germany | 534/652 |
| 3418852 | 11/1985 | Fed. Rep. of Germany | 548/254 |

OTHER PUBLICATIONS

Bulkina, Z. P. et al., Fiziol. Aktiv. Veschestva, No. 2, pp. 91–98, 1969, and translation thereof.
CA 73 12657q (1970) (Bulkina et al).
CA 105(1): 3077c (Stellmach et al II). (1993).
Darwazeh et al. Proceedings & Papers of the 49th Annual Conference of the California Mosquito & Vector Control Assn., Inc., Apr. 26–29, 1981, Reading, Calif., pp. 73–75. Activity of New Larvicides Against Mosquitoes.
Nineham et al. Chem. Reviews, vol. 55, pp. 355–483 (1955).
Dubenko et al. J. Org. Chem. USSR, vol. 2, pp. 710–712 (1966). Investigation in the arylhydrazone series–derivatives of glyoxylic acid.
Dubenko et al. J. Org. Chem. USSR, vol. 6, pp. 1103–1106 (1970) Halochromism of 3-substituted 1,5-diarylformazans.

*Primary Examiner*—Floyd D. Higel
*Attorney, Agent, or Firm*—Kathleen R. S. Page

[57] ABSTRACT

The present invention is directed to the use of 1,5-diaryl-3-formazancarbonitrile compounds for the control of parasites in vertebrate animals.

49 Claims, No Drawings

1,5-DIPHENYL-3-FORMAZANCARBONITRIL PARASITICIDES

CROSS REFERENCE TO RELATED APPLICATION

This is a continuation-in-part of my copending application Ser. No. 07/792,111, filed Nov. 14, 1991, and abandoned after present application was filed.

BACKGROUND OF THE INVENTION

By definition, a parasite is an organism which lives on, and typically at the expense of, another organism called the "host." Parasitic organisms are found in many different phyla of the animal world, and hosts are similarly found in many different phyla of the animal world. The greatest number of parasites are members of the phyla Platyhelminthes, the Classes Trematoda and Cestoidea;

Nematoda; and

Arthropoda, the Classes Arachnida and Insecta.

The Platyhelminthes and Nematoda are informally referred to as "helminths." These species typically live in the intestinal tract, or in some cases other internal organs, of the host; these species are often called "endoparasites." The arthropod parasites are often called "ectoparasites" because they typically attack the host on its external ("ecto") surface. Agents which control both internal and external parasites are sometimes referred to as "endectocides."

The hosts are typically vertebrates. Human beings are of course potential hosts for many parasites, and in tropical areas and in areas with minimal sanitation, parasitic infections are a regular part of medical practice. Also highly subject to attack by parasites are the numerous livestock animals such as cattle, sheep, pigs, goats, chickens, turkeys, ducks, geese, and the like. Likewise, horses are subject to parasitic attack, as are mink and other animals grown for their fur; and rats, mice and other animals used in laboratory and research settings. Companion animals such as dogs and cats are highly subject to attack by parasites, and because of their close relationship with humans, such parasitism poses problems for the humans with whom they are associated. Fish and other animals grown in aquaculture are also subject to parasitic attack. In short, parasitism involves essentially the whole range of vertebrate animals. Further, parasitic organisms have evolved many quite specific modes of interaction with their hosts, which makes them relatively inaccessible to control. Many of them live internally within the host; and in this and other ways, they have ingeniously avoided control.

The economic toll from parasite infestation is staggering. In the livestock realm, animals suffer reduced feed efficiency and growth rates. Milk and wool production suffer; and there is damage to fleece, hides, and pelts. Animals are rendered susceptible to secondary microbiological infections and to further parasite attack. Not infrequently, parasite attack is fatal. It also causes discomfort even when it is not severely detrimental to the host. Although a number of parasiticides are in use, they suffer from a variety of problems, including a limited spectrum of activity, the need for repeated treatment, and, in many instances, resistance by parasites. Therefore, there is a critical need for new parasiticides.

The present invention provides a new tool in the control of parasitic organisms, especially those "hematophagous" organisms which attack their hosts by ingesting blood. By "ingesting" is meant not only those parasites which pierce and suck the blood from a circulatory system, but also those parasites, typically arthropods, which consume tissue of the host and thereby inevitably consume blood. This new tool is a class of compounds known as formazans. Many of the compounds are old, see U.S. Pat. No. 4,069,320. This patent describes the subject compounds as useful in controlling insects, and as noted above, there are parasitic organisms among the insects. However, the teaching of U.S. Pat. No. 4,069,320 is that insects can be controlled by contact, a technique which, however successful, is inherently impractical or impossible as a tool to control blood-ingesting parasitic organisms. Only a method of achieving systemic control via the circulatory system of the host can provide truly effective control of blood-ingesting parasitic organisms, and there is nothing in U.S. Pat. No. 4,069,320, which suggests or teaches any way of providing such systemic control. Thus, the present discovery unexpectedly provides a new tool in the control of parasitic organisms.

BRIEF SUMMARY OF THE INVENTION

The present invention is directed to the prevention of parasitic attack on host animals.

In more detail, the present invention is directed primarily to a method for protecting a vertebrate animal against a blood-ingesting parasite which comprises administering to the animal an effective amount of an active agent which is a compound of the formula:

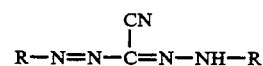

wherein each R independently represents a moiety of the formula:

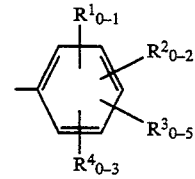

wherein
$R^1$ is cyano;
$R^2$ is nitro;
$R^3$ is bromo, chloro, or fluoro;
$R^4$ is iodo or a group of the formula $-R^5{}_n R^6$ wherein n represents 0 or 1, $R^5$ represents
—O—,
—S—,
—SO—,
—SO$_2$, or
—OSO$_2$—, and
$R^6$ represents
—CF$_3$,
—CF$_2$CF$_2$H,
—CH$_2$CF$_3$, or
—C$_2$F$_5$;

with the following limitations:
(1) at least one R bears at least one substituent,
(2) when an R contains one or more $R^1$, $R^2$, or $R^4$ substituents, the total number of substituents on that R is not more than 3; or a physiologically acceptable salt thereof.

Although the primary method of the present invention, set forth above, is that of protecting a vertebrate against blood-ingesting parasites, other methods are also included within the scope of the present invention. One other method is that of administering to a vertebrate animal an effective amount of the same active agent as above defined, to protect against attack by non-blood-ingesting intestinal parasites. These are parasites which live in the intestinal tract, with or without attachment, and ingest the contents of the intestinal tract. Examples include Trichostrongylus, Nematodirus, and tapeworm. The present compounds are also useful in a yet other method, in which the same active agent as above defined, is employed as a "feed through larvicide." In this method, the compound is administered to a vertebrate animal, especially a warm blooded animal, in order to inhibit parasitic organisms which live in the feces of the animal. Such organisms are typically insect species in the egg or larval stage.

The present invention is also directed to methods employing, and compositions comprising, the combination of (1) a compound of Formula I and (2) a known parasiticide. Preferred known parasiticides for such combinations are the following:
  albendazole,
  fenbendazole,
  flubendazole,
  mebendazole,
  oxfendazole,
  oxibendazole,
  ricobendazole,
  thiabendazole, and
  triclabendazole;
and the following:
  levamisole,
  morantel,
  pyrantel, and
  piperazine,
or a physiologically acceptable salt of this latter group. Such compositions allow enhanced control of parasites.

In addition to the foregoing novel methods, the present invention is directed to certain novel compounds. These are (1) the compounds of Formula I wherein at least one of R bears an —$R^5_nR^6$ substituent wherein n is 1 and $R^5$ is —$OSO_2$—; (2) the quaternary ammonium salts of all of the compounds defined by Formula I, wherein the salt moiety is of the formula

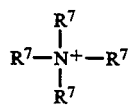

wherein each $R^7$ is independently selected from the group consisting of alkyl of from 1 to 20 carbon atoms, with the total number of carbon atoms in all of the $R^7$ groups being from 4 to 40; and (3) the salts of the compounds defined by Formula I with a known basic parasiticidal compound selected from the group consisting of
  levamisole,
  morantel,
  pyrantel, and
  piperazine.

Yet other embodiments will be apparent from the following detailed description of the invention.

DETAILED DESCRIPTION OF THE INVENTION

The compounds to be employed in the present invention are defined throughout by the following formula:

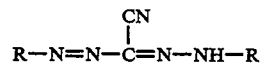

However, as noted in U.S. Pat. No. 4,069,320, the compounds exist as tautomers of the above and two other forms:

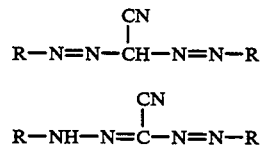

For consistency, the first of these three is used throughout, but it is to be understood that it designates any of the forms or a mixture of any of them. Cis and trans or syn and anti isomers are also possible and are also included in the single formula used throughout.

The compounds are prepared by known techniques, which are well described in U.S. Pat. No. 4,069,320, which is incorporated herein by reference. There is also a general review article on formazans: *Chem. Reviews,* 55, 355–483 (1955). For the convenience of the reader, the principal synthetic technique is summarized below.

An aniline of the formula $R\text{-}NH_2$ is diazotized by reacting it with a nitrosating agent in a strongly acidic medium at a temperature of from −20° to 100° C., typically 0°–40° C.

The resulting diazonium salt

wherein X is $Cl^-$, $HSO^-_4$, $H_2PO^-_4$ or other counter ion from the acid, is then coupled with an active methylene compound of the formula

in an aqueous media at temperatures of from −20° to 100° C., and preferably at temperatures of 0° to 40° C.

The reaction initially yields a hydrazone intermediate:

which can be isolated at pH of preferably 4–6. However, when a symmetrical compound is desired, one mole of the active methylene compound is employed per two moles of diazonium salt, and the final product can be obtained and isolated directly at pH of 4 to 12. When an asymmetrical compound is desired, equimolar amounts of a first diazonium salt and active methylene compound are used, and the hydrazone intermediate, with or without isolation, is reacted with a different diazonium salt.

Salts are prepared in standard procedures. Typically the formazan is reacted with a metal or ammonium hydroxide, or in the instance of salts with known basic parasiticidal compounds, with the particular compound—in either instance, in a suitable solvent.

The quaternary ammonium salts of the present invention:

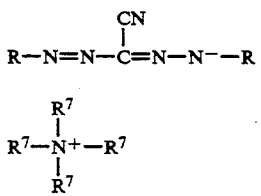

are novel. They are prepared by reacting the parent formazan

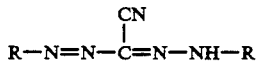

with a quaternary ammonium hydroxide of the formula

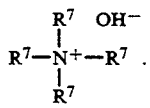

The reaction is carried out in a reaction medium, typically water, and at temperatures over a wide range, conveniently at room temperature. The salt typically precipitates and is recovered by filtration.

The quaternary ammonium salts are also prepared by an alternate synthetic route. In this route, the same active methylene compound described above is reacted with a quaternary ammonium hydroxide of the formula

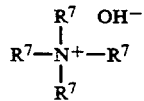

to obtain a compound of the formula

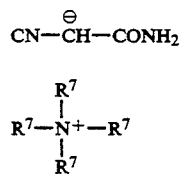

which can be isolated but is typically reacted in situ with a diazonium salt, or sequentially with two different diazonium salts when an asymmetrical product is desired. The reaction yields the desired formazan quaternary ammonium salt directly. Reaction conditions are otherwise the same as described above.

The following syntheses are reported for illustrative purposes.

Symmetrical Formazan 1,5-Bis(4-(trifluoromethyl)phenyl)-3-formazancarbonitrile was prepared as follows:

Sodium nitrite (2.36 grams; 0.34 mole) in 5 ml of water was added slowly to 4-(trifluoromethyl)aniline (5.00 grams; 0.031 mole) in 45 ml of 3N HCl at 0°–5° C. 2-Cyanoacetamide (1.30 gram; 0.015 mole) in about 25 ml of water was added dropwise. The reaction mixture was stirred 20 minutes, filtered, and added dropwise to sodium acetate (22.88 grams; 0.279 mole) in 150 ml of water at room temperature. The reaction mixture was stirred overnight. The product precipitated and was recovered and recrystallized from methanol, yield 2.5 grams, m.p. 234°–236° C.

Asymmetrical Formazan 1-(4-(Trifluoromethyl)phenyl)-5-(4-(trifluoromethylsulfonyloxy)phenyl)-3-formazancarbonitrile was prepared as follows:

Sodium nitrite (0.94 grams; 0.0137 mole) in 2 ml of water was added slowly to p-(trifluoromethyl)aniline (2.0 gram; 0.0124 mole) in 20 ml of 2N HCl. 2-Cyanoacetamide (0.52 gram; 0.062 mole) in ~20 ml of water was next added. The reaction mixture was stirred 30 minutes, filtered, and added dropwise at room temperature to sodium acetate (9.17 gm; 0.1118 mole) in 100 ml of acetic acid. The reaction mixture was stirred 2 hours at room temperature, yielding a precipitate which was separated by filtration and determined to be the desired intermediate, 2-cyano-((4-(trifluoromethyl)phenyl)hydrazono)acetamide, m.p., 225°–227° C.

4-(Trifluoromethylsulfonyloxy)aniline (1.2 gram; 0.005 mole) in 15 ml of 2N HCl was mixed with sodium nitrite (470 mg) at 0°–5° C. This was then added to a solution of the intermediate, 2-cyano-((4-(trifluoromethyl)phenyl)hydrazono)acetamide, in 250 ml of methanol with 5 grams of sodium acetate dissolved in it. The reaction mixture was stirred for 2–3 hours, cooled, and filtered to separate the precipitated solid. TLC showed three spots, and the material was chromatographed using initially 25% methylene chloride/hexane, increasing to 50% methylene chloride for the last band. Three products were obtained, two symmetrical formazans:

1,5-bis(4-(trifluoromethyl)phenyl)-3-formazancarbonitrile, m.p., 235°–237° C.

1,5-bis(4-trifluoromethylsulfonyloxy)phenyl)-3-formazancarbonitrile, m.p., 189°–191° C. and the desired asymmetrical formazan:

1-(4-trifluoromethyl)phenyl)-5-(4-trifluoromethylsulfonyloxy)phenyl)-3-formazancarbonitrile, m.p., 182°–184° C.

Salt

The sodium salt of 1,5-bis(3,4-dichlorophenyl)-3-formazancarbonitrile was prepared as follows.

1,5-bis(3,4-dichlorophenyl)-3-formazancarbonitrile (1.0 gram; 0.0026 mole) and sodium methoxide (0.14 gram; 0.0026 mole) were reacted in 300 ml of methanol. The reaction mixture was stirred overnight at room temperature, then filtered and the methanol evaporated off to obtain the desired product, m.p. 312°–314° C.

Quaternary Ammonium Salt Prepared Using Quaternary Ammonium Salt of Cyanoacetamide The trimethyloctadecylammonium salt of 1,5-bis(4-(trifluoromethyl)phenyl)-3-formazancarbonitrile was prepared as follows:

Sodium nitrite (9.10 grams; 0.132 mole) in 20 ml of water was slowly added to a solution of 4-(trifluoromethyl)aniline (19.32 grams; 0.12 mole) in 200 ml of 2N HCl at 0°-5° C. 2-Cyanoacetamide (5.04 grams; 0.06 mole) in 80 ml of water was then added dropwise. The reaction mixture was stirred 20 minutes, filtered, and added dropwise to trimethyloctadecylammonium bromide (35.0 grams; 0.07 mole) in a mixture of 250 ml of 2N sodium hydroxide and 500 ml of methanol, at room temperature. A slight rise in temperature occurred. The reaction mixture was stirred overnight. About 1.5 liters of water were added and the reaction mixture was stirred. Solvent was then removed, yielding approximately 31 grams of an orange solid. It was mixed with about 100 ml of ethyl acetate and filtered. The product melted at 86°-88° C.

Formazan/Levamisole Salt 0.1N Sodium hydroxide (13 ml) was added to levamisole hydrochloride (0.33 gram; 0.0014 mole) in 10 ml of water. The free levamisole was extracted into 20 ml of methylene chloride, washed once with water, and dried over magnesium sulfate. It was then added to a solution of 1,5-bis(4-trifluoromethyl)phenyl)-3-formazancarbonitrile (0.5 gram; 0.0013 mole) in 75 ml of methylene chloride. The reaction mixture was allowed to stir for an hour and the methylene chloride was then evaporated off, leaving a gummy solid. It was analyzed by NMR, which confirmed the formation of the levamisole salt of 1,5-bis(4-(trifluoromethyl)phenyl)-3-formazancarbonitrile.

Confirmation was based on the following.

Conversion of 1,5-bis(4-(trifluoromethyl)phenyl)-3-formazancarbonitrile to its tetramethylammonium salt results in two significant NMR changes which are also observed with the levamisole salt.

|  | aromatic protons | proton at 1(5)-position |
|---|---|---|
| parent | 7.8–8.1 ppm (multiplet) | 12–13 ppm |
| tetramethylammonium salt | 7.65 ppm (sharp peak) | - (ionized, proton shifted upfield) |
| levamisole salt | 7.65 ppm (sharp peak) | - (ionized, proton shifted upfield) |

Similarly, conversion of levamisole to its hydrochloride salt results in two significant NMR changes which are also observed with the formazan salt.

|  | aromatic protons | proton at 6-position | protons at 2, 3, and 5-positions |
|---|---|---|---|
| parent | 7.35 ppm | 5.3 ppm (triplet) | 2.8–3.7 ppm (multiplet) |
| HCl salt | 7.4 ppm | 5.7 ppm (triplet) | 3.5–4.3 ppm (multiplet) |
| formazan salt | 7.65 ppm | 5.45 ppm (triplet) | 3.1–3.9 ppm (multiplet) |

Representative compounds to be employed in the present invention, prepared by the foregoing synthetic procedures, include those in the following table.

Formazans

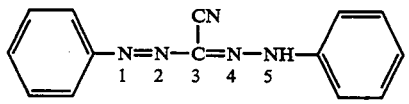

| # | Substituent on 1-φ | Substituent on 5-φ | Salt: | Chemical Name | m.p. (C.) |
|---|---|---|---|---|---|
| 1 | 4-Br | 4-Br | — | 1,5-bis(4-bromophenyl)-3-formazancarbonitrile | 250–253° |
| 2 | 3,4-diCl | 3,4-diCl | — | 1,5-bis(3,4-dichlorophenyl)-3-formazancarbonitrile | 253–255° |
| 3 | 3,4-diCl | 3,4-diCl | Na | 1,5-bis(3,4-dichlorophenyl)-3-formazancarbonitrile sodium salt | 312–314° |
| 4 | 2-CF$_3$ | 2-CF$_3$ | — | 1,5-bis(2-(trifluoromethyl)phenyl)-3-formazancarbonitrile | 159–161° |
| 5 | 3-CF$_3$ | 3-CF$_3$ | — | 1,5-bis(3-(trifluoromethyl)phenyl)-3-formazancarbonitrile | 198–200° |
| 6 | 4-CF$_3$ | 4-CF$_3$ | — | 1,5-bis(4-(trifluoromethyl)phenyl)-3-formazancarbonitrile | 234–236° |
| 7 | 4-CF$_3$ | 4-CF$_3$ | Na | 1,5-bis(4-(trifluoromethyl)phenyl)-3-formazancarbonitrile sodium salt | 245° (dec.) |
| 8 | 4-CF$_3$ | 4-CF$_3$ | tetramethylammonium | 1,5-bis(4-(trifluoromethyl)phenyl)-3-formazancarbonitrile tetramethylammonium salt | 171–173° |
| 9 | 4-CF$_3$ | 4-CF$_3$ | tetraethylammonium | 1,5-bis(4-(trifluoromethyl)phenyl)-3-formazancarbonitrile tetraethylammonium salt | 188–191° |
| 10 | 4-CF$_3$ | 4-CF$_3$ | tetra-n-propylammonium | 1,5-bis(4-(trifluoromethyl)phenyl)-3-formazancarbonitrile tetra-n-propylammonium salt | 223–225° |
| 11 | 4-CF$_3$ | 4-CF$_3$ | tetra-n-butylammonium | 1,5-bis(4-(trifluoromethyl)phenyl)-3-formazancarbonitrile tetra-n-butylammonium salt | 119–121° |
| 12 | 4-CF$_3$ | 4-CF$_3$ | tetra-n-pentylammonium | 1,5-bis(4-(trifluoromethyl)phenyl)-3-formazancarbonitrile tetra-n-pentylammonium salt | 77–79° |
| 13 | 4-CF$_3$ | 4-CF$_3$ | trimethyloctadecylammonium | 1,5-bis(4-(trifluoromethyl)phenyl)-3-formazancarbonitrile trimethyloctadecylammonium salt | 86–88° |
| 14 | 4-OCF$_3$ | 4-OCF$_3$ | — | 1,5-bis(4-(trifluoromethoxy)phenyl)-3-formazancarbonitrile | 213–214° |
| 15 | 4-OCF$_3$ | 4-OCF$_3$ | Na | 1,5-bis(4-(trifluoromethoxy)phenyl)-3-formazancarbonitrile sodium salt | 228–230° |
| 16 | 4-SCF$_3$ | 4-SCF$_3$ | — | 1,5-bis(4-(trifluoromethylthio)phenyl)-3-formazancarbonitrile | 216–219° |
| 17 | 4-CF$_3$ | 4-OSO$_2$CF$_3$ | — | 1-(4-(trifluoromethyl)phenyl)-5-(4-(trifluoromethylsulfonyloxy)phenyl)-3-formazan carbonitrile | 182–184° |

-continued

Formazans

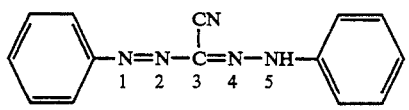

| # | Substituent on 1-φ | Substituent on 5-φ | Salt | Chemical Name | m.p. (C.) |
|---|---|---|---|---|---|
| 18 | 4-OSO$_2$CF$_3$ | 4-OSO$_2$CF$_3$ | — | 1,5-bis(4-trifluoromethylsulfonyloxy)phenyl)-3-formazancarbonitrile | 189–191° |
| 19 | 4-OCF$_2$CF$_2$H | 4-OCF$_2$CF$_2$H | — | 1,5-(bis(4-(1,1,2,2-tetrafluoroethoxy)phenyl)-3-formazancarbonitrile | 212–214° |
| 20 | 2-Cl | 2-Cl | — | 1,5-bis(2-chlorophenyl)-3-formazan carbonitrile | — |
| 21 | 2-F | 2-F | — | 1,5-bis(2-fluorophenyl)-3-formazan carbonitrile | — |
| 22 | 2-Cl-5-CF$_3$ | 2-Cl-5-CF$_3$ | — | 1,5-bis(2-chloro-5-(trifluoromethyl)phenyl)-3-formazancarbonitrile | 129° (dec.) |
| 23 | 2-F-5-CF$_3$ | 2-F-5-CF$_3$ | — | 1,5-bis(2-fluoro-5-(trifluoromethyl)phenyl)-3-formazancarbonitrile | — |
| 24 | 2,3,4,5,6-penta Cl | 2,3,4,5,6-penta Cl | — | 1,5-bis(2,3,4,5,6-pentachlorophenyl)-3-formazancarbonitrile | — |
| 25 | 2,3,4-tri F | 2,3,4-tri F | — | 1,5-bis(2,3,4-trifluorophenyl)-3-formazancarbonitrile | 138–140° |
| 26 | 4-F | 4-F | — | 1,5-bis(4-fluorophenyl)-3-formazancarbonitrile | 234–236° |
| 27 | 4-Cl | 4-CF$_3$ | — | 1-(4-chlorophenyl)-5-(4-(trifluoromethyl)phenyl)-3-formazancarbonitrile | 242–244° |
| 28 | 4-Cl | 4-Cl | — | 1,5-bis(4-chlorophenyl)-3-formazancarbonitrile | 255° (dec) |
| 29 | 4-SCH$_2$CF$_3$ | 4-SCH$_2$CF$_3$ | — | 1,5-bis(4-(2,2,2-trifluoroethylthio)phenyl)-3-formazancarbonitrile | — |

Certain of the compounds are preferred over others. Symmetrical formazans are preferred because of their ease of preparation. The single most preferred compound is 1,5-(bis(4-(trifluoromethyl)phenyl)-3-formazancarbonitrile and its salts. Among salts, the quaternary ammonium salts, those of the formula

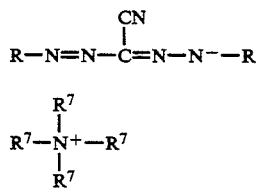

are preferred because they are soluble in lipids such as vegetable oils, and insoluble in water. These salts exhibit increased bioavailability in animals.

The present methods can be utilized for protection against a wide range of parasitic organisms. Protection is achieved in animals with existing parasitic infections, by eliminating the existing parasites, and/or in animals susceptible to attack by parasitic organisms, by preventing parasitic attack. Thus, "protection" includes both treatment and prevention.

Representative blood-ingesting parasitic organisms include the following:
Platyhelminthes:
  Trematoda such as:
    Clonorchis
    Echinostoma
    Fasciola hepatica (liver fluke)
    Fascioloides magna
    Fasciolopsis
    Metagonimus
    Paragonimus
    Schistosoma spp.
Nemathelminthes:
    Ancylostomum
    Angiostrongylus
    Anisakis
    Ascaris
    Brugia
    Bunostomum
    Cooperia
    Dictyocaulus (lungworm)
    Dipetalonema
    Dirofilaria (heartworm)
    Dracunculus
    Elaeophora
    Gaigeria
    Globocephalus urosubulatus
    Haemonchus
    Metastrongylus (lungworm)
    Muellerius (lungworm)
    Necator americanus
    Onchocerca
    Ostertagia
    Protostrongylus (lungworm)
    Setaria
    Stephanofilaria
    Syngamus
    Toxascaris
    Toxocara
    Trichinella
    Uncinaria stenocephala
    Wucheria bancrofti
Arthropoda
  Crustacea
    Argulus
    Caligus
  Arachnida
    Amblyomma americanum (Lone-star tick)
    Amblyomma maculatum (Gulf Coast tick)
    Argas persicus (fowl tick)
    Boophilus microplus (cattle tick)
    Demodex bovis (cattle follicle mite)
    Demodex canis (dog follicle mite)

*Dermacentor andersoni* (Rocky Mountain spotted fever tick)
*Dermacentor variabilis* (American dog tick)
*Dermanyssus gallinae* (chicken mite)
*Ixodes ricinus* (common sheep tick)
*Knemidokoptes gallinae* (deplumming mite)
*Knemidokoptes mutans* (scaly-leg mite)
*Otobius megnini* (ear tick)
*Psoroptes equi* (scab mite)
*Psoroptes ovis* (scab mite)
*Rhipicephalus sanguineus* (brown dog tick)
*Sarcoptes scabiei* (mange mite)
Insecta:

Aedes, Anopheles, Culex, Culiseta (mosquitoes)

*Bovicola bovis* (cattle biting louse)
*Callitroga hominivorax* (blowfly)
*Chrysops spp.* (deer fly)
*Cimex lectularius* (bed bug)
*Ctenocephalis canis* (dog flea)
*Ctenocephalis felis* (cat flea)
*Culicoides spp.* (midges, sandflies, punkies, or no-see-ums)
*Damalinia ovis* (sheep biting louse)
*Dermatobia spp.* (warble fly)
*Dermatophilus spp.* (fleas)
*Gasterophilus haemorrhoidalis* (nose bot fly)
*Gasterophilus intestinalis* (common horse bot fly)
*Gasterophilus nasalis* (chin fly)
*Glossina spp.* (tsetse fly)
*Haematobia irritans* (horn fly, buffalo fly)
*Haematopinus asini* (horse sucking louse)
*Haematopinus eurysternus* (short nose cattle louse)
*Haematopinus ovillus* (body louse)
*Haematopinus suis* (hog louse)
*Hydrotaea irritans* (head fly)
*Hypoderma bovis* (bomb fly)
*Hypoderma lineatum* (heel fly)
*Linognathus ovillus* (body louse)
*Linognathus pedalis* (foot louse)
*Linognathus vituli* (long nosed cattle louse)
*Lucilia spp.* (maggot fly)
*Melophagus ovinus* (sheep ked)
*Oestrus ovis* (nose bot fly)
*Phormia regina* (blowfly)
*Psorophora*
*Reduvirus spp.* (assassin bug)
*Simulium spp.* (black fly)
*Solenopotes capillatus* (little blue cattle louse)
*Stomoxys calcitrans* (stable fly)
*Tabanus spp.* (horse fly)

Representative non-blood-sucking intestinal parasites include the following:
*Cooperia spp.*
*Oesophagostomum spp.* (nodular worm)
*Trichuris*
*Chabertia* (large bowel worm)
*Trichostrongylus spp.*
*Monezia expansa* (tapeworm)
*Nematodirus spathiger*

Parasitic organisms which live in feces are typically the egg and larval stages of insects such as
*Musca domestica* (housefly)
*Musca autumnalis* (face fly)
*Haematobia spp.* (horn fly, buffalo fly, and others).

The amount of present active agent which is to be employed is not critical and will vary with the identity of the host, the identity of the parasite, the route of administration, whether single or multiple dosing is employed, and other factors known to those skilled in the art. For single dosing, a dose of from 1.0 to 50 mg/kg, and preferably from 5 to 40 mg/kg, will generally be effective. In situations where the host is subject to continuing parasitic pressure, it is generally preferred that the compound of the present invention be administered more than once, such as intermittently over the period of time that the host is subject to parasitic attack. This may be for a brief period of days or several weeks, for a season, or up to a lifetime. Sustained release formulations, which provide delivery over a period of time, are therefore often preferred. When repeated dosing is employed, the compounds can be used at lower rates, such as from 0.1 to 10 mg/kg per day. All doses described above are based on the parent compound of Formula I; when a salt is employed, a correspondingly higher amount should be used to provide the indicated amount of the parent compound. As an exception, however, when the salt is with a parasiticidally active compound such as levamisole, the amount of the parent compound of Formula I can be reduced.

For the control of blood-ingesting parasites, the present compounds must be delivered in a manner to enter and spread through the circulatory system of the host. However, it has been found that this can be achieved by any of numerous routes of administration, for example, intramuscular, intraruminal, intravenous, oral, subcutaneous, and transdermal. If the compound is orally or intraruminally delivered, it may be desirable to protect the compound during its passage through the rumen. Techniques for achieving this are well known.

For the control of non-blood-ingesting intestinal parasites and the inhibition of parasitic organisms in feces, the present compounds must be present in the intestinal tract; most conveniently, the compounds are delivered orally or intraruminally.

For some modes of delivery, such as in gelatin capsules, the present compounds can be employed neat. However, for most delivery techniques, the compounds are formulated with one or more physiologically acceptable carriers. Formulation techniques are well known in medical and veterinary practice and can readily be chosen for the present invention by those skilled in the art. For oral delivery, the compounds can be formulated in solid forms such as tablets including chewable tablets, capsules, and pastes, or in liquid forms such as syrups, aqueous suspensions, solutions, drenches, and the like. The compounds can also be formulated as boluses. With appropriate design and formulation, the bolus will remain in the rumen of ruminants and provide continued payout of the compound of the present invention over a period of time.

The compounds are conveniently administered to livestock animals via a feedstuff, via the drinking water, or via a mineral block. In the case of feedstuffs, the compound is typically incorporated in a premix which is subsequently added to other feed components to form the finished feed. The compounds can also be formulated as part of the drinking water.

The compounds can also be administered by intraruminal, intramuscular, intravenous, or subcutaneous injection. Typically the compound is formulated in vehicles of lipophilic nature, such as animal or vegetable oils. Parenteral formulations which provide delayed delivery can also be used in delivering the present compounds.

In all of the foregoing formulations, the compounds are mixed with physiologically acceptable carriers suited for the particular mode of delivery. The concentration of the present compound is not critical and will vary with the particular mode of delivery. Thus the concentration may range from 0.1 to 95 percent weight/volume; and in many instances from 1 to 50 percent, weight/volume.

In the control of parasites, combinations are frequently used, to minimize the development of resistance, to increase the spectrum of parasite control, and to minimize the risk of side effects. Therefore, the present compounds can also be employed in combination with one or more known anthelmintics (endectocides) or with one or more known ectoparasiticides. Preferred combinations are those with anthelmintics. Representative known parasiticides with which the present compounds can be combined include the following:

among the anthelmintics:
albendazole
bunamidine
coumaphos
dichlorvos
epsiprantel
febantel
fenbendazole
flubendazole
ivermectin
levamisole
mebendazole
milbemycin
morantel
moxidectin
netobimin
niclosamide
nitroscanate
oxfendazole
oxibendazole
piperazine
praziquantel
pyrantel
ricobendazole
tetramisole
thiabendazole
among the flukicides:
clorsulon
closantel
diamphenethide
nitroxynil
oxyclozanide
rafoxanide
triclabendazole
among the ectoparasiticides:
alphamethrin
amitraz
coumaphos
cycloprothrin
cyfluthrin
cyhalothrin
cypermethrin
cyromazine
deltamethrin
diazinon
diflubenzuron
dioxathion
fenthion
fenvalerate
flucythrinate
flumethrin
ivermectin
methoprene
metriphonate
moxidectin
permethrin
phosmet
pirimiphos
propetamphos
propoxur
rotenone
temephos
tetrachlorvinphos The present invention is illustrated by the following examples.

The compounds were formulated for evaluation in animals. Most typically, a compound was formulated by merely dissolving it in polyethylene glycol 200 (referred to below as a PEG 200 formulation). Other formulations were utilized for many of the tests; in these other formulations, the particular compound was in most instances dissolved in either N-methyl-2-pyrrolidone or ethyl acetate, and then extended with refined sesame oil. Commonly, Span 80 (a sorbitan monooleate nonionic surfactant sold by ICI Americas Inc.) was also added. The following formulations were prepared.

FORMULATIONS A & B

| | |
|---|---|
| 1,5-bis(4-(trifluoromethyl)phenyl)-3-formazancarbonitrile | 452.4 mg |
| N-methyl-2-pyrrolidone | 2.25 ml |
| Sesame oil, refined | 6.75 ml |
| 1,5-bis(4-(trifluoromethyl)phenyl)-3-formazancarbonitrile | 351.7 mg |
| N-methyl-2-pyrrolidone | 11.75 ml |
| Sesame oil, refined | 4.20 ml |
| Span 80 | 1.05 ml |

Each of these two formulations contained the compound at 50 mg/ml (5% w/v). They and a vehicle blank were used in conducting Test 5, below. The vehicle blank consisted of the vehicle of Formulation A, that is, N-methyl2-pyrrolidone and refined sesame oil, only.

FORMULATIONS C, D, & E

| | |
|---|---|
| 1,5-bis(4-(trifluoromethyl)phenyl)-3-formazancarbonitrile | 4204.3 mg |
| N-methyl-2-pyrrolidone | 21.0 ml |
| Sesame oil, refined | 21.0 ml |
| 1,5-bis(4-(trifluoromethyl)phenyl)-3-formazancarbonitrile | 3996.4 mg |
| N-methyl-2-pyrrolidone | 20.0 ml |
| Sesame oil, refined | 16.0 ml |
| Span 80 | 4.0 ml |
| 1,5-bis(4-(trifluoromethyl)phenyl)-3-formazancarbonitrile | 4204.6 mg |
| N-methyl-2-pyrrolidone | 21.0 ml |

The compound concentration in these was 100 mg/ml, 100 mg/ml, and 200 mg/ml, respectively (10%, 10%, and 20%, respectively, all w/v). Vehicle blanks were also prepared corresponding to each of the three formulations. All of these formulations and blanks were utilized in conducting Test 14 below.

FORMULATION F

| | |
|---|---|
| 1,5-bis(4-(trifluoromethyl)phenyl)-3-formazancarbonitrile | 4500.0 mg |
| N-methyl-2-pyrrolidone | 22.5 ml |
| Sesame oil, refined | 18.0 ml |
| Span 80 | 4.5 ml |

The compound concentration was 100 mg/ml (10% w/v). A vehicle blank was also prepared. This formulation and vehicle blank were employed in conducting Tests 9 and 15, below.

FORMULATION G

| | |
|---|---|
| Tetra-n-butylammonium salt of 1,5-bis(4-(trifluoromethyl)phenyl)-3-formazancarbonitrile | 7994.4 mg |
| N-methyl-2-pyrrolidone | 40.0 ml |
| Sesame oil, refined | 32.0 ml |
| Span 80 | 8.0 ml |

This formulation contained 100 mg of the indicated salt/ml of formulation (10% w/v). It and a vehicle blank were used to conduct Tests 10 and 16, below.

FORMULATION H

| | |
|---|---|
| 1,5-bis(4-(trifluoromethyl)phenyl)-3-formazancarbonitrile | 8045.5 mg |
| N-methyl-2-pyrrolidone | 40.0 ml |
| Sesame oil, refined | 32.0 ml |
| Span 80 | 8.0 ml |

This formulation provided 100 mg of compound/ml of formulation (10% w/v). It and a vehicle blank were employed in conducting Test 12, below.

FORMULATIONS I, J, & K

Salts of 1,5-bis(4-trifluoromethyl)phenyl)-3-formazancarbonitrile were formulated as follows:

| | |
|---|---|
| Tetramethylammonium salt | 4511.2 mg |
| Ethyl acetate | 22.5 ml |
| Sesame oil, refined | 31.5 ml |
| Span 80 | 4.5 ml |
| Tetra-n-propylammonium salt | 4996.4 mg |
| Ethyl acetate | 50.0 ml |
| Sesame oil, refined | 32.5 ml |
| Span 80 | 5.0 ml |
| Trimethyloctadecylammonium salt | 6004.1 mg |
| Ethyl acetate | 30.0 ml |
| Sesame oil, refined | 39.0 ml |
| Span 80 | 6.0 ml |

These three formulations contained the respective salt at a concentration of 76.9 mg/ml (7.69% w/v), 57.14 mg/ml (5.714% w/v), and 80 mg/ml (8% w/v), respectively. Additional quantities were prepared with the same composition. All formulations and the corresponding vehicle blank were employed in conducting Tests 6, 8, and 17, below.

FORMULATIONS L, M, & N

Three additional salts of 1,5-bis(4-(trifluoromethyl)phenyl)-3-formazancarbonitrile were formulated for evaluation, as below:

| | |
|---|---|
| Tetra-n-butylammonium salt | 8200.0 mg |
| Ethyl acetate | 82.0 ml |
| Sesame oil, refined | 53.3 ml |
| Span 80 | 8.2 ml |
| Tetraethylammonium salt | 6700.0 mg |
| Ethyl acetate | 95.75 ml |
| Sesame oil, refined | 43.55 ml |
| Span 80 | 6.70 ml |
| Tetra-n-pentylammonium salt | 8900.0 mg |
| Ethyl acetate | 89.0 ml |
| Sesame oil, refined | 57.85 ml |
| Span 80 | 8.9 ml |

These formulations contained 57.14 mg/ml (5.714% w/v); 45.89 mg/ml (4.589% w/v); and 57.14 mg/ml (5.714% w/v) of the respective salt. The formulations, along with a vehicle blank, were employed in conducting Tests 7 and 22, below.

FORMULATION O

| | |
|---|---|
| 1,5-bis(4-(trifluoromethyl)phenyl)-3-formazancarbonitrile trimethyloctadecylammonium salt | 30,000.00 mg |
| Ethyl acetate | 150.0 ml |
| Sesame oil, refined | 195.0 ml |
| Span 80 | 30.0 ml |

Portions of this formulation, containing 80 mg/ml of the active ingredient (8% w/v), and the vehicle control, were employed in conducting Tests 26 and 27, below. The remaining portions, along with Formulation P, were used in conducting Test 23.

FORMULATION P

| | |
|---|---|
| 1,5-bis(4-(trifluoromethyl)phenyl)-3-formazancarbonitrile trimethyloctadecylammonium salt | 6000.0 mg |
| Ethyl acetate | 30.0 ml |
| Sesame oil, refined | 39.0 ml |
| Span 80 | 6.0 ml |

This formulation contained 80 mg/ml of the salt (8% w/v). It and a vehicle blank were employed in conducting Test 23, below.

FORMULATION Q

| | |
|---|---|
| 1,5-bis(4-(trifluoromethyl)phenyl)-3-formazancarbonitrile trimethyloctadecylammonium salt | 70,000.00 mg |
| Ethyl acetate | 350.0 ml |
| Sesame oil, refined | 455.0 ml |
| Span 80 | 70.0 ml |

This formulation contained 80 mg/ml (8% w/v); it and a vehicle blank were used in Test 29.

FORMULATION R

| | |
|---|---|
| 1,5-bis(4-(trifluoromethyl)phenyl)-3-formazancarbonitrile trimethyloctadecylammonium salt | 50,000.00 mg |
| Ethyl acetate | 250.0 ml |
| Sesame oil, refined | 325.0 ml |
| Span 80 | 50.0 ml |

This formulation contained 80 mg/ml (8% w/v); it and a vehicle blank were employed in Tests 13 and 30.

FORMULATION S

An emusifiable concentrate was prepared according to standard procedures from the following ingredients

| | |
|---|---|
| 1,5-bis(4-(trifluoromethyl)phenyl)-3-formazancarbonitrile trimethyloctadecylammonium salt | 8500.0 mg |
| Ethyl acetate | 42.5 ml |
| Drakeol 6VR (a light mineral oil sold by Pennsylvania Refining Company) | 34.0 ml |
| Montanide 888 (a mannide oleate adjuvant sold by Seppic, Paris, France) | 8.5 ml | to provide a concentration of 100 mg/ml of the active ingredient (10% w/v). This formulation and a vehicle blank were employed in Test 24.

FORMULATION T

Another emulsifiable concentrate was prepared from the following ingredients

| | |
|---|---|
| 1,5-bis(4-(trifluoromethyl)phenyl)-3-formazancarbonitrile trimethyloctadecylammonium salt | 13,000.0 mg |
| Ethyl acetate | 65.0 ml |
| Drakeol 6VR | 52.0 ml |
| Montanide 888 | 13.0 ml | to provide a concentration of 100 mg of the active ingredient per ml (10% w/v). This formulation and a vehicle blank were used in Test 25.

FORMULATION U

The following formulation was prepared

| | |
|---|---|
| 1,5-bis(4-(trifluoromethyl)phenyl)-3-formazancarbonitrile trimethyloctadecylammonium salt | 6000.0 mg |
| Ethyl acetate | 30.0 ml |
| Sesame oil, refined | 39.0 ml |
| Span 80 | 6.0 ml | to provide 80 mg of active ingredient per ml (8% w/v). The formulation and a vehicle blank were utilized in Test 28.

FORMULATION V

An aqueous suspension was prepared according to standard procedures from the following materials:

| | |
|---|---|
| 1,5-bis(4-(trifluoromethyl)phenyl)-3-formazancarbonitrile trimethyloctadecylammonium salt | 4.00 g |
| Propylene glycol | 5.00 g |
| Tergitol + TMN-6 (an ethoxylated trimethylnonanol nonionic surfactant sold by Union Carbide Corp.) | 2.00 g |
| 2% Xanthan gum solution | 5.00 g |
| Polyfon H (a sodium lignosulfonate, sold by Westvaco Corp.) | 0.25 g |
| Water, purified | 33.65 g |
| Antifoam A (a dimethylpolysiloxane, sold by Dow Corning) | 0.10 g |
| | 50.00 g |

This formulation provided 80 mg of active ingredient per ml (8% w/v).

FORMULATION W

Gelatin capsules were prepared, for evaluation in dogs. Two salts of 1,5-bis(4-(trifluoromethyl)phenyl)-3-formazancarbonitrile were used, the tetramethylammonium salt and the trimethyloctadecylammonium salt. Each of the salts was air milled in a Troust Laboratory Air Mill to a median particle size of approximately 10 to 20 microns, and then filled into #0 gelatin capsules, in the amount of 150 mg of the tetramethylammonium salt per capsule, and 225 mg of the trimethyloctadecylammonium salt per capsule. Placebos were prepared with the same size of gelatin capsules, each filled with 225 mg of sucrose.

TESTS AGAINST

*Phormia regina* (blow fly) and *Stomoxys calcitrans* (stable fly)

Various of the compounds to be employed in the present invention were evaluated in preliminary tests for the control of the larval phase of the adult stage of *Stomoxys calcitrans* (stable fly). This preliminary test employed a stock solution of the respective compound. This same test was also conducted as an adjunct to in vivo tests reported below. In this instance, the test employed serum (or in some cases, whole blood) from treated animals. The preliminary test was conducted against only *Stomoxys calcitrans* (stable fly); testing of serum or whole blood was against both *Stomoxys calcitrans* as well as *Phormia regina* (blow fly). The test precedures were as follows.

The compound to be evaluated was dissolved in 1 part acetone/1 part ethanol to provide a stock solution of the compound at a concentration of 5,000 ppm; this solution was shaken for 15 minutes on a sonicator. Portions of the stock solution were placed in 15 ml test tubes, and portions of bovine serum were added to provide the desired dilution of the test compound. Alternately, a sample of serum or blood was used and placed in the test tubes. A dental wick was placed in each test tube and the serum allowed to saturate the wick.

For the blow fly test, approximately 20 blow fly larvae were placed onto the top center of the saturated dental wick, and the test tube was plugged with cotton and incubated at 27° C. and 70% humidity for 24 and 48 hours. Larval mortality counts were then made, and adjusted for any mortality in the vehicle control, to determine percent efficacy against blow fly.

For the adult stable fly test, the saturated wick was placed on a filter paper in a petri dish, and approximately 10 chilled live, hungry stable files were placed on the center of the dish bottom. The dish was covered and allowed to incubate at 27° C. and 60% relative humidity for 48 hours. Mortality readings were made at each of 24 and 48 hours, and adjusted for any mortality in the vehicle control, to determine percent efficacy against adult stable fly.

The results of the stable fly tests which were conducted using stock solution and untreated bovine serum are set forth in the following table. Tests using bovine serum or blood from treated animals are reported below.

| Test Compound | Concentration (ppm) | Percent Efficacy against Adult Stable fly 24 hours | Percent Efficacy against Adult Stable fly 48 hours |
|---|---|---|---|
| 1,5-bis(4-bromophenyl)-3-formazancarbonitrile | 100 | 60 | 100 |
| | 50 | 90 | 100 |
| | 25 | NT | 100 |
| | 10 | 50 | 90 |
| | 25 | 40 | NT |
| | 10 | 40 | 100 |
| | 5 | 0 | 80 |
| | 2.5 | 0 | 40 |
| | 1.25 | 30 | 40 |
| 1,5-bis(3,4-dichlorophenyl)-3-formazancarbonitrile | 100 | 100 | 100 |
| | 100 | 100 | 100 |
| | 50 | 80 | 100 |
| | 25 | 40 | 70 |
| | 10 | 40 | 60 |
| | 25 | 10 | 90 |
| | 10 | 20 | 50 |
| | 5 | 10 | 10 |
| | 2.5 | 10 | 10 |
| 1,5-bis(3,4-dichlorophenyl)-3-formazancarbonitrile sodium salt | 100 | 100 | 100 |
| | 100 | 100 | 100 |
| | 50 | 90 | 100 |
| | 25 | 80 | 100 |
| | 10 | 80 | 100 |
| | 25 | 90 | 100 |
| | 10 | 90 | 100 |
| | 5 | 80 | 100 |
| | 2.5 | 80 | 100 |
| | 10 | 60 | 100 |
| | 5 | 30 | 90 |
| | 2 | 40 | 100 |
| | 1 | 10 | 50 |
| | 0.5 | 0 | 20 |
| 1,5-bis(4-(trifluoromethyl)phenyl)-3-formazancarbonitrile | 100 | 100 | 100 |
| | 50 | 100 | 100 |
| | 25 | 80 | 100 |
| | 10 | 70 | 100 |
| | 25 | 100 | 100 |
| | 10 | 60 | 100 |
| | 5 | 40 | 90 |
| | 2.5 | 0 | 60 |
| | 10 | 100 | 100 |
| | 5 | 90 | 100 |
| | 2 | 80 | 100 |
| | 1 | 60 | 100 |
| | 0.5 | 20 | 70 |
| 1,5-bis(4-(trifluoromethyl)phenyl)-3-formazancarbonitrile tetramethylammonium salt | 5 | 60 | 100 |
| | 2 | 30 | 100 |
| | 1 | 20 | 100 |
| | 0.5 | 0 | 40 |
| 1,5-bis(4-(trifluoromethyl)phenyl)-3-formazancarbonitrile tetraethylammonium salt | 100 | 100 | 100 |
| | 50 | 100 | 100 |
| | 25 | 80 | 100 |
| | 10 | 50 | 90 |
| | 5 | 50 | 90 |
| | 5 | 20 | 100 |
| | 2 | 10 | 80 |
| | 1 | 20 | 20 |
| | 0.5 | 10 | 10 |
| 1,5-bis(4-(trifluoromethyl)phenyl)-3-formazancarbonitrile tetra-n-propylammonium salt | 100 | 100 | 100 |
| | 50 | 100 | 100 |
| | 25 | 80 | 100 |
| | 10 | 80 | 100 |
| | 10 | 60 | 100 |
| | 5 | 70 | 100 |
| | 2 | 40 | 90 |
| | 1 | 40 | 70 |
| | 0.5 | 20 | 30 |
| 1,5-bis(4-(trifluoromethyl)phenyl)-3-formazancarbonitrile tetra-n-butylammonium salt | 100 | 90 | 100 |
| | 50 | 90 | 100 |
| | 25 | 80 | 100 |
| | 10 | 40 | 100 |
| | 10 | 20 | 100 |
| | 5 | 40 | 100 |
| | 2 | 60 | 90 |
| | 1 | 0 | 70 |
| | 0.5 | 20 | 50 |
| 1,5-bis(4-(trifluoromethyl)phenyl)-3-formazancarbonitrile tetra-n-pentylammonium salt | 100 | 100 | 100 |
| | 50 | 70 | 100 |
| | 25 | 60 | 100 |
| | 10 | 40 | 100 |
| | 5 | 40 | 100 |
| | 2 | 40 | 80 |
| | 1 | 40 | 70 |
| | 0.5 | 20 | 60 |
| 1,5-bis(4-(trifluoromethyl)phenyl)-3-formazancarbonitrile trimethyloctadecylammonium salt | 100 | 100 | 100 |
| | 50 | 100 | 100 |
| | 25 | 80 | 100 |
| | 10 | 40 | 100 |
| | 10 | 90 | 100 |
| | 5 | 80 | 100 |
| | 2 | 80 | 90 |
| | 1 | 50 | 90 |
| | 0.5 | 40 | 50 |
| | 25 | 100 | NT |
| | 10 | 80 | NT |
| | 5 | 40 | NT |
| | 2.5 | 10 | NT |
| | 1 | 0 | NT |
| | 25 | 100 | NT |
| | 10 | 100 | NT |
| | 5 | 50 | NT |
| | 2.5 | 10 | NT |
| | 1 | 0 | NT |
| 1,5-bis(4-(trifluoromethoxy)phenyl)-3-formazancarbonitrile | 100 | 100 | 100 |
| | 100 | 100 | 100 |
| | 50 | 90 | 100 |
| | 25 | 100 | 100 |
| | 10 | 70 | 100 |
| | 25 | 100 | 100 |
| | 10 | 80 | 100 |
| | 5 | 60 | 90 |
| | 2.5 | 20 | 60 |
| | 10 | 70 | 100 |
| | 5 | 20 | 100 |
| | 2 | 20 | 70 |
| | 1 | 0 | 40 |
| | 0.5 | 20 | 30 |
| 1,5-bis(4-(trifluoromethoxy)phenyl)-3-formazancarbonitrile sodium salt | 100 | 100 | 100 |
| | 25 | 90 | 100 |
| | 10 | 70 | 100 |
| | 5 | 20 | 90 |
| | 2.5 | 20 | 80 |
| | 10 | 70 | 100 |
| | 5 | 50 | 100 |
| | 2 | 30 | 70 |
| | 1 | 10 | 10 |
| | 0.5 | 20 | 20 |
| 1,5-bis(4-(trifluoromethylthio)phenyl)-3-formazancarbonitrile | 100 | 100 | 100 |
| | 50 | 100 | 100 |
| | 25 | 100 | 100 |
| | 10 | 80 | 100 |
| | 5 | 70 | 100 |
| | 10 | 80 | 100 |
| | 5 | 60 | 100 |
| | 2.5 | 40 | 100 |
| | 1.25 | 30 | 70 |
| | 10 | 80 | 100 |
| | 5 | 70 | 100 |
| | 2 | 40 | 90 |
| | 1 | 30 | 70 |
| | 0.5 | 30 | 40 |
| 1-(4-(trifluoromethyl)phenyl)-5-(4-(trifluoromethylsulfonyloxy)phenyl)-3-formazancarbonitrile | 100 | 100 | 100 |
| | 50 | 100 | 100 |
| | 25 | 100 | 100 |
| | 10 | 100 | 100 |
| | 10 | 90 | 100 |
| | 5 | 50 | 100 |
| | 2.5 | 50 | 80 |
| | 1.25 | 0 | 40 |

-continued

| Test Compound | Concentration (ppm) | Percent Efficacy against Adult Stable fly 24 hours | 48 hours |
|---|---|---|---|
| | 0.625 | 0 | 20 |
| 1,5-bis(4-trifluoromethylsulfonyloxy)phenyl-3-formazancarbonitrile | 100 | 100 | 100 |
| | 50 | 100 | 100 |
| | 25 | 100 | 100 |
| | 10 | 90 | 100 |
| | 5 | 70 | 100 |
| | 2.5 | 20 | 20 |
| | 1.25 | 10 | 20 |
| | 0.625 | 10 | 10 |
| | 50 | 100 | 100 |
| | 20 | 60 | 100 |
| | 10 | 20 | 90 |
| | 5 | 0 | 10 |
| | 10 | 70 | 100 |
| | 5 | 10 | 70 |
| | 2.5 | 10 | 30 |
| | 1.25 | 0 | 20 |
| | 0.625 | 0 | 10 |
| 1,5-bis(4-(1,1,2,2-tetrafluoroethoxy)phenyl)-3-formazancarbonitrile | 100 | 80 | 100 |
| | 100 | 90 | 100 |
| | 50 | 70 | 100 |
| | 25 | 50 | 100 |
| | 10 | 50 | 100 |

NT = Not Tested

TEST AGAINST *HAEMONCHUS CONTORTUS* IN SHEEP (Test 1-10 and Tables 1-10)

Representative compounds to be employed in the present invention were evaluated in wormy sheep; these sheep were naturally infected with Haemonchus contortus and oftentimes were additionally infected with other species, mostly *Trichostrongylus colubriformis*. The evaluations were carried out as follows. The respective compound was formulated, in many tests by simply dissolving it in polyethylene glycol 200 ("PEG 200 Formulation"). Each formulation was administered to the sheep, generally as a single intraruminal injection. Typically there were two sheep in each treatment group and one sheep in the vehicle control group. Fecal material was collected daily both pre and post treatment, and the number of eggs/gram of feces was determined. For those animals with >75% reduction in eggs/gram of feces, the total worm passage was determined and the animals were necropsied and counts made of internal worms not passed.

In addition, blood samples were taken from the sheep prior to administration of the test compound, and post treatment at 30 minutes, 5 hours, 24 hours, and daily up to 7 days after treatment. These samples were evaluated in vitro for control of *Phormia regina* and *Stomoxys calcitrans*, employing the methods described above.

Results of these evaluations are set forth below. Deviations from the general procedures are noted. Throughout the tables, "VC" means the vehicle control. No adverse reactions by the sheep were described in any of the trials.

TABLE 1A

Test 1: Evaluation of 1,5-bis(4-(trifluoromethyl)phenyl)-3-formazancarbonitrile, at 10 mg/kg Bodyweight (PEG 200 Formulation)

Activity Against *Haemonchus contortus* ("H") and *Trichostrongylus colubriformis* ("T")

| | Worm Eggs Per Gram of Feces (EPG) | | | | | | | | | | | |
|---|---|---|---|---|---|---|---|---|---|---|---|---|
| | Pre* | | Days Following Treatment | | | | | | | | | |
| | | | 1 | | 2 | | 3 | | 4 | | 5–7 | |
| Treatment | H | T | H | T | H | T | H | T | H | T | H | T |
| Treated | 867 | 133 | 200 | 200 | 0 | 0 | 0 | 0 | 0 | 0 | 0 | 0 |
| Treated | 933 | 700 | 600 | 400 | 300 | 900 | 0 | 400 | 0 | 0 | 0 | 466.7 |
| VC | 533 | 0 | 800 | 0 | 500 | 0 | 600 | 0 | 900 | 0 | 733 | 0 |

| | % EPG Reduction | | Total Number Worm Passed | | Counts[1] | | Percent Reduction | |
|---|---|---|---|---|---|---|---|---|
| Treatment | H | T | H | T | H | T | H | T |
| Treated | 100 | 100 | 117** | ND | 0 | 0 | 100 | 100 |
| Treated | 100 | 33.4 | 11** | ND | 0 | 393 | 100 | ND |
| VC | 0 | — | ND | ND | ND | ND | | |

*Average of 3 days sampling
**Very small immature 75% F
[1]At necropsy 7 days following treatment
ND = not done

TABLE 1B

Percent Insecticidal Activity Against *Phormia regina* ("L") and *Stomoxys calcitrans* ("A") Following 24 hr in vitro Exposure

| | Day 0 | | 30 Min | | 5 Hr | | Day 1 | | Day 2 | | Day 3 | | Day 4 | | Day 5 | | Day 6 | | Day 7 | |
|---|---|---|---|---|---|---|---|---|---|---|---|---|---|---|---|---|---|---|---|---|
| Treatment | L | A | L | A | L | A | L | A | L | A | L | A | L | A | L | A | L | A | L | A |
| Treated | 0 | 0 | 0 | 10 | 100 | 100 | 100 | 100 | 75 | 20 | 0 | 0 | 0 | 0 | 0 | 10 | 0 | 10 | 0 | 0 |
| Treated | 0 | 0 | 0 | 10 | 100 | 100 | 100 | 100 | 100 | 60 | 0 | 0 | 0 | 0 | 0 | 0 | 0 | 0 | 0 | 0 |
| VC | 0 | 0 | 0 | 0 | 0 | 0 | 0 | 0 | 0 | 0 | 0 | 0 | 0 | 10 | 0 | 10 | 0 | 0 | 0 | 0 |

TABLE 1C

Percent Insecticidal Activity Against *Phormia regina* ("L") and *Stomoxys calcitrans* ("A")

TABLE 1C-continued

| | Following 48 hr in vitro Exposure | | | | | | | | | | | | | | | | | | |
|---|---|---|---|---|---|---|---|---|---|---|---|---|---|---|---|---|---|---|---|
| | Day 0 | | 30 Min | | 5 Hr | | Day 1 | | Day 2 | | Day 3 | | Day 4 | | Day 5 | | Day 6 | | Day 7 | |
| Treatment | L | A | L | A | L | A | L | A | L | A | L | A | L | A | L | A | L | A | L | A |
| Treated | 0 | 0 | 0 | 0 | 100 | 100 | 100 | 100 | 90 | 70 | 0 | 100 | 0 | 20 | 0 | 10 | 0 | 0 | 0 | 0 |
| Treated | 0 | 0 | 0 | 0 | 100 | 100 | 100 | 100 | 100 | 100 | 0 | 30 | 0 | 0 | 0 | 0 | 0 | 0 | 0 | 0 |
| VC | 0 | 0 | 0 | 0 | 0 | 0 | 0 | 0 | 0 | 0 | 0 | 0 | 0 | 0 | 0 | 0 | 0 | 0 | 0 | 0 |

TABLE 2A

Test 2: Evaluation of 1,5-bis(4-(trifluoromethyl)phenyl)-3-formazancarbonitrile, at 5 mg/kg Bodyweight (PEG 200 Formulation)

Activity Against *Haemonchus contortus* ("H") and *Trichostrongylus colubriformis* ("T")

| | Worm Eggs Per Gram of Feces (EPG) | | | | | | | | % EPG Reduction | | Total Number Worm | | | | Percent of Worms | |
|---|---|---|---|---|---|---|---|---|---|---|---|---|---|---|---|---|
| | Pre* | | Days Following Treatment | | | | | | | | Passed | | Counts[1] | | | |
| | | | 1 | | 2 | | 5-7 | | | | | | | | | |
| Treatment | H | T | H | T | H | T | H | T | H | Others | H | Others | H | Others | H | Others |
| Treated | 7833 | 433 | 5900 | 200 | 0 | 100 | 0 | 0 | 100 | 100 | 0 | ND | 0 | 0 | 100 | 100 |
| Treated | 5533 | 433 | 2600 | 300 | 100 | 200 | 0 | 250 | 100 | 42.3 | 17** | ND | 0 | 29 | 100 | 87.8 |
| VC | 1767 | 300 | 2800 | 100 | 1900 | 100 | 2750 | 300 | 0 | 0 | 0 | ND | 840 | 238 | — | — |

*Average of 3 days sampling
**Pieces of worms
[1]At necropsy 7 days following treatment
ND = not done
Others = identified as *Trichostrongylus colubriformis* and *Ostertagia spp.*

TABLE 2B

Percent Insecticidal Activity Against *Phormia regina* ("L") and *Stomoxys calcitrans* ("A")
Following 24 hr in vitro Exposure

| | Day 0 | | 30 Min | | 5 Hr | | Day 1 | | Day 2 | | Day 3 | | Day 4 | | Day 5 | |
|---|---|---|---|---|---|---|---|---|---|---|---|---|---|---|---|---|
| Treatment | L | A | L | A | L | A | L | A | L | A | L | A | L | A | L | A |
| Treated | 0 | 10 | 0 | 0 | 100 | 100 | 100 | 100 | 100 | 60 | 25 | 0 | 0 | 0 | 0 | 20 |
| Treated | 0 | 0 | 0 | 0 | 100 | 90 | 100 | 100 | 0 | 0 | 0 | 0 | 0 | 10 | 0 | 0 |
| VC | 0 | 10 | 0 | 0 | 0 | 0 | 0 | 0 | 0 | 0 | 0 | 20 | 0 | 0 | 0 | 10 |

TABLE 2C

Percent Insecticidal Activity Against *Phormia regina* ("L") and *Stomoxys calcitrans* ("A")
Following 48 hr in vitro Exposure

| | Day 0 | | 30 Min | | 5 Hr | | Day 1 | | Day 2 | | Day 3 | | Day 4 | | Day 5 | |
|---|---|---|---|---|---|---|---|---|---|---|---|---|---|---|---|---|
| Treatment | L | A | L | A | L | A | L | A | L | A | L | A | L | A | L | A |
| Treated | 0 | 20 | 10 | 70 | 100 | 100 | 100 | 100 | 100 | 100 | 90 | 100 | 60 | 100 | 0 | 100 |
| Treated | 0 | 0 | 0 | 20 | 100 | 100 | 100 | 100 | 10 | 100 | 0 | 0 | 0 | 20 | 0 | 10 |
| VC | 0 | 0 | 0 | 0 | 0 | 0 | 0 | 0 | 0 | 0 | 0 | 0 | 0 | 0 | 0 | 0 |

TABLE 3A

Activity Against *Haemonchus contortus*
Test 3: 1,5-bis(4-bromophenyl)-3-formazancarbonitrile (Cmpd 1) at 10 mg/kg and
1,5-bis(4-(trifluoromethylsulfonyloxy)-3-formazancarbonitrile (Cmpd 18) at 5 mg/kg,
Each in PEG 200 Formulation

| | | Worm Eggs Per Gram of Feces (EPG) | | | | | | % Worm Egg Reduction | Total Worm Counts | % Worm Reduction |
|---|---|---|---|---|---|---|---|---|---|---|
| | Dose | | Days Following Treatment | | | | | | | |
| Treatment | mg/kg | Pre* | 1 | 2 | 3 | 4 | 5-7* | | | |
| Cmpd 1 | 10 | 733 | 600 | 500 | | 400 | 350 | 52.3 | N/D | — |
| Cmpd 1 | 10 | 233 | 100 | 0 | | 100 | 200 | 14.2 | N/D | — |
| Cmpd 18 | 5 | 433 | 600 | 700 | | 400 | 500 | 0 | N/D | — |
| Cmpd 18 | 5 | 567 | 500 | 500 | | 600 | 500 | 11.8 | N/D | — |
| VC | | 0 | 0 | 0 | | 0 | 0 | | | |

*Average of 3 days sampling
ND = not done

TABLE 3B

Percent Insecticidal Activity Against *Phormia regina* ("L") and *Stomoxys calcitrans* ("A")
Following 24 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A |
|---|---|---|---|---|---|---|---|---|---|---|---|---|---|---|---|---|---|---|---|
| Cmpd 1 | 10 | 0 | 0 | 0 | 20 | 0 | 10 | 0 | 0 | 0 | 0 | 0 | 0 | 0 | 10 | 0 | 10 | 0 | 0 |
| Cmpd 1 | 10 | 0 | 20 | 0 | 30 | 0 | 10 | 0 | 0 | 0 | 0 | 0 | 0 | 0 | 10 | 0 | 0 | 0 | 10 |
| Cmpd 18 | 5 | 0 | 0 | 0 | 10 | 0 | 0 | 0 | 0 | 0 | 0 | 0 | 0 | 0 | 20 | 0 | 0 | 0 | 10 |
| Cmpd 18 | 5 | 0 | 0 | 0 | 20 | 0 | 0 | 0 | 0 | 0 | 0 | 0 | 0 | 0 | 10 | 0 | 10 | 0 | 10 |
| VC | 0 | 0 | 0 | 0 | 0 | 0 | 0 | 0 | 0 | 0 | 0 | 0 | 0 | 0 | 0 | 0 | 0 | 0 | 0 |

TABLE 3C

Percent Insecticidal Activity Against *Phormia regina* ("L") and *Stomoxys calcitrans* ("A")
Following 48 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A |
|---|---|---|---|---|---|---|---|---|---|---|---|---|---|---|---|---|---|---|---|
| Cmpd 1 | 10 | 0 | 0 | 0 | 20 | 0 | 30 | 0 | 20 | 0 | 0 | 0 | 30 | 0 | 10 | 0 | 10 | 0 | 10 |
| Cmpd 1 | 10 | 0 | 20 | 0 | 40 | 0 | 10 | 0 | 10 | 0 | 30 | 0 | 10 | 0 | 10 | 0 | 0 | 0 | 20 |
| Cmpd 18 | 5 | 0 | 0 | 0 | 30 | 0 | 0 | 0 | 20 | 0 | 20 | 0 | 20 | 0 | 30 | 0 | 0 | 0 | 10 |
| Cmpd 18 | 5 | 0 | 0 | 0 | 30 | 0 | 0 | 0 | 30 | 0 | 10 | 0 | 0 | 0 | 30 | 0 | 10 | 0 | 20 |
| VC | 0 | 0 | 0 | 0 | 0 | 0 | 0 | 0 | 10 | 0 | 20 | 0 | 20 | 0 | 20 | 0 | 0 | 0 | 0 |

TABLE 4A

Activity Against *Haemonchus contortus* ("H"), *Trichostrongylus colubriformis* ("T"),
and Ostertagia spp. ("O")
Test 4: Evaluation of
1,5-bis(3,4-dichlorophenyl)-3-formazancarbonitrile (Cmpd 2)
at 10 mg/kg Bodyweight, and of
1,5-bis(4-(trifluoromethyl)phenyl)-3-formazancarbonitrile (Cmpd 6)
at 2.5 mg/kg Bodyweight, Each, PEG 200 Formulation

| | Worm Eggs Per Gram of Feces (EPG) | | | | | | | | | | | |
|---|---|---|---|---|---|---|---|---|---|---|---|---|
| | Pre* | | Days Following Treatment | | | | | | | | | |
| | | | 1 | | 2 | | 3 | | 4 | | 5-7* | |
| Treatment | H | T | H | T | H | T | H | T | H | T | H | T |
| Cmpd 2 | 10500 | 500 | 7400 | 500 | 2400 | 400 | 2300 | 300 | 1900 | 300 | 1725 | 375 |
| | 3933 | 433 | 4000 | 500 | 1600 | 300 | 1200 | 200 | 1200 | 300 | 1200 | 183 |
| Cmpd 6 | 9233 | 533 | 1400 | 600 | 0 | 0 | 0 | 0 | 0 | 0 | 0 | 0 |
| | 3800 | 633 | 3000 | 400 | 0 | 0 | 0 | 100 | 0 | 0 | 0 | 0 |
| VC | 4033 | 300 | 2800 | 300 | 4800 | 500 | 3400 | 400 | 3200 | 400 | 3600 | 450 |

| Treatment | % Worm Egg Reduction H | % Worm Egg Reduction T | Total Number Worm Passed H** | Counts[1] H | Counts[1] T | Counts[1] O | % Reduction H | % Reduction T | % Reduction O |
|---|---|---|---|---|---|---|---|---|---|
| Cmpd 2 | 82 | 30 | 39 | 916 | 27 | 19 | 0 | 73 | 39 |
| | 72 | 42 | 53 | 556 | 14 | 39 | 13 | 88 | 0 |
| Cmpd 6 | 100 | 100 | 20 | 0 | 0 | 105 | 100 | 100 | 0 |
| | 100 | 100 | 13 | 0 | 0 | 45 | 100 | 100 | 0 |
| VC | 11 | 0 | 0 | 637 | 112 | 31 | — | — | — |

*Average of 3 days sampling
**Mostly pieces of worms
[1]At necropsy 7 days following treatment

TABLE 4B

Percent Insecticidal Activity Against *Phormia regina* ("L") and *Stomoxys calcitrans* ("A")
Following 24 hr in vitro Exposure

| Treatment | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|---|---|---|---|
| Cmpd 2 | 0 | 28 | 0 | 10 | 0 | 40 | 100 | 50 | 0 | 0 | 0 | 30 | 0 | 0 | 0 | 0 |
| | 0 | 0 | 0 | 0 | 0 | 50 | 100 | 50 | 0 | 10 | 0 | 10 | 0 | 30 | 0 | 0 |
| Cmpd 6 | 0 | 0 | 0 | 0 | 100 | 60 | 100 | 70 | 0 | 10 | 0 | 40 | 0 | 10 | 0 | 0 |
| | 0 | 7 | 0 | 10 | 100 | 30 | 100 | 70 | 10 | 50 | 0 | 10 | 0 | 0 | 0 | 0 |
| VC | 0 | 0 | 0 | 0 | 0 | 0 | 0 | 10 | 0 | 0 | 0 | 10 | 0 | 10 | 0 | 0 |

TABLE 4C

Percent Insecticidal Activity Against *Phormia regina* ("L") and *Stomoxys calcitrans* ("A")
Following 48 hr in vitro Exposure

| Treatment | Day 0 | | 30 Min | | 5 Hr | | Day 1 | | Day 2 | | Day 3 | | Day 4 | | Day 5 | |
|---|---|---|---|---|---|---|---|---|---|---|---|---|---|---|---|---|
| | L | A | L | A | L | A | L | A | L | A | L | A | L | A | L | A |
| Cmpd 2 | 0 | 28 | 0 | 0 | 0 | 100 | 100 | 100 | 0 | 20 | 0 | 10 | 0 | 0 | 0 | 0 |
| | 0 | 0 | 0 | 0 | 0 | 90 | 100 | 100 | 0 | 20 | 0 | 0 | 0 | 0 | 0 | 0 |
| Cmpd 6 | 0 | 1 | 0 | 20 | 100 | 90 | 100 | 90 | 25 | 80 | 0 | 90 | 0 | 10 | 0 | 0 |
| | 0 | 7 | 0 | 20 | 100 | 100 | 100 | 100 | 90 | 100 | 0 | 30 | 0 | 30 | 0 | 0 |
| VC | 0 | 0 | 0 | 0 | 0 | 0 | 0 | 0 | 0 | 0 | 0 | 0 | 0 | 0 | 0 | 0 |

TABLE 5A

Activity against *Haemonchus contortus* ("H"), *Ostergia* spp. ("O"),
*Trichostrongylus colubriformis* (T), and *Nematodirus* spp. ("NE")
Test 5: Evaluation of Varying Formulations and Doses of
1,5-bis(4-(trifluromethyl)phenyl)-3-formazancarbonitrile

| Treatment | Dose mg/kg | Worm Eggs Per Gram of Feces (EPG) | | | | | | % Worm Egg Reduction H/O | Total Worm Counts[1] | | | | % Worm Reduction H |
|---|---|---|---|---|---|---|---|---|---|---|---|---|---|
| | | Pre* H/O | Days Following Treatment | | | | | | | | | | |
| | | | 1 H/O | 2 H/O | 3 H/O | 4 H/O | 5-7* H/O | | H | T | O | NE | |
| Formulation A | 5 | 6167/567 | 5800/500 | 0/0 | 0/0 | 0/0 | 0/0 | 100/100 | 0 | 0 | 0 | 17 | 100 |
| Formulation A | 5 | 1133/267 | 500/100 | 0/0 | 0/0 | 0/0 | 0/0 | 100/100 | 0 | 16 | 102 | 1 | |
| PEG 200 Form. | 20 | 2967/400 | 2800/400 | 0/0 | 0/0 | 0/0 | 0/0 | 100/100 | 0 | 0 | 246 | 0 | 100 |
| PEG 200 Form. | 20 | 3367/333 | 2700/200 | 0/0 | 0/0 | 0/0 | 0/0 | 100/100 | 0 | 0 | 61 | 0 | |
| Formulation B | 5 | 7467/567 | 3100/200 | 0/0 | 0/0 | 0/0 | 0/0 | 100/100 | 0 | 0 | 133 | 0 | 100 |
| Formulation B | 5 | 1367/233 | 700/0 | 0/0 | 0/0 | 0/0 | 0/0 | 100/100 | 0 | 0 | 89 | 0 | |
| VC | — | 767/67 | 600/0 | 500/100 | 700/100 | 700/200 | 650/150 | 15/0 | 374 | 29 | 46 | 106 | — |

*Average of 3 days sampling
[1]At necropsy 7 days following treatment

TABLE 5B

Percent Insecticidal Activity Against *Phormia regina* ("L") and *Stomoxys calcitrans* ("A")
Following 24 hr in vitro Exposure

| Treatment | Dose mg/kg | Day 0 | | 30 Min | | 5 Hr | | Day 1 | | Day 2 | | Day 3 | | Day 4 | | Day 5 | | Day 6 | |
|---|---|---|---|---|---|---|---|---|---|---|---|---|---|---|---|---|---|---|---|
| | | L | A | L | A | L | A | L | A | L | A | L | A | L | A | L | A | L | A |
| Formulation A | 5 | 0 | 20 | 0 | 0 | 100 | 80 | 100 | 90 | 100 | 50 | 0 | 0 | 0 | 20 | 0 | 0 | 0 | 0 |
| Formulation B | 5 | 0 | 10 | 0 | 10 | 100 | 50 | 100 | 80 | 100 | 60 | 90 | 10 | 0 | 10 | 0 | 0 | 0 | 0 |
| PEG 200 Form. | 20 | 0 | 0 | 0 | 10 | 100 | 90 | 100 | 60 | 100 | 60 | 0 | 20 | 0 | 50 | 0 | 0 | 0 | 0 |
| PEG 200 Form. | 20 | 0 | 10 | 0 | 0 | 100 | 50 | 100 | 90 | 100 | 40 | 0 | 10 | 0 | 0 | 0 | 0 | 0 | 0 |
| Formulation B | 5 | 0 | 0 | 0 | 0 | 100 | 100 | 100 | 40 | 100 | 70 | 0 | 0 | 0 | 0 | 0 | 0 | 0 | 0 |
| Formulation B | 5 | 0 | 0 | 0 | 0 | 100 | 20 | 100 | 60 | 100 | 60 | 0 | 0 | 0 | 20 | 0 | 0 | 0 | 0 |
| VC | | 0 | 0 | 0 | 0 | 0 | 10 | 0 | 10 | 0 | 10 | 0 | 0 | 0 | 0 | 14 | 0 | 0 | |

TABLE 5C

Percent Insecticidal Activity Against *Phormia regina* ("L") and *Stomoxys calcitrans* ("A")
Following 48 hr in vitro Exposure

| Treatment | Dose mg/kg | Day 0 | | 30 Min | | 5 Hr | | Day 1 | | Day 2 | | Day 3 | | Day 4 | | Day 5 | | Day 6 | |
|---|---|---|---|---|---|---|---|---|---|---|---|---|---|---|---|---|---|---|---|
| | | L | A | L | A | L | A | L | A | L | A | L | A | L | A | L | A | L | A |
| Formulation A | 5 | 0 | 20 | 0 | 0 | 100 | 100 | 100 | 100 | 100 | 100 | 0 | 80 | 0 | 20 | 0 | 4 | 0 | 0 |
| Formulation A | 5 | 0 | 10 | 0 | 70 | 100 | 100 | 100 | 100 | 100 | 100 | 100 | 100 | 90 | 50 | 15 | 54 | 10 | 34 |
| PEG 200 Form. | 20 | 0 | 0 | 0 | 70 | 100 | 100 | 100 | 100 | 100 | 100 | 0 | 90 | 0 | 50 | 0 | 0 | 0 | 0 |
| PEG 200 Form. | 20 | 0 | 10 | 0 | 0 | 100 | 100 | 100 | 100 | 100 | 100 | 100 | 100 | 0 | 0 | 0 | 0 | 0 | 0 |
| Formulation B | 5 | 0 | 0 | 0 | 60 | 100 | 100 | 100 | 100 | 100 | 100 | 0 | 0 | 0 | 40 | 0 | 0 | 0 | 0 |
| Formulation B | 5 | 0 | 0 | 0 | 50 | 100 | 100 | 100 | 100 | 100 | 100 | 100 | 90 | 0 | 40 | 0 | 0 | 0 | 4 |
| VC | | 0 | 0 | 0 | 0 | 0 | 20 | 0 | 10 | 0 | 10 | 0 | 0 | 0 | 0 | 14 | 0 | 0 | |

TABLE 6A

Activity Against *Haemonchus contortus* ("H")
Test 6: Evaluation of Three Salts of 1,5-bis(4-(trifluoromethyl)phenyl)-3-formazancarbonitrile

| Treatment | Dose mg/kg | Worm Eggs Per Gram of Feces (EPG) | | | | | | % Worm Egg Reduction H | Daily Worm Passage | | | | Total Worm Counts[2] H | % Worm Reduction H |
|---|---|---|---|---|---|---|---|---|---|---|---|---|---|---|
| | | Pre* H | Days Following Treatment | | | | | | | | | | | |
| | | | 1 H | 2 H | 3 H | 4 H | 5-7* H | | H | H | H | Total[1] | | |
| Cmpd 8, | 6.0 | 3100 | 1600 | 0 | 0 | 0 | 0 | 100 | 46 | 0 | 0 | 46 | 0 | 100 |

TABLE 6A-continued

Activity Against *Haemonchus contortus* ("H")
Test 6: Evaluation of Three Salts of 1,5-bis(4-(trifluoromethyl)phenyl)-3-formazancarbonitrile

| Treatment | Dose mg/kg | Pre* H | Worm Eggs Per Gram of Feces (EPG) Days Following Treatment | | | | | % Worm Egg Reduction H | Daily Worm Passage | | | | Total Worm Counts[2] H | % Worm Reduction H |
|---|---|---|---|---|---|---|---|---|---|---|---|---|---|---|
| | | | 1 H | 2 H | 3 H | 4 H | 5–7* H | | H | H | H | Total[1] | | |
| Cmpd 8, Form I | 6.0 | 14500 | 13000 | 200 | 0 | 0 | 0 | 100 | 433 | 216 | 14 | 663 | 0 | 100 |
| Cmpd 10, Form J | 7.4 | 2425 | 3900 | 200 | 0 | 0 | 0 | 100 | | | | | 0 | 100 |
| Cmpd 10, Form J | 7.4 | 13400 | 13300 | 400 | 0 | 0 | 0 | 100 | 312 | 191 | 6 | 509 | 0 | 100 |
| Cmpd 13, Form K | 9.0 | 6550 | 6300 | 100 | 0 | 0 | 0 | 100 | 133 | 22 | 0 | 155 | 0 | 100 |
| Cmpd 13, Form K | 9.0 | 8650 | 9600 | 0 | 0 | 0 | 0 | 100 | 161 | 44 | 0 | 205 | 0 | 100 |
| VC | 0 | 825 | 800 | 1100 | 900 | 1500 | 900 | 0 | 0 | 0 | 0 | 0 | ND | |

Cmpd 8 = 1,5-bis(4-(trifluoromethyl)phenyl)-3-formazancarbonitrile tetramethylammonium salt
Cmpd 10 = 1,5-bis(4-(trifluoromethyl)phenyl)-3-formazancarbonitrile tetra-n-propylammonium salt
Cmpd 13 = 1,5-bis(4-(trifluoromethyl)phenyl)-3-formazancarbonitrile trimethyloctadecylammonium salt
*Average of 3 days sampling
[1]Pieces of worm
[2]At necropsy 7 days following treatment
N/D = not determined

TABLE 6B

Percent Insecticidal Activity Against *Phormia regina* ("L") and *Stomoxys calcitrans* ("A")
Following 24 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A |
|---|---|---|---|---|---|---|---|---|---|---|---|---|---|---|---|---|---|---|---|
| Cmpd 8, Form I | 6.0 | 0 | 10 | 0 | 20 | 100 | 20 | 100 | 90 | 10 | 10 | 0 | 20 | 0 | 10 | 0 | 10 | 0 | 0 |
| Cmpd 8, Form I | 6.0 | 0 | 20 | 0 | 10 | 0 | 40 | 100 | 90 | 10 | 20 | 0 | 50 | 0 | 0 | 0 | 10 | 0 | 10 |
| Cmpd 10, Form J | 7.4 | 0 | 10 | 0 | 10 | 10 | 50 | 100 | 80 | 90 | 70 | 10 | 0 | 0 | 0 | 0 | 0 | 0 | 0 |
| Cmpd 10, Form J | 7.4 | 0 | 10 | 0 | 30 | 10 | 20 | 100 | 80 | 10 | 20 | 0 | 0 | 0 | 10 | 0 | 0 | 0 | 0 |
| Cmpd 13, Form K | 9.0 | 0 | 10 | 0 | 10 | 100 | 80 | 100 | 90 | 100 | 20 | 10 | 40 | 0 | 10 | 0 | 20 | 0 | 0 |
| Cmpd 13, Form K | 9.0 | 0 | 10 | 0 | 10 | 100 | 80 | 100 | 100 | 100 | 90 | 80 | 30 | 0 | 30 | 0 | 0 | 0 | 10 |
| VC | 0 | 0 | 10 | 0 | 30 | 0 | 20 | 0 | 10 | 0 | 20 | 0 | 30 | 0 | 10 | 0 | 0 | 0 | 0 |

TABLE 6C

Percent Insecticidal Activity Against *Phormia regina* ("L") and *Stomoxys calcitrans* ("A")
Following 24 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A |
|---|---|---|---|---|---|---|---|---|---|---|---|---|---|---|---|---|---|---|---|
| Cmpd 8, Form I | 6.0 | 0 | 10 | 0 | 30 | 100 | 100 | 100 | 100 | 10 | 90 | 0 | 30 | 0 | 20 | 0 | 30 | 0 | 10 |
| Cmpd 8, Form I | 6.0 | 0 | 30 | 0 | 20 | 0 | 70 | 100 | 100 | 30 | 70 | 0 | 50 | 0 | 10 | 0 | 10 | 0 | 20 |
| Cmpd 10, Form J | 7.4 | 0 | 30 | 0 | 30 | 10 | 90 | 100 | 100 | 100 | 100 | 10 | 60 | 0 | 0 | 0 | 30 | 0 | 40 |
| Cmpd 10, Form J | 7.4 | 0 | 30 | 0 | 40 | 10 | 50 | 100 | 100 | 30 | 100 | 0 | 0 | 0 | 10 | 0 | 30 | 0 | 20 |
| Cmpd 13, Form K | 9.0 | 0 | 30 | 0 | 20 | 100 | 100 | 100 | 100 | 100 | 100 | 10 | 90 | 0 | 40 | 0 | 40 | 0 | 20 |
| Cmpd 13, Form K | 9.0 | 0 | 20 | 0 | 10 | 100 | 100 | 100 | 100 | 100 | 100 | 90 | 90 | 0 | 80 | 0 | 80 | 0 | 10 |
| VC | 0 | 0 | 20 | 0 | 30 | 0 | 30 | 0 | 20 | 0 | 30 | 0 | 30 | 0 | 20 | 0 | 10 | 0 | 10 |

TABLE 7A

Activity Against *Haemonchus contortus* ("H"), *Trichostrongylus colubriformis* ("T"), and *Ostertagia* spp. ("O")
Test 7: Evaluation of Three Salts of 1,5-bis(4-trifluromethyl)phenyl)-3-formazancarbonitrile

| Treatment | Dose mg/kg | Worm Eggs Per Gram of Feces (EPG) | | | | | | | | | | | |
|---|---|---|---|---|---|---|---|---|---|---|---|---|---|
| | | Pre* | | 1 | | 2 | | 3 | | 4 | | 5–7* | |
| | | H | T | H | T | H | T | H | T | H | T | H | T |
| Cmpd 11, Form L | 8.13 | 1433 | 133 | 700 | 100 | 100 | 0 | 0 | 0 | 0 | 0 | 0 | 0 |
| Cmpd 11, Form L | 8.13 | 6933 | 0 | 7100 | 200 | 200 | 200 | 0 | 500 | 0 | 700 | 0 | 666 |
| Cmpd 9, Form M | 6.70 | 7933 | 266 | 4800 | 200 | 300 | 200 | 200 | 100 | 0 | 300 | 0 | 300 |
| Cmpd 9, Form M | 6.70 | 1066 | 200 | 400 | 0 | 0 | 0 | 0 | 0 | 0 | 0 | 0 | 0 |
| Cmpd 12, Form N | 8.85 | 1166 | 133 | 900 | 100 | 100 | 100 | 0 | 0 | 0 | 0 | 0 | 0 |
| Cmpd 12, Form N | 8.85 | 1133 | 233 | 200 | 400 | 0 | 500 | 0 | 800 | 0 | 500 | 0 | 566 |
| VC | 0 | 1133 | 0 | 1000 | 0 | 1100 | 0 | 900 | 0 | 1100 | 0 | 830 | 0 |

| Treatment | Dose mg/kg | % Worm Egg Reduction H | % Worm Egg Reduction T | Daily *H. contortus* Worm Passage 1 H | 2 H | 3 H | Total | Total Worm Counts[1] H | T | O | % Worm Reduction H | T | O |
|---|---|---|---|---|---|---|---|---|---|---|---|---|---|

TABLE 7A-continued

Activity Against *Haemonchus contortus* ("H"), *Trichostrongylus colubriformis* ("T"), and Ostertagia spp. ("O")
Test 7: Evaluation of Three Salts of 1,5-bis(4-trifluromethyl)phenyl)-3-formazancarbonitrile

| | | | | | | | | | | | | | |
|---|---|---|---|---|---|---|---|---|---|---|---|---|---|
| Cmpd 11, Form L | 8.13 | 100 | 100 | 46 | 13 | 0 | 59 | 0 | 0 | 0 | 100 | 100 | — |
| Cmpd 11, Form L | 8.13 | 100 | 0 | 392 | 34 | 0 | 426 | 0 | 2000 | 719 | 100 | 0 | 0 |
| Cmpd 9, Form M | 6.70 | 100 | 0 | 217 | 20 | 5 | 242 | 0 | 49 | 0 | 100 | 61 | — |
| Cmpd 9, Form M | 6.70 | 100 | 100 | 8 | 0 | 0 | 8 | 0 | 2 | 0 | 100 | 98 | — |
| Cmpd 12, Form N | 8.85 | 100 | 100 | 71 | 11 | 0 | 82 | 0 | 12 | 927 | 100 | 91 | 0 |
| Cmpd 12, Form N | 8.85 | 100 | 0 | 21 | 0 | 0 | 21 | 0 | 1155 | 927 | 100 | 0 | 0 |
| VC | 0 | 3 | — | 0 | 0 | 0 | 0 | 196 | 127 | 610 | 0 | 0 | 0 |

Cmpd 9 = 1,5-bis(4-trifluromethyl)phenyl)-3-formazancarbonitrile tetraethylammonium salt
Cmpd 11 = 1,5-bis(4-trifluromethyl)phenyl)-3-formazancarbonitrile tetra-n-butylammonium salt
Cmpd 12 = 1,5-bis(4-trifluromethyl)phenyl)-3-formazancarbonitrile tetra-n-pentylammonium salt
*Average of 3 days sampling
[1]At necropsy 7 days following treatment

TABLE 7B

Percent Insecticidal Activity Against *Phormia regina* ("L") and *Stomoxys calcitrans* ("A")
Following 24 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|---|---|---|---|---|
| Cmpd 11, Form L | 8.13 | 0 | 10 | 0 | 30 | 60 | 50 | 100 | 80 | 0 | 20 | 0 | 20 | 0 | 20 | 0 | 10 |
| Cmpd 11, Form L | 8.13 | 0 | 20 | 0 | 10 | 100 | 100 | 100 | 70 | 0 | 30 | 0 | 10 | 0 | 10 | 0 | 0 |
| Cmpd 9, Form M | 6.70 | 0 | 20 | 0 | 20 | 100 | 90 | 90 | 60 | 0 | 40 | 0 | 0 | 0 | 0 | 0 | 20 |
| Cmpd 9, Form M | 6.70 | 0 | 20 | 0 | 0 | 100 | 40 | 100 | 60 | 0 | 20 | 0 | 0 | 0 | 10 | 0 | 10 |
| Cmpd 12, Form N | 8.85 | 0 | 10 | 0 | 10 | 100 | 90 | 100 | 100 | 90 | 70 | 0 | 20 | 0 | 10 | 0 | 10 |
| Cmpd 12, Form N | 8.85 | 0 | 20 | 0 | 20 | 100 | 70 | 100 | 100 | 0 | 10 | 0 | 0 | 0 | 10 | 0 | 10 |
| VC | 0 | 0 | 20 | 0 | 0 | 0 | 30 | 0 | 30 | 0 | 20 | 0 | 20 | 0 | 20 | 0 | 20 |

TABLE 7C

Percent Insecticidal Activity Against *Phormia regina* ("L") and *Stomoxys calcitrans* ("A")
Following 48 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|---|---|---|---|---|
| Cmpd 11, Form L | 8.13 | 0 | 20 | 0 | 50 | 90 | 100 | 100 | 100 | 0 | 100 | 0 | 30 | 0 | 40 | 0 | 20 |
| Cmpd 11, Form L | 8.13 | 0 | 30 | 0 | 20 | 100 | 100 | 100 | 100 | 10 | 70 | 0 | 20 | 0 | 20 | 0 | 20 |
| Cmpd 9, Form M | 6.70 | 0 | 30 | 0 | 70 | 100 | 100 | 100 | 100 | 0 | 50 | 0 | 0 | 0 | 20 | 0 | 40 |
| Cmpd 9, Form M | 6.70 | 0 | 30 | 0 | 30 | 100 | 100 | 100 | 100 | 10 | 70 | 0 | 50 | 0 | 10 | 0 | 10 |
| Cmpd 12, Form N | 8.85 | 0 | 20 | 0 | 10 | 100 | 100 | 100 | 100 | 100 | 100 | 0 | 90 | 0 | 50 | 0 | 30 |
| Cmpd 12, Form N | 8.85 | 0 | 30 | 0 | 20 | 100 | 100 | 100 | 100 | 40 | 70 | 0 | 0 | 0 | 30 | 0 | 10 |
| VC | 0 | 0 | 30 | 0 | 0 | 0 | 40 | 0 | 30 | 0 | 20 | 0 | 30 | 0 | 20 | 0 | 0 |

TABLE 8A

Activity Against *Haemonchus contortus* ("H"), Trichostrongylus spp. ("T"),
and Ostertagia spp. ("O")
Test 8: Evaluation of 1,5-bis(4-trifluoromethyl)phenyl)-3-formazancarbonitrile
trimethyloctadecylammonium salt Administered as an Oral Drench, Formulation K

| | | Worm Eggs Per Gram of Feces (EPG) | | | | | | | | | | |
|---|---|---|---|---|---|---|---|---|---|---|---|---|
| | | | | Days Following Treatment | | | | | | | | |
| | Dose | Pre* | | 1 | | 2 | | 3 | | 4 | | 5–7* |
| Treatment | mg/kg | H | T | H | T | H | T | H | T | H | T | H | T |
| Treated | 9.0 | 3800 | 567 | 3300 | 800 | 200 | 300 | 0 | 300 | 0 | 400 | 0 | 400 |
| Treated | 9.0 | 900 | 0 | 900 | 0 | 900 | 0 | 200 | 0 | 0 | 0 | 0 | 0 |
| VC | 0 | 400 | 0 | 300 | 0 | 400 | 0 | 500 | 0 | 500 | 0 | 350 | 0 |

| | Dose | % Worm Egg Reduction | | Daily Worm Passage | | | | Total Worm Counts | | | % Worm Reduction | | |
|---|---|---|---|---|---|---|---|---|---|---|---|---|---|
| Treatment | mg/kg | H | T | 1 H | 2 H | 3 H | 4 H | H | T | O | H | T | O |
| Treated | 9.0 | 100 | 29.5 | 344 | 41 | 0 | 0 | 0 | 48 | 33 | 100 | — | — |
| Treated | 9.0 | 100 | — | 215 | 26 | 0 | 0 | 0 | 5 | 26 | 100 | — | — |
| VC | 0 | 0 | — | 0 | 0 | 0 | 0 | 119 | 14 | 11 | — | — | — |

*Average of 3 days sampling

TABLE 8B

Percent Insecticidal Activity Against *Phormia regina* ("L") and *Stomoxys calcitrans* ("A")
Following 24 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A |
|---|---|---|---|---|---|---|---|---|---|---|---|---|---|---|---|---|---|---|---|
| Treated | 9.0 | 0 | 10 | 0 | 0 | 100 | 40 | 100 | 30 | 0 | 20 | 0 | 0 | 0 | 10 | 0 | 0 | 0 | 10 |

TABLE 8B-continued

Percent Insecticidal Activity Against *Phormia regina* ("L") and *Stomoxys calcitrans* ("A")
Following 24 hr in vitro Exposure

| Treatment | Dose mg/kg | Day 0 L | A | 30 Min L | A | 5 Hr L | A | Day 1 L | A | Day 2 L | A | Day 3 L | A | Day 4 L | A | Day 5 L | A | Day 6 L | A |
|---|---|---|---|---|---|---|---|---|---|---|---|---|---|---|---|---|---|---|---|
| Treated | 9.0 | 0 | 0 | 0 | 0 | 100 | 10 | 100 | 70 | 100 | 70 | 0 | 20 | 0 | 10 | 0 | 0 | 0 | 0 |
| VC | 0 | 0 | 0 | 10 | 0 | 10 | 0 | 40 | 0 | 20 | 0 | 20 | 0 | 0 | 0 | 10 | 0 | 20 | 0 | 20 |

TABLE 8C

Percent Insecticidal Activity Against *Phormia regina* ("L") and *Stomoxys calcitrans* ("A")
Following 48 hr in vitro Exposure

| Treatment | Dose mg/kg | Day 0 L | A | 30 Min L | A | 5 Hr L | A | Day 1 L | A | Day 2 L | A | Day 3 L | A | Day 4 L | A | Day 5 L | A | Day 6 L | A |
|---|---|---|---|---|---|---|---|---|---|---|---|---|---|---|---|---|---|---|---|
| Treated | 9.0 | 0 | 20 | 0 | 0 | 100 | 100 | 100 | 100 | 0 | 70 | 0 | 10 | 0 | 20 | 0 | 10 | 0 | 10 |
| Treated | 9.0 | 0 | 10 | 0 | 0 | 100 | 100 | 100 | 100 | 100 | 100 | 0 | 90 | 0 | 50 | 0 | 20 | 0 | 0 |
| VC | 0 | 0 | 20 | 0 | 10 | 0 | 20 | 0 | 30 | 0 | 20 | 0 | 10 | 0 | 30 | 0 | 20 | 0 | 20 |

TABLE 9A

Activity Against *Haemonchus contortus* ("H"), *Trichostrongylus* spp. ("T"),
and *Ostertagia* spp. ("O")
Test 9: Evaluation of 1,5-bis(4-trifluoromethyl)phenyl)-3-formazancarbonitrile
Administered Daily for Seven Days at 1.0 mg/kg/day, by Intraruminal Injection, Formulation F

| | Worm Eggs Per Gram of Feces (EPG) | | | | | | | | | | | | | |
|---|---|---|---|---|---|---|---|---|---|---|---|---|---|---|
| | Pre* | | 1 | | 2 | | 3 | | 4 | | 5-7* | | 8-10 | |
| Treatment | H | T | H | T | H | T | H | T | H | T | H | T | H | T |
| Treated | 1050 | 200 | 1000 | 100 | 400 | 100 | 300 | 0 | 0 | 200 | 0 | 0 | 0 | 0 |
| Treated | 500 | 150 | 300 | 100 | 200 | 100 | 0 | 200 | 0 | 0 | 0 | 100 | 0 | 0 |
| VC | 400 | 150 | 400 | 200 | 300 | 100 | 400 | 100 | 500 | 100 | 367 | 100 | 360 | 200 |

| | % Worm Egg Reduction | | Daily Worm Passage | | | | Total Worm Counts[1] | | | % Worm Reduction | | |
|---|---|---|---|---|---|---|---|---|---|---|---|---|
| Treatment | H | T | 1 H | 2 H | 3 H | Total | H | T | O | H | T | O |
| Treated | 100 | 100 | 6 | 67 | 8 | 81 | 11** | 0 | 46 | 86.4 | 100 | 0 |
| Treated | 100 | 100 | 0 | 41 | 3 | 44 | 0 | 17 | 46 | 100 | 10 | 0 |
| VC | 12.5 | 33.3 | 0 | 0 | 0 | 0 | 66 | 19 | 27 | — | — | — |

*Average of 3 days sampling
**10 males, 1 female

TABLE 9B

Percent Insecticidal Activity Against *Phormia regina* ("L") and *Stomoxys calcitrans* ("A")
Following 24 hr in vitro Exposure

| Treatment | Day 0 L | A | Day 1 L | A | Day 2 L | A | Day 3 L | A | Day 4 L | A | Day 5 L | A | Day 6 L | A | Day 7 L | A | Day 8 L | A | Day 9 L | A | Day 10 L | A |
|---|---|---|---|---|---|---|---|---|---|---|---|---|---|---|---|---|---|---|---|---|---|---|
| Treated | 0 | 0 | 25 | 10 | 10 | 0 | 85 | 0 | 100 | 10 | 60 | 10 | 75 | 10 | 60 | 30 | 0 | 20 | 0 | 0 | 0 | 0 |
| Treated | 0 | 10 | 60 | 10 | 90 | 0 | 10 | 0 | 100 | 20 | 75 | 0 | 75 | 0 | 100 | 60 | 0 | 30 | 0 | 0 | 0 | 0 |
| VC | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE 9C

Percent Insecticidal Activity Against *Phormia regina* ("L") and *Stomoxys calcitrans* ("A")
Following 48 hr in vitro Exposure

| Treatment | Day 0 L | A | Day 1 L | A | Day 2 L | A | Day 3 L | A | Day 4 L | A | Day 5 L | A | Day 6 L | A | Day 7 L | A | Day 8 L | A | Day 9 L | A | Day 10 L | A |
|---|---|---|---|---|---|---|---|---|---|---|---|---|---|---|---|---|---|---|---|---|---|---|
| Treated | 0 | 10 | 100 | 80 | 100 | 60 | 100 | 100 | 100 | 100 | 100 | 20 | 100 | 100 | 100 | 80 | 0 | 20 | 0 | 0 | 0 | 0 |
| Treated | 0 | 10 | 100 | 80 | 100 | 100 | 75 | 80 | 100 | 100 | 100 | 50 | 100 | 80 | 100 | 80 | 0 | 60 | 0 | 10 | 0 | 0 |
| VC | 0 | 0 | 0 | 10 | 10 | 10 | 0 | 20 | 0 | 20 | 0 | 0 | 0 | 0 | 0 | 0 | 0 | 0 | 0 | 0 | 0 | 0 |

TABLE 10A

Percent Insecticidal Activity Against *Phormia regina* ("L") and *Stomoxys calcitrans* ("A")
Following 24 hr in vitro Exposure
Test 10: Evaluation of 1,5-bis(4-trifluoromethyl)phenyl)-3-formazancarbonitrile
tetra-n-butylammonium salt in Blood From Non-Wormy Sheep Treated With Formulation G

| Treatment | Dose mg/kg | Day 0 L | A | 30 Min L | A | 5 Hr L | A | Day 1 L | A | Day 2 L | A | Day 3 L | A | Day 4 L | A | Day 5 L | A | Day 6 L | A |
|---|---|---|---|---|---|---|---|---|---|---|---|---|---|---|---|---|---|---|---|
| Treated | 8.13 | 0 | 0 | 0 | 0 | 100 | 40 | 100 | 30 | 0 | 10 | 0 | 10 | 0 | 0 | 0 | 10 | 0 | 0 |

TABLE 10A-continued

Percent Insecticidal Activity Against *Phormia regina* ("L") and *Stomoxys calcitrans* ("A")
Following 24 hr in vitro Exposure
Test 10: Evaluation of 1,5-bis(4-trifluoromethyl)phenyl)-3-formazancarbonitrile
tetra-n-butylammonium salt in Blood From Non-Wormy Sheep Treated With Formulation G

| Treatment | Dose mg/kg | Day 0 L | A | 30 Min L | A | 5 Hr L | A | Day 1 L | A | Day 2 L | A | Day 3 L | A | Day 4 L | A | Day 5 L | A | Day 6 L | A |
|---|---|---|---|---|---|---|---|---|---|---|---|---|---|---|---|---|---|---|---|
| Treated | 8.13 | 0 | 0 | 0 | 0 | 100 | 50 | 100 | 10 | 0 | 0 | 0 | 20 | 0 | 0 | 0 | 20 | 0 | 0 |
| VC | 0 | 0 | 0 | 0 | 0 | 0 | 0 | 0 | 10 | 0 | 10 | 0 | 0 | 0 | 0 | 0 | 10 | 0 | 0 |

TABLE 10B

Percent Insecticidal Activity Against *Phormia regina* ("L") and *Stomoxys calcitrans* ("A")
Following 48 hr in vitro Exposure

| Treatment | Dose mg/kg | Day 0 L | A | 30 Min L | A | 5 Hr L | A | Day 1 L | A | Day 2 L | A | Day 3 L | A | Day 4 L | A | Day 5 L | A | Day 6 L | A |
|---|---|---|---|---|---|---|---|---|---|---|---|---|---|---|---|---|---|---|---|
| Treated | 8.13 | 0 | 0 | 0 | 0 | 100 | 100 | 100 | 100 | 0 | 10 | 0 | 0 | 0 | 0 | 0 | 10 | 0 | 0 |
| Treated | 8.13 | 0 | 0 | 0 | 0 | 100 | 100 | 100 | 100 | 0 | 0 | 0 | 20 | 0 | 0 | 0 | 20 | 0 | 10 |
| VC | 0 | 0 | 0 | 0 | 0 | 0 | 10 | 0 | 20 | 0 | 10 | 0 | 0 | 0 | 10 | 0 | 10 | 0 | 0 |

TESTS AGAINST *FASCIOLA HEPATICA* IN SHEEP (Tests 11-13 and Tables 11-13)

The present invention was also evaluated for the control of *Fasciola hepatica* (liver fluke) in sheep. Sheep approximately twelve months old were each experimentally infected by a single intraruminal injection of 100 metacercariae of *Fasciola hepatica*. The sheep were alloted to treatment or control groups, two or three per group, and given either the test compound or the vehicle. Treated animals received the test compound at each of day 3, 3 weeks, and 12 weeks after fluke infection.

Administration of the test compound was by a single intraruminal injection. The control group received a single intraruminal injection of the vehicle at 12 weeks.

Blood samples were collected prior to treatment and daily for five days after the 3 week and 12 week treatment. These samples were analyzed for activity against *Phormia regina* and *Stomoxys calcitrans* according to the procedure described above. At 14 weeks after fluke infection, all sheep were euthanized and analyzed for total worm counts.

The results of several tests are set forth in the following tables.

TABLE 11A

Percent Insecticidal Activity Against *Phormia regina* ("L") and *Stomoxys calcitrans* ("A") Following 24 hr in vitro Exposure
Test 11: Evaluation of 1,5-bis(4-(trifluoromethyl)phenyl)-3-formazancarbonitrile, PEG 200 Formulation

| Treatment[1] | Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|---|
| Treated | 5 | 0 | 0 | 100 | 90 | 75 | 40 | 0 | 0 | 0 | 0 | 0 | 0 |
| Treated | 5 | 0 | 0 | 100 | 80 | 75 | 40 | 0 | 0 | 10 | 0 | 0 | 0 |
| Treated | 10 | 0 | 0 | 100 | 100 | 0 | 10 | 0 | 0 | 0 | 0 | 0 | 0 |
| Treated | 10 | 0 | 10 | 100 | 100 | 0 | 0 | 0 | 0 | 0 | 0 | 0 | 10 |
| VC | 0 | 0 | 0 | 0 | 0 | 0 | 0 | 0 | 0 | 0 | 0 | 0 | 0 |

TABLE 11B

Percent Insecticidal Activity Against *Phormia regina* ("L") and *Stomoxys calcitrans* ("A")
Following 48 hr in vitro Exposure

| Treatment[1] | Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|---|
| Treated | 5 | 0 | 0 | 100 | 100 | 100 | 100 | 0 | 60 | 0 | 50 | 0 | 40 |
| Treated | 5 | 0 | 0 | 100 | 100 | 100 | 100 | 25 | 80 | 0 | 50 | 0 | 20 |
| Treated | 10 | 0 | 0 | 100 | 100 | 75 | 100 | 0 | 30 | 0 | 20 | 0 | 40 |
| Treated | 10 | 0 | 20 | 100 | 100 | 75 | 100 | 0 | 90 | 0 | 60 | 0 | 10 |
| VC | 0 | 0 | 10 | 0 | 20 | 0 | 20 | 0 | 20 | 0 | 20 | 0 | 20 |

[1] 3 weeks after experimental fluke infection

TABLE 11C

Percent Insecticidal Activity Against *Phormia regina* ("L") and *Stomoxys calcitrans* ("A") Following 24 hr in vitro Exposure

| Treatment[1] | Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|---|
| Treated | 5 | 0 | 0 | 100 | 60 | 100 | 40 | 100 | 70 | 100 | 20 | 100 | 0 |
| Treated | 5 | 0 | 0 | 100 | 10 | 100 | 10 | 0 | 20 | 0 | 0 | 0 | 0 |
| Treated | 10 | 0 | 0 | 100 | 70 | 100 | 40 | 100 | 10 | 0 | 10 | 0 | 0 |
| Treated | 10 | 0 | 0 | 100 | 60 | 100 | 20 | 0 | 30 | 0 | 0 | 0 | 0 |
| VC | 0 | 0 | 0 | 0 | 20 | 0 | 0 | 0 | 20 | 0 | 0 | 0 | 0 |

TABLE 11C-continued

Percent Insecticidal Activity Against *Phormia regina* ("L") and *Stomoxys calcitrans* ("A") Following 24 hr in vitro Exposure

| Treatment[1] | Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|---|
| VC | 0 | 0 | 0 | 0 | 10 | 0 | 0 | 0 | 0 | 0 | 0 | 0 | 0 |

TABLE 11D

Percent Insecticidal Activity Against *Phormia regina* ("L") and *Stomoxys calcitrans* ("A") Following 48 hr in vitro Exposure

| Treatment[1] | Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|---|
| Treated | 5 | 0 | 0 | 100 | 100 | 100 | 100 | 100 | 100 | 100 | 90 | 100 | 100 |
| Treated | 5 | 0 | 10 | 100 | 100 | 100 | 90 | 0 | 0 | 0 | 10 | 0 | 0 |
| Treated | 10 | 0 | 0 | 100 | 90 | 100 | 100 | 100 | 30 | 10 | 30 | 0 | 0 |
| Treated | 10 | 0 | 0 | 100 | 100 | 100 | 100 | 0 | 30 | 0 | 10 | 0 | 0 |
| VC | 0 | 0 | 0 | 0 | 20 | 0 | 0 | 0 | 20 | 0 | 0 | 0 | 0 |
| VC | 0 | 0 | 10 | 0 | 10 | 0 | 0 | 0 | 0 | 0 | 20 | 0 | 0 |

[1] 12 weeks after experimental fluke infection

TABLE 11E

Activity Against *Fasciola hepatica*

| Dose (mg/kg) | Dose PI | Egg Fecal | % Liver Damage | Total Worm Counts[1] BD | LD | Total | Comments |
|---|---|---|---|---|---|---|---|
| 10 | 3 days | — | 20 | 0 | 16 | 16 | Muddy appearance of bile sac content. |
| 10 | 3 days | + | 90 | 6 | 13 | 19 | Liver 25% consolidated; rest granulated. |
| 5 | 3 wks | — | 8 | 0 | 10 | 10 | Little damage to liver; consolidated. |
| 5 | 3 wks | + | 25 | 10 | 27 | 37 | Diffused liver damage |
| 10 | 3 wks | + | 25 | 16 | 16 | 36 | Liver damage consolidated. |
| 10 | 3 wks | + | 50 | 9 | 4 | 13 | Enlarged bile duct; pus in liver ducts; liver damage consolidated. |
| 5 | 12 wks | — | 45 | 0 | 0 | 0 | 2 abscesses and 2 nodules in liver; great amt of pus and ropy excrement in liver ducts. Diffused liver damage. |
| 5 | 12 wks | — | 75 | 0 | 6 | 6 | Pus in liver ducts; dead worms; liver damage consolidated. |
| 10 | 12 wks | — | 20 | 0 | 9 | 9 | Diffused liver damage; live worms. |
| 10 | 12 wks | + | 30 | 1 | 11 | 12 | Ropy excrement; live worms in ducts of liver; consolidated liver damage. |
| 0 | | + | 25 | 9 | 16 | 25 | Liver damage diffused. |
| 0 | | + | 55 | 8 | 21 | 29 | Consolidated liver damage. |

[1] Necropsy 14 weeks after experimental fluke infection.
BD = bile duct
LD = liver ducts
PI = post infection A second test was conducted. The procedures were the same as those previously described except as follows: Formulation H was used; it was administered only twice, at 7 days and 3 weeks after fluke infection; and the animals were euthanized and total worm counts determined at 10 weeks after fluke infection. The results were as set forth in the following tables.

TABLE 12A

Percent Insecticidal Activity Against *Phormia regina* ("L") and *Stomoxys calcitrans* ("A") Following 24 hr in vitro Exposure
Test 12: Evaluation of 1,5-bis(4-(trifluoromethyl)phenyl)-3-formazancarbonitrile, Formulation H

| Treatment[1] | Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|---|
| Treated | 5 | 0 | 0 | 100 | 60 | 100 | 70 | 25 | 60 | 40 | 0 | 0 | 10 |
| Treated | 5 | 0 | 0 | 100 | 80 | 100 | 90 | 100 | 30 | 60 | 30 | 25 | 30 |
| Treated | 10 | 0 | 0 | 100 | 90 | 100 | 70 | 100 | 40 | 100 | 50 | 100 | 70 |
| Treated | 10 | 0 | 0 | 100 | 70 | 100 | 60 | 100 | 60 | 100 | 40 | 10 | 50 |
| VC | 0 | 0 | 0 | 0 | 0 | 0 | 0 | 0 | 0 | 0 | 0 | 0 | 0 |
| VC | 0 | 0 | 0 | 0 | 0 | 0 | 0 | 0 | 0 | 0 | 0 | 0 | 0 |

TABLE 12B

Percent Insecticidal Activity Against *Phormia regina* ("L") and *Stomoxys calcitrans* ("A") Following 48 hr in vitro Exposure

| Treatment[1] | Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|---|
| Treated | 5 | 0 | 0 | 100 | 100 | 100 | 100 | 100 | 100 | 100 | 80 | 0 | 20 |
| Treated | 5 | 0 | 0 | 100 | 100 | 100 | 90 | 100 | 90 | 100 | 90 | 25 | 70 |

TABLE 12B-continued

Percent Insecticidal Activity Against *Phormia regina* ("L") and *Stomoxys calcitrans* ("A")
Following 48 hr in vitro Exposure

| Treatment[1] | Dose mg/kg | Day 0 L | Day 0 A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|---|
| Treated | 10 | 0 | 0 | 100 | 100 | 100 | 100 | 100 | 90 | 100 | 90 | 100 | 100 |
| Treated | 10 | 0 | 10 | 100 | 100 | 100 | 100 | 100 | 100 | 100 | 100 | 20 | 50 |
| VC | 0 | 0 | 10 | 0 | 0 | 0 | 0 | 0 | 0 | 0 | 0 | 0 | 0 |
| VC | 0 | 0 | 0 | 0 | 0 | 0 | 0 | 0 | 0 | 0 | 0 | 0 | 0 |

[1]Blood samples taken beginning at day 7 post fluke infection

TABLE 12C

Percent Insecticidal Activity Against *Phormia regina* ("L") and *Stomoxys calcitrans* ("A")
Following 24 hr in vitro Exposure

| Treatment[1] | Dose mg/kg | Day 0 L | Day 0 A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|---|
| Treated | 5 | 0 | 0 | 100 | 90 | 100 | 90 | 100 | 70 | 10 | 20 | 0 | 0 |
| Treated | 5 | 0 | 20 | 100 | 100 | 100 | 90 | 90 | 80 | 0 | 10 | 0 | 20 |
| Treated | 5 | 0 | 10 | 100 | 80 | 100 | 100 | 100 | 100 | 100 | 80 | 100 | 80 |
| Treated | 10 | 0 | 0 | 100 | 100 | 100 | 90 | 100 | 90 | 0 | 10 | 0 | 10 |
| Treated | 10 | 0 | 0 | 100 | 100 | 100 | 80 | 100 | 90 | 90 | 40 | 80 | 40 |
| Treated | 10 | 0 | 20 | 100 | 100 | 100 | 80 | 100 | 60 | 0 | 20 | 0 | 0 |
| VC | 0 | 0 | 10 | 0 | 10 | 0 | 0 | 0 | 30 | 0 | 10 | 0 | 0 |
| VC | 0 | 0 | 20 | 0 | 20 | 0 | 10 | 0 | 10 | 0 | 0 | 0 | 0 |

TABLE 12D

Percent Insecticidal Activity Against *Phormia regina* ("L") and *Stomoxys calcitrans* ("A")
Following 48 hr in vitro Exposure

| Treatment[1] | Dose mg/kg | Day 0 L | Day 0 A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|---|
| Treated | 5 | 0 | 30 | 100 | 100 | 100 | 100 | 100 | 100 | 30 | 100 | 10 | 90 |
| Treated | 5 | 0 | 30 | 100 | 100 | 100 | 100 | 100 | 100 | 10 | 100 | 0 | 70 |
| Treated | 5 | 0 | 20 | 100 | 100 | 100 | 100 | 100 | 100 | 100 | 100 | 100 | 100 |
| Treated | 10 | 0 | 0 | 100 | 100 | 100 | 100 | 100 | 100 | 10 | 60 | 0 | 10 |
| Treated | 10 | 0 | 10 | 100 | 100 | 100 | 100 | 100 | 100 | 100 | 90 | 90 | 90 |
| Treated | 10 | 0 | 30 | 100 | 100 | 100 | 100 | 100 | 100 | 10 | 80 | 0 | 20 |
| VC | 0 | 0 | 10 | 0 | 20 | 0 | 10 | 0 | 40 | 0 | 20 | 0 | 10 |
| VC | 0 | 0 | 30 | 0 | 30 | 0 | 30 | 0 | 20 | 0 | 0 | 0 | 20 |

[1]Blood samples taken beginning at 3 weeks post fluke infection

TABLE 12E

Activity Against *Fasciola hepatica*

| Test Group | Dose (mg/kg) | Dose PI | % Liver Damage | Immature | Mature | Total |
|---|---|---|---|---|---|---|
| 1 | 5 | 7 days | 50 | 2 | 11 | 13 |
|   | 5 | 7 days | 10 | 0 | 0 | 0 |
| 2 | 10 | 7 days | 20 | 7 | 0 | 7 |
|   | 10 | 7 days | 10 | 0 | 11 | 11 |
| 3 | 5 | 3 wks | 10 | 1 | 11 | 12 |
|   | 5 | 3 wks | 10 | 0 | 10 | 10 |
|   | 5 | 3 wks | 25 | 10 | 10 | 20 |
| 4 | 10 | 3 wks | 10 | 16 | 0 | 16 |
|   | 10 | 3 wks | 10 | 10 | 0 | 10 |
|   | 10 | 3 wks | 25 | 6 | 2 | 8 |
| 5 | 0 | — | 15 | 0 | 7 | 7 |
|   | 0 | — | 10 | 1 | 12 | 13 |

[1]Necropsy 10 weeks after experimental fluke infection.
PI = post infection

A third test was conducted. The procedures were the same as previously described except as follows. Formulation R was used; it was administered at 7 days, 3 weeks, and 10 weeks after fluke infection. The results were as set forth in the following tables.

TABLE 13A

Data on Liver Damage and Number of Flukes Found at Necropsy
Test 13: Evaluation of 1,5-bis(4-(trifluoromethyl)phenyl)-3-formazancarbonitrile trimethyloctadecylammonium salt, at 36 mg/kg, Formulation R

| Dose (mg/kg) | Dose PI | % Liver Damage | Immature | Mature | Total | Fecal Sample |
|---|---|---|---|---|---|---|
| 36 | 7 days | 50 | 22 | 3 | 25 | — |
| 36 | 7 days | 35 | 11 | 39 | 50 | + |
| 36 | 7 days | 40 | 12 | 0 | 12 | — |
| 36 | 3 wks | 75 | 18 | 26 | 44 | — |
| 36 | 3 wks | 40 | 15 | 14 | 29 | — |
| 36 | 3 wks | 20 | 4 | 79 | 83 | + |
| 36 | 10 wks | 15 | 0 | 0 | 0 | — |
| 36 | 10 wks | 75 | 13 | 0 | 13 | — |
| 36 | 10 wks | 20 | 0 | 16 | 16 | — |
| VC | 0 | 65 | 20 | 19 | 39 | — |
| VC | 0 | 40 | 0 | 31 | 31 | — |
| VC | 0 | 90 | 19 | 1 | 20 | — |

[1]Necropsy 10 weeks after experimental fluke infection.
PI = post infection

TABLE 13B

Percent Insecticidal Activity Against *Phormia regina* ("L") and *Stomoxys calcitrans* ("A") Following 24 hr in vitro Exposure (7 Days P.I.)

| Dose mg/kg | Day 0 L | Day 0 A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|
| 36 | 0 | 0 | 100 | 100 | 75 | 70 | 0 | 20 | 0 | 10 | 0 | 20 |

TABLE 13B-continued

Percent Insecticidal Activity Against *Phormia regina* ("L")
and *Stomoxys calcitrans* ("A") Following 24 hr
in vitro Exposure (7 Days P.I.)

| Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|
| 36 | 0 | 0 | 100 | 90 | 0 | 0 | 0 | 20 | 0 | 10 | 0 | 20 |
| 36 | 0 | 0 | 100 | 90 | 100 | 70 | 0 | 0 | 0 | 30 | 0 | 30 |

TABLE 13C

Percent Insecticidal Activity Against *Phormia regina* ("L")
and *Stomoxys calcitrans* ("A") Following 48 hr
in vitro Exposure (7 Days P.I.)

| Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|
| 36 | 0 | 30 | 100 | 100 | 90 | 100 | 0 | 50 | 0 | 30 | 0 | 20 |
| 36 | 0 | 10 | 100 | 100 | 0 | 70 | 0 | 20 | 0 | 50 | 0 | 20 |
| 36 | 0 | 0 | 100 | 100 | 100 | 100 | 0 | 60 | 0 | 30 | 0 | 40 |

TABLE 13D

Percent Insecticidal Activity Against *Phormia regina* ("L")
and *Stomoxys calcitrans* ("A") Following 24 hr
in vitro Exposure (3 Wks P.I.)

| Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|
| 36 | 0 | 0 | 100 | 100 | 0 | 0 | 10 | 0 | 20 | 0 | 0 | 0 |
| 36 | 10 | 0 | 100 | 100 | 10 | 0 | 10 | 0 | 10 | 0 | 0 | 0 |
| 36 | 0 | 0 | 40 | 90 | 20 | 100 | 0 | 0 | 10 | 0 | 0 | 0 |

TABLE 13E

Percent Insecticidal Activity Against *Phormia regina* ("L")
and *Stomoxys calcitrans* ("A") Following 24 hr
in vitro Exposure (3 Wks P.I.)

| Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|
| 36 | 20 | 0 | 100 | 100 | 60 | 0 | 20 | 0 | 30 | 0 | 20 | 0 |
| 36 | 10 | 0 | 100 | 100 | 10 | 0 | 40 | 0 | 20 | 0 | 20 | 0 |
| 36 | 0 | 0 | 100 | 100 | 100 | 100 | 10 | 0 | 30 | 0 | 10 | 0 |

TABLE 13F

Percent Insecticidal Activity Against *Phormia regina* ("L")
and *Stomoxys calcitrans* ("A") Following 24 hr
in vitro Exposure (10 Wks P.I.)

| Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|
| 36 | 0 | 10 | 100 | 100 | 20 | 20 | 0 | 0 | 0 | 20 | 0 | 20 |
| 36 | 0 | 0 | 100 | 90 | 0 | 30 | 0 | 0 | 0 | 10 | 0 | 10 |
| 36 | 0 | 10 | 100 | 80 | 0 | 10 | 0 | 0 | 0 | 30 | 0 | 10 |
| 0 (VC) | 0 | 20 | 0 | 10 | 0 | 10 | 0 | 10 | 0 | 10 | 0 | 20 |
| 0 (VC) | 0 | 20 | 0 | 20 | 0 | 20 | 0 | 10 | 0 | 10 | 0 | 30 |
| 0 (VC) | 0 | 10 | 0 | 30 | 0 | 0 | 0 | 30 | 0 | 10 | 0 | 20 |

TABLE 13G

Percent Insecticidal Activity Against *Phormia regina* ("L") and *Stomoxys calcitrans* ("A") Following 48 hr in vitro Exposure (10 Wks P.I.)

| Dose mg/kg | Day 0 L | A | Day 1 L | A | Day 2 L | A | Day 3 L | A | Day 4 L | A | Day 5 L | A |
|---|---|---|---|---|---|---|---|---|---|---|---|---|
| 36 | 0 | 30 | 100 | 100 | 100 | 90 | 0 | 70 | 0 | 30 | 0 | 40 |
| 36 | 0 | 10 | 100 | 100 | 0 | 60 | 0 | 0 | 0 | 20 | 0 | 10 |
| 36 | 0 | 10 | 100 | 100 | 60 | 100 | 0 | 10 | 0 | 30 | 0 | 10 |
| 0 (VC) | 0 | 30 | 0 | 10 | 0 | 50 | 0 | 40 | 0 | 20 | 0 | 30 |
| 0 (VC) | 0 | 30 | 0 | 30 | 0 | 20 | 0 | 20 | 0 | 20 | 0 | 70 |
| 0 (VC) | 0 | 30 | 0 | 30 | 0 | 20 | 0 | 50 | 0 | 10 | 0 | 30 |

TESTS IN CATTLE (Tests 14–25 and Tables 14–25)

Numerous evaluations were conducted in cattle generally averaging about 300 kg in weight. In Tests 14–19, there was no helminth infection. Blood samples were collected via the jugular vein at multiple times, typically the following: prior to compound administration, at 30 minutes, 5 hours and 24 hours after compound administration, and daily thereafter up to 12 days after compound administration. These blood samples were evaluated for control of *Phormia regina* and *Stomoxys calcitrans* by the test procedure described above.

In Tests 20–25, the compound administration and blood sampling were as described above, but the cattle were infected with *Ostertagia ostertagi*, and the cattle were additionally evaluated for control of this species. This evaluation was made by determining the number of worm eggs/gram of feces, both prior to compound administration and daily after compound administration. Those animals exhibiting greater than 75 percent reduction in eggs/gram of feces were euthanized and total worm counts determined on necropsy and compared to nontreated controls.

Results are set forth in the following tables.

TABLE 14A

Percent Insecticidal Activity Against *Phormia regina* ("L") and *Stomoxys calcitrans* ("A")
Following 24 hr in vitro Exposure
Test 14: Evaluation of 1,5-bis(4-(trifluoromethyl)phenyl)-3-formazancarbonitrile
In Cattle, Administered Subcutaneously Using Formulations C, D, and E

| Treatment[1] | Dose mg/kg | Day 0 L | A | 30 Min L | A | 5 Hr L | A | Day 1 L | A | Day 2 L | A | Day 3 L | A | Day 4 L | A | Day 5 L | A | Day 6 L | A |
|---|---|---|---|---|---|---|---|---|---|---|---|---|---|---|---|---|---|---|---|
| Formulation C | 10 | 0 | 0 | 0 | 0 | 0 | 10 | 0 | 0 | 0 | 10 | 0 | 20 | 0 | 0 | 0 | 0 | 0 | 0 |
| Formulation C | 10 | 0 | 0 | 0 | 0 | 0 | 20 | 0 | 0 | 0 | 10 | 0 | 20 | 0 | 0 | 0 | 0 | 0 | 0 |
| Formulation D | 10 | 0 | 0 | 0 | 0 | 0 | 20 | 0 | 0 | 0 | 0 | 0 | 10 | 0 | 20 | 0 | 10 | 0 | 14 | 0 | 24 |
| Formulation D | 10 | 0 | 0 | 0 | 0 | 0 | 10 | 0 | 0 | 0 | 0 | 0 | 0 | 0 | 20 | 0 | 0 | 0 | 0 | 0 | 0 |
| Formulation E | 10 | 0 | 0 | 0 | 0 | 0 | 0 | 0 | 0 | 0 | 0 | 0 | 20 | 0 | 0 | 0 | 0 | 0 | 0 | 0 | 0 |
| Formulation E | 10 | 0 | 0 | 0 | 0 | 0 | 0 | 0 | 0 | 0 | 0 | 0 | 10 | 0 | 10 | 0 | 0 | 0 | 0 | 0 | 0 |
| Vehicle of Form C | — | 0 | 0 | 0 | 0 | 0 | 0 | 0 | 0 | 0 | 10 | 0 | 0 | 0 | 0 | 0 | 0 | 0 | 0 |

TABLE 14A-continued

Percent Insecticidal Activity Against *Phormia regina* ("L") and *Stomoxys calcitrans* ("A")
Following 24 hr in vitro Exposure
Test 14: Evaluation of 1,5-bis(4-(trifluoromethyl)phenyl)-3-formazancarbonitrile
In Cattle, Administered Subcutaneously Using Formulations C, D, and E

| Treatment[1] | Dose mg/kg | Day 0 L | A | 30 Min L | A | 5 Hr L | A | Day 1 L | A | Day 2 L | A | Day 3 L | A | Day 4 L | A | Day 5 L | A | Day 6 L | A |
|---|---|---|---|---|---|---|---|---|---|---|---|---|---|---|---|---|---|---|---|
| Vehicle of Form D | — | 0 | 10 | 0 | 0 | 0 | 10 | 0 | 0 | 0 | 10 | 0 | 10 | 0 | 20 | 0 | 4 | 0 | 0 |
| Vehicle of Form E | — | 0 | 0 | 0 | 0 | 0 | 0 | 0 | 0 | 0 | 0 | 0 | 0 | 0 | 0 | 0 | 14 | 0 | 0 |

[1] Single subcutaneous dose of 10 mg/kg in left upper neck in front of shoulder.

TABLE 15A

Percent Insecticidal Activity Against *Phormia regina* ("L") and *Stomoxys calcitrans* ("A")
Following 24 hr in vitro Exposure
Test 15: Evaluation of 1,5-bis(4-(trifluoromethyl)phenyl)-3-formazancarbonitrile
In Cattle, Administered Intraruminally Using Formulation F

| Treatment | Dose mg/kg | Day 0 L | A | 30 Min L | A | 5 Hr L | A | Day 1 L | A | Day 2 L | A | Day 3 L | A | Day 4 L | A | Day 6 L | A |
|---|---|---|---|---|---|---|---|---|---|---|---|---|---|---|---|---|---|
| Formulation F | 10 | 0 | 0 | 0 | 20 | 100 | 30 | 100 | 80 | 100 | 20 | 0 | 40 | 0 | 50 | 0 | 10 |
| Formulation F | 10 | 0 | 0 | 0 | 20 | 100 | 30 | 100 | 90 | 75 | 50 | 0 | 30 | 0 | 0 | 0 | 10 |
| VC | 0 | 0 | 0 | 0 | 0 | 0 | 0 | 0 | 0 | 0 | 10 | 0 | 10 | 0 | 0 | 0 | 0 |

TABLE 15B

Percent Insecticidal Activity Against *Phormia regina* ("L") and *Stomoxys calcitrans* ("A")
Following 48 hr in vitro Exposure

| Treatment | Dose mg/kg | Day 0 L | A | 30 Min L | A | 5 Hr L | A | Day 1 L | A | Day 2 L | A | Day 3 L | A | Day 4 L | A | Day 6 L | A |
|---|---|---|---|---|---|---|---|---|---|---|---|---|---|---|---|---|---|
| Formulation F | 10 | 0 | 0 | 0 | 20 | 100 | 100 | 100 | 100 | 100 | 100 | 0 | 40 | 0 | 50 | 0 | 40 |
| Formulation F | 10 | 0 | 0 | 0 | 20 | 100 | 100 | 100 | 100 | 100 | 90 | 0 | 30 | 0 | 0 | 0 | 20 |
| VC | 0 | 0 | 0 | 0 | 0 | 0 | 0 | 0 | 0 | 0 | 10 | 0 | 10 | 0 | 0 | 0 | 0 |

TABLE 16A

Percent Insecticidal Activity Against *Phormia regina* ("L") and *Stomoxys calcitrans* ("A")
Following 24 hr in vitro Exposure
Test 16: Evaluation of 1,5-bis(4-(trifluoromethyl)phenyl)-3-formazancarbonitrile
tetra-n-butylammonium salt In Cattle Administered Intraruminally Using Formulation G

| Treatment | Dose mg/kg | Day 0 L | A | 30 Min L | A | 5 Hr L | A | Day 1 L | A | Day 2 L | A | Day 3 L | A | Day 4 L | A | Day 5 L | A |
|---|---|---|---|---|---|---|---|---|---|---|---|---|---|---|---|---|---|
| Formulation G | 16.26 | 0 | 0 | 0 | 0 | 90 | 60 | 100 | 40 | 10 | 10 | 0 | 0 | 0 | 20 | 0 | 0 |
| Formulation G | 16.26 | 0 | 20 | 0 | 0 | 40 | 0 | 100 | 30 | 0 | 10 | 0 | 0 | 0 | 10 | 0 | 20 |
| VC | 0 | 0 | 0 | 0 | 0 | 0 | 0 | 0 | 0 | 0 | 0 | 0 | 0 | 0 | 20 | 0 | 0 |

TABLE 16B

Percent Insecticidal Activity Against *Phormia regina* ("L") and *Stomoxys calcitrans* ("A")
Following 48 hr in vitro Exposure

| Treatment | Dose mg/kg | Day 0 L | A | 30 Min L | A | 5 Hr L | A | Day 1 L | A | Day 2 L | A | Day 3 L | A | Day 4 L | A | Day 5 L | A |
|---|---|---|---|---|---|---|---|---|---|---|---|---|---|---|---|---|---|
| Formulation G | 16.26 | 0 | 0 | 0 | 0 | 100 | 90 | 100 | 100 | 0 | 30 | 0 | 0 | 0 | 10 | 0 | 10 |
| Formulation G | 16.26 | 0 | 20 | 0 | 10 | 100 | 80 | 100 | 90 | 10 | 30 | 30 | 0 | 0 | 0 | 0 | 10 |
| VC | 0 | 0 | 0 | 0 | 0 | 0 | 10 | 0 | 0 | 0 | 0 | 0 | 0 | 0 | 0 | 0 | 0 |

TABLE 17A

Percent Insecticidal Activity Against *Phormia regina* ("L") and *Stomoxys calcitrans* ("A")
Following 24 hr in vitro Exposure
Test 17: Evaluation of Salts of 1,5-bis(4-(trifluoromethyl)phenyl)-3-formazancarbonitrile
In Cattle Administered Intraruminally Using Formulations I, J, and K

| Treatment | Dose mg/kg | Day 0 L | A | 30 Min L | A | 5 Hr L | A | Day 1 L | A | Day 2 L | A | Day 3 L | A | Day 4 L | A | Day 5 L | A | Day 6 L | A | Day 7 L | A |
|---|---|---|---|---|---|---|---|---|---|---|---|---|---|---|---|---|---|---|---|---|---|
| Cmpd 8, Form I | 11.9 | 0 | 0 | 0 | 20 | 60 | 0 | 100 | 90 | 0 | 0 | 0 | 0 | 0 | 0 | 0 | 0 | 0 | 0 | 0 | 0 |
| Cmpd 8, Form I | 11.9 | 0 | 10 | 0 | 30 | 60 | 40 | 100 | 60 | 90 | 30 | 0 | 0 | 0 | 0 | 0 | 0 | 0 | 0 | 0 | 0 |
| Cmpd 10, Form J | 14.8 | 0 | 0 | 0 | 10 | 10 | 0 | 90 | 60 | 0 | 0 | 0 | 0 | 0 | 0 | 0 | 0 | 0 | 0 | 0 | 0 |
| Cmpd 10, Form J | 14.8 | 0 | 10 | 0 | 40 | 100 | 0 | 100 | 80 | 15 | 0 | 0 | 10 | 0 | 0 | 0 | 0 | 0 | 0 | 0 | 0 |
| Cmpd 13, Form K | 18 | 0 | 10 | 0 | 40 | 25 | 40 | 100 | 70 | 100 | 70 | 0 | 0 | 0 | 0 | 0 | 0 | 0 | 0 | 0 | 0 |
| Cmpd 13, Form K | 18 | 0 | 10 | 0 | 10 | 90 | 50 | 100 | 90 | 100 | 90 | 0 | 10 | 0 | 0 | 0 | 0 | 0 | 0 | 0 | 10 |

TABLE 17A-continued

Percent Insecticidal Activity Against *Phormia regina* ("L") and *Stomoxys calcitrans* ("A")
Following 24 hr in vitro Exposure
Test 17: Evaluation of Salts of 1,5-bis(4-(trifluoromethyl)phenyl)-3-formazancarbonitrile
In Cattle Administered Intraruminally Using Formulations I, J, and K

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A | Day 7 L | Day 7 A |
|---|---|---|---|---|---|---|---|---|---|---|---|---|---|---|---|---|---|---|---|---|---|
| Vehicle of Form I-K | 0 | 0 | 0 | 0 | 0 | 0 | 0 | 0 | 0 | 0 | 0 | 0 | 0 | 0 | 0 | 0 | 0 | 0 | 0 | 0 | 0 |

Cmpd 8 = 1,5-bis(4-(trifluoromethyl)phenyl)-3-formazancarbonitrile tetramethylammonium salt
Cmpd 10 = 1,5-bis(4-(trifluoromethyl)phenyl)-3-formazancarbonitrile tetra-n-propylammonium salt
Cmpd 13 = 1,5-bis(4-(trifluoromethyl)phenyl)-3-formazancarbonitrile trimethyloctadecylammonium salt

TABLE 17B

Percent Insecticidal Activity Against *Phormia regina* ("L") and *Stomoxys calcitrans* ("A")
Following 48 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A | Day 7 L | Day 7 A |
|---|---|---|---|---|---|---|---|---|---|---|---|---|---|---|---|---|---|---|---|---|---|
| Cmpd 8, Form I | 11.9 | 0 | 20 | 0 | 30 | 100 | 70 | 100 | 100 | 100 | 90 | 0 | 0 | 0 | 0 | 0 | 0 | 0 | 0 | 0 | 0 |
| Cmpd 8, Form I | 11.9 | 0 | 20 | 0 | 30 | 100 | 90 | 100 | 90 | 100 | 90 | 0 | 0 | 0 | 0 | 0 | 0 | 0 | 0 | 0 | 0 |
| Cmpd 10, Form J | 14.8 | 0 | 0 | 0 | 10 | 100 | 80 | 100 | 100 | 75 | 80 | 0 | 20 | 0 | 0 | 0 | 0 | 0 | 0 | 0 | 0 |
| Cmpd 10, Form J | 14.8 | 0 | 10 | 0 | 60 | 100 | 80 | 100 | 100 | 100 | 80 | 0 | 30 | 0 | 0 | 0 | 0 | 0 | 0 | 0 | 0 |
| Cmpd 13, Form K | 18 | 0 | 10 | 0 | 40 | 100 | 100 | 100 | 100 | 100 | 100 | 0 | 30 | 0 | 0 | 0 | 0 | 0 | 0 | 0 | 0 |
| Cmpd 13, Form K | 18 | 0 | 10 | 0 | 30 | 100 | 100 | 100 | 100 | 100 | 100 | 0 | 10 | 0 | 0 | 0 | 0 | 0 | 0 | 0 | 20 |
| Vehicle of Form I-K | 0 | 0 | 0 | 0 | 0 | 0 | 20 | 0 | 0 | 0 | 0 | 0 | 10 | 0 | 0 | 0 | 0 | 0 | 0 | 0 | 0 |

TABLE 18A

Percent Insecticidal Activity Against *Phormia regina* ("L") and *Stomoxys calcitrans* ("A")
Following 24 hr in vitro Exposure
Test 18: Evaluation of Sodium Salt of 1,5-bis(4-(trifluoromethyl)phenyl)-3-formazancarbonitrile (Cmpd 7)
In Cattle Administered Subcutaneously Using PEG 200 Formulation

| Treatment | Dose mg/kg | Blood Sample | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A |
|---|---|---|---|---|---|---|---|---|---|---|---|---|---|---|---|---|---|---|---|---|
| Cmpd 7 | 1.0 | WB | 0 | 0 | 0 | 0 | 0 | 0 | 0 | 0 | 0 | 0 | 0 | 0 | 0 | 10 | 0 | 0 | 0 | 0 |
| Cmpd 7 |  | S | 0 | 0 | 0 | 0 | 0 | 0 | 0 | 10 | 0 | 10 | 0 | 0 | 0 | 0 | 0 | 0 | 0 | 0 |
| Cmpd 7 | 1.0 | WB | 0 | 0 | 0 | 10 | 0 | 0 | 0 | 0 | 0 | 0 | 0 | 0 | 0 | 0 | 0 | 10 | 0 | 10 |
| Cmpd 7 |  | S | 0 | 0 | 0 | 10 | 0 | 0 | 0 | 10 | 0 | 0 | 0 | 0 | 0 | 0 | 0 | 10 | 0 | 0 |
| Cmpd 7 | 2.0 | WB | 0 | 0 | 0 | 0 | 0 | 0 | 0 | 10 | 0 | 0 | 0 | 0 | 0 | 10 | 0 | 0 | 0 | 0 |
| Cmpd 7 |  | S | 0 | 0 | 0 | 10 | 0 | 0 | 0 | 0 | 0 | 0 | 0 | 0 | 0 | 10 | 0 | 0 | 0 | 0 |
| Cmpd 7 | 2.0 | WB | 0 | 10 | 0 | 0 | 0 | 0 | 0 | 0 | 0 | 20 | 0 | 0 | 0 | 10 | 0 | 20 | 0 | 0 |
| Cmpd 7 |  | S | 0 | 0 | 0 | 10 | 0 | 10 | 0 | 0 | 0 | 0 | 0 | 0 | 0 | 0 | 0 | 10 | 0 | 0 |
| VC | 0 | WB | 0 | 0 | 0 | 10 | 0 | 0 | 0 | 10 | 0 | 0 | 0 | 0 | 0 | 10 | 0 | 0 | 0 | 0 |
| VC |  | S | 0 | 0 | 0 | 0 | 0 | 10 | 0 | 10 | 0 | 10 | 0 | 0 | 0 | 0 | 0 | 0 | 0 | 0 |

WB = whole blood
S = serum

TABLE 18B

Percent Insecticidal Activity Against *Phormia regina* ("L") and *Stomoxys calcitrans* ("A")
Following 48 hr in vitro Exposure

| Treatment | Dose mg/kg | Blood Sample | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A |
|---|---|---|---|---|---|---|---|---|---|---|---|---|---|---|---|---|---|---|---|---|
| Cmpd 7 | 1.0 | WB | 0 | 20 | 0 | 0 | 0 | 0 | 0 | 0 | 0 | 10 | 0 | 20 | 0 | 10 | 0 | 10 | 0 | 0 |
| Cmpd 7 |  | S | 0 | 0 | 0 | 0 | 0 | 10 | 0 | 30 | 0 | 0 | 0 | 10 | 0 | 40 | 0 | 30 | 0 | 0 |
| Cmpd 7 | 1.0 | WB | 0 | 0 | 0 | 10 | 0 | 0 | 0 | 0 | 0 | 0 | 0 | 0 | 0 | 0 | 0 | 20 | 0 | 10 |
| Cmpd 7 |  | S | 0 | 10 | 0 | 30 | 0 | 10 | 0 | 40 | 0 | 0 | 0 | 10 | 0 | 0 | 0 | 30 | 0 | 0 |
| Cmpd 7 | 2.0 | WB | 0 | 0 | 0 | 10 | 0 | 10 | 0 | 10 | 0 | 0 | 0 | 0 | 0 | 20 | 0 | 20 | 0 | 0 |
| Cmpd 7 |  | S | 0 | 0 | 0 | 30 | 0 | 20 | 0 | 30 | 0 | 20 | 0 | 10 | 0 | 40 | 0 | 20 | 0 | 0 |
| Cmpd 7 | 2.0 | WB | 0 | 10 | 0 | 0 | 0 | 10 | 0 | 10 | 0 | 20 | 0 | 0 | 0 | 20 | 0 | 20 | 0 | 30 |
| Cmpd 7 |  | S | 0 | 10 | 0 | 10 | 0 | 20 | 0 | 20 | 0 | 0 | 0 | 50 | 0 | 0 | 0 | 30 | 0 | 0 |
| VC | 0 | WB | 0 | 0 | 0 | 20 | 0 | 10 | 0 | 20 | 0 | 0 | 0 | 0 | 0 | 20 | 0 | 10 | 0 | 0 |
| VC |  | S | 0 | 10 | 0 | 0 | 0 | 20 | 0 | 10 | 0 | 0 | 0 | 0 | 0 | 10 | 0 | 10 | 0 | 0 |

TABLE 18C

Examination of Subcutaneous Injection Sites for Seven Days Following Treatment of Calves
Size[1] and State of Injection Site Swelling

| Treatment | Dose mg/kg | Day 2 | Day 3 | Day 4 | Day 5 | Day 6 | Day 7 |
|---|---|---|---|---|---|---|---|
| Cmpd 7 | 1.0 | 5.2 × 7.6 (S) | 7.6 × 7.6 (SF) | 7.6 × 10.3 (SF) | 7.6 × 10.3 (SF) | 7.6 × 10.3 (SF) | 7.6 × 15 (F) |
| Cmpd 7 | 1.0 | 5.2 × 7.6 (S) | 7.6 × 7.6 (SF) | 7.6 × 7.6 (SF) | 7.6 × 7.6 (SF) | 7.6 × 7.6 (SF) | 7.6 × 7.6 (F) |
| Cmpd 7 | 2.0 | 5.2 × 7.6 (S) | 7.6 × 7.6 (SF) | 7.6 × 7.6 (SF) | 7.6 × 7.6 (SF) | 7.6 × 7.6 (SF) | 7.6 × 7.6 (F) |
| Cmpd 7 | 2.0 | 5.2 × 7.6 (S) | 7.6 × 7.6 (SF) | 7.6 × 7.6 (SF) | 7.6 × 7.6 (SF) | 7.6 × 7.6 (SF) | 7.6 × 7.6 (F) |

TABLE 18C-continued

Examination of Subcutaneous Injection Sites for Seven Days Following Treatment of Calves Size[1] and State of Injection Site Swelling

| Treatment | Dose mg/kg | Day 2 | Day 3 | Day 4 | Day 5 | Day 6 | Day 7 |
|---|---|---|---|---|---|---|---|
| VC | -VC | none | none | none | none | none | none |

[1] cm × cm
F = firm
S = soft
SF = soft perimeter, firm center

TABLE 19A

Percent Insecticidal Activity Against *Phormia regina* ("L") and *Stomoxys calcitrans* ("A")
Following 24 hr in vitro Exposure
Test 19: Evaluation of 1,5-bis(4-(trifluoromethyl)phenyl)-3-formazancarbonitrile trimethyloctadecylammonium salt (Cmpd 13), In Cattle, Administered Subcutaneously, Dissolved in DMSO, 80 mg/ml

| Treatment | Dose mg/kg | Blood Sample | Pre L | Pre A | 30 Min L | 30 Min A | 5 Hr L | 5 Hr A | Day 1 L | Day 1 A | Day 2 L | Day 2 A | Day 3 L | Day 3 A | Day 4 L | Day 4 A |
|---|---|---|---|---|---|---|---|---|---|---|---|---|---|---|---|---|
| Cmpd 13 | 1.0 | WB | 0 | 10 | 0 | 0 | 0 | 0 | 0 | 10 | 0 | 10 | 0 | 0 | 0 | 20 |
| Cmpd 13 |  | S | 0 | 0 | 0 | 30 | 0 | 20 | 0 | 0 | 0 | 10 | 0 | 10 | 0 | 10 |
| Cmpd 13 | 1.0 | WB | 0 | 0 | 0 | 0 | 0 | 0 | 0 | 0 | 0 | 10 | 0 | 0 | 0 | 0 |
| Cmpd 13 |  | S | 0 | 0 | 0 | 0 | 0 | 10 | 0 | 0 | 0 | 0 | 0 | 20 | 0 | 10 |
| Cmpd 13 | 2.0 | WB | 0 | 0 | 0 | 10 | 0 | 10 | 0 | 0 | 0 | 10 | 0 | 0 | 0 | 10 |
| Cmpd 13 |  | S | 0 | 10 | 0 | 30 | 0 | 10 | 0 | 20 | 0 | 0 | 0 | 0 | 0 | 10 |
| Cmpd 13 | 2.0 | WB | 0 | 10 | 0 | 10 | 0 | 0 | 0 | 0 | 0 | 0 | 0 | 0 | 0 | 0 |
| Cmpd 13 |  | S | 0 | 0 | 0 | 0 | 0 | 0 | 0 | 0 | 0 | 10 | 0 | 10 | 0 | 0 |
| Oxfendazole[1] (ref. standard) | 10.0 | WB | 0 | 0 | 0 | 0 | 0 | 20 | 0 | 0 | 0 | 10 | 0 | 0 | 0 | 0 |
| Oxfendazole[1] (ref. standard) |  | S | 0 | 0 | 0 | 0 | 0 | 10 | 0 | 10 | 0 | 0 | 0 | 0 | 0 | 10 |
| Oxfendazole[1] (ref. standard) | 10.0 | WB | 0 | 10 | 0 | 10 | 0 | 0 | 0 | 20 | 0 | 10 | 0 | 0 | 0 | 10 |
| Oxfendazole[1] (ref. standard) |  | S | 0 | 0 | 0 | 0 | 0 | 20 | 0 | 0 | 0 | 10 | 0 | 20 | 0 | 0 |
| Vehicle (DMSO) | 0 | WB | 0 | 0 | 0 | 10 | 0 | 0 | 0 | 0 | 0 | 10 | 0 | 10 | 0 | 0 |
| Vehicle (DMSO) |  | S | 0 | 0 | 0 | 10 | 0 | 10 | 0 | 10 | 0 | 0 | 0 | 0 | 0 | 0 |

[1] Single intraruminal injection
S = serum
WB = whole blood

TABLE 19B

Percent Insecticidal Activity Against *Phormia regina* ("L") and *Stomoxys calcitrans* ("A")
Following 48 hr in vitro Exposure

| Treatment | Dose mg/kg | Blood Sample | Pre L | Pre A | 30 Min L | 30 Min A | 5 Hr L | 5 Hr A | Day 1 L | Day 1 A | Day 2 L | Day 2 A | Day 3 L | Day 3 A | Day 4 L | Day 4 A |
|---|---|---|---|---|---|---|---|---|---|---|---|---|---|---|---|---|
| Cmpd 13 | 1.0 | WB | 0 | 10 | 0 | 10 | 0 | 10 | 0 | 10 | 0 | 10 | 0 | 10 | 0 | 30 |
| Cmpd 13 |  | S | 0 | 0 | 0 | 30 | 0 | 20 | 0 | 10 | 0 | 10 | 0 | 10 | 0 | 10 |
| Cmpd 13 | 1.0 | WB | 0 | 10 | 0 | 0 | 0 | 10 | 0 | 10 | 0 | 20 | 0 | 0 | 0 | 10 |
| Cmpd 13 |  | S | 0 | 10 | 0 | 10 | 0 | 20 | 0 | 0 | 0 | 10 | 0 | 30 | 0 | 20 |
| Cmpd 13 | 2.0 | WB | 0 | 0 | 0 | 10 | 0 | 20 | 0 | 10 | 0 | 10 | 0 | 20 | 0 | 20 |
| Cmpd 13 |  | S | 0 | 20 | 0 | 60 | 0 | 20 | 0 | 50 | 0 | 20 | 0 | 10 | 0 | 20 |
| Cmpd 13 | 2.0 | WB | 0 | 20 | 0 | 10 | 0 | 0 | 0 | 10 | 0 | 0 | 0 | 10 | 0 | 0 |
| Cmpd 13 |  | S | 0 | 10 | 0 | 0 | 0 | 0 | 0 | 0 | 0 | 20 | 0 | 20 | 0 | 0 |
| Oxfendazole[1] (ref. standard) | 10.0 | WB | 0 | 0 | 0 | 10 | 0 | 50 | 0 | 20 | 0 | 20 | 0 | 0 | 0 | 10 |
| Oxfendazole[1] (ref. standard) |  | S | 0 | 0 | 0 | 0 | 0 | 10 | 0 | 20 | 0 | 0 | 0 | 0 | 0 | 10 |
| Oxfendazole[1] (ref. standard) | 10.0 | WB | 0 | 10 | 0 | 20 | 0 | 10 | 0 | 30 | 0 | 10 | 0 | 10 | 0 | 20 |
| Oxfendazole[1] (ref. standard) |  | S | 0 | 0 | 0 | 20 | 0 | 30 | 0 | 0 | 0 | 10 | 0 | 20 | 0 | 20 |
| Vehicle (DMSO) | 0 | WB | 0 | 10 | 0 | 10 | 0 | 10 | 0 | 0 | 0 | 20 | 0 | 10 | 0 | 0 |
| Vehicle (DMSO) |  | S | 0 | 0 | 0 | 10 | 0 | 10 | 0 | 10 | 0 | 10 | 0 | 10 | 0 | 0 |

TABLE 19C

Examination of Subcutaneous Injection Sites for Six Days Following Treatment of Calves Size[1] and State of Injection Site Swelling

| Treatment | Dose mg/kg | Day 1 | Day 2 | Day 3 | Day 4 | Day 6 |
|---|---|---|---|---|---|---|
| Cmpd 13 | 1.0 | 0 | 7.8 × 10.5 (S) | 7.8 × 10.5 (S) | 7.8 × 10.5 (F) | 7.8 × 10.5 (SF) |
| Cmpd 13 | 1.0 | 0 | 7.8 × 15.1 (S) | 7.8 × 10.5 (S) | 7.8 × 15.1 (F) | 7.8 × 10.5 (F) |
| Cmpd 13 | 2.0 | 0 | 0 | 0 | 7.8 × 10.5 (F) | 7.8 × 15.6 (F) |
| Cmpd 13 | 2.0 | 0 | 0 | 0 | 7.8 × 10.5 (F) | 7.8 × 20.1 (F) |
| Vehicle (DMSO) | -VC | 0 | 0 | 0 | 0 | 0 |

[1] cm × cm
F = firm
S = soft

TABLE 20A

Helminthologic Data
Test 20: Evaluation of 1,5-bis(4-(trifluoromethyl)phenyl)-3-formazancarbonitrile In Cattle,
Administered Intraruminally ("IR") or Subcutaneously ("SC"),
Using Formulation In Ethanol and Polyethylene Glycol 200

| Treatment | Dose (mg/kg) | Pre* OST | Worm Eggs Per Gram of Feces — Days Following Treatment | | | | | | | | % Worm Egg Reduction OST | Total Worm Counts[1] OST |
|---|---|---|---|---|---|---|---|---|---|---|---|---|
| | | | 1 OST | 2 OST | 3 OST | 4 OST | 5–7* OST | 9 OST | 11 OST | 14 OST | | |
| Treated | 10 IR | 667 | 300 | 700 | 500 | 500 | 450 | 300 | 100 | 400 | 40.0 | N/D |
| | 10 SC | 333 | 100 | 100 | 100 | 100 | 100 | 100 | 300 | 100 | 69.9 | N/D |
| | 10 SC | 533 | 200 | 200 | 300 | 300 | 150 | 100 | 100 | 100 | 81.2 | 291 |
| | 10 SC | 367 | 400 | 300 | 300 | 300 | 450 | 200 | 300 | 400 | 0 | N/D |
| VC | 0 SC[2] | 367 | 500 | 500 | 500 | 500 | 500 | 300 | 300 | 400 | 0 | N/D |

*Average of 3 days sampling
**Euthanized 15 days post treatment
[1] At necropsy 7 days following treatment
[2] Single subcutaneous injection of 20 ml ethanol + 30 ml PEG 200.
N/D = not done
OST = *Ostertagia ostertagi*

TABLE 20B

Percent Insecticidal Activity Against *Phormia regina* ("L") and *Stomoxys calcitrans* ("A")
Following 24 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A | Day 9 L | Day 9 A | Day 11 L | Day 11 A | Day 14 L | Day 14 A |
|---|---|---|---|---|---|---|---|---|---|---|---|---|---|---|---|---|---|---|---|---|---|---|---|---|---|
| Treated | 10 (IR) | 0 | 0 | 0 | 0 | 0 | 0 | 0 | 0 | 0 | 10 | 0 | 0 | 0 | 0 | 0 | 0 | 0 | 0 | 0 | 0 | 0 | 0 | 0 | 0 |
| Treated | 10 (SC) | 0 | 10 | 0 | 0 | 0 | 0 | 0 | 0 | 0 | 10 | 0 | 10 | 0 | 0 | 0 | 0 | 0 | 10 | 0 | 0 | 0 | 0 | 0 | 0 |
| Treated | 10 (SC) | 0 | 0 | 0 | 0 | 0 | 0 | 0 | 0 | 0 | 0 | 0 | 0 | 0 | 20 | 0 | 0 | 0 | 0 | 0 | 0 | 0 | 0 | 0 | 0 |
| Treated | 10 (SC) | 0 | 0 | 0 | 0 | 0 | 20 | 0 | 30 | 0 | 0 | 0 | 0 | 0 | 10 | 0 | 0 | 0 | 0 | 0 | 10 | 0 | 0 | 0 | 0 |
| VC | | 0 | 10 | 0 | 0 | 0 | 0 | 0 | 0 | 0 | 0 | 0 | 0 | 0 | 10 | 0 | 0 | 0 | 0 | 0 | 10 | 0 | 0 | 0 | 0 |

TABLE 20C

Percent Insecticidal Activity Against *Phormia regina* ("L") and *Stomoxys calcitrans* ("A")
Following 48 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A | Day 9 L | Day 9 A | Day 11 L | Day 11 A | Day 14 L | Day 14 A |
|---|---|---|---|---|---|---|---|---|---|---|---|---|---|---|---|---|---|---|---|---|---|---|---|---|---|
| Treated | 10 (IR) | 0 | 0 | 0 | 12 | 0 | 90 | 0 | 90 | 0 | 2 | 0 | 18 | 0 | 0 | 0 | 0 | 0 | 60 | 0 | 12 | 0 | 10 | 0 | 12 |
| Treated | 10 (SC) | 0 | 12 | 0 | 0 | 0 | 2 | 0 | 60 | 0 | 60 | 0 | 50 | 0 | 60 | 0 | 0 | 0 | 60 | 0 | 22 | 0 | 22 | 0 | 60 |
| Treated | 10 (SC) | 0 | 12 | 0 | 12 | 10 | 0 | 0 | 50 | 0 | 60 | 0 | 18 | 0 | 60 | 0 | 50 | 0 | 0 | 0 | 12 | 0 | 2 | 0 | 2 |
| Treated | 10 (SC) | 0 | 12 | 0 | 0 | 30 | 2 | 0 | 90 | 0 | 90 | 0 | 50 | 0 | 60 | 0 | 90 | 0 | 70 | 0 | 80 | 0 | 70 | 0 | 70 |
| VC | | 0 | 12 | 0 | 12 | 0 | 2 | 0 | 0 | 0 | 0 | 0 | 2 | 0 | 0 | 0 | 2 | 0 | 0 | 0 | 12 | 0 | 12 | 0 | 0 |

TABLE 20D

Examination of Subcutaneous Injection Sites
Eleven Days Following Treatment of Calves

| Treatment | Swelling | Diameter Size (cm) | State |
|---|---|---|---|
| Treated (IR) | No | — | — |
| Treated (SC) | Yes | 7.8 | Soft exterior; hard center |
| Treated (SC) | Yes | 6.4 | Soft exterior; hard center |
| Treated (SC) | Yes | 4.0 | Soft exterior; hard center |
| Control (SC) | No | — | — |

TABLE 21A

Test 21: Evaluation of 1,5-bis(4-(trifluoromethyl)phenyl)-3-formazancarbonitrile (Cmpd 6)
and its Tetraethylammonium Salt (Cmpd 9), Administered by Several Routes,
PEG 200 Formulations

| Treatment | Dose mg/kg & Route of Admin | Pre* OST | Helminthologic Data — Worm Eggs Per Gram of Feces — Days Following Treatment | | | | | % Worm Egg Reduction OST | Total Worm Counts[1] | % Worm Reduction |
|---|---|---|---|---|---|---|---|---|---|---|
| | | | 1 OST | 2 OST | 3 OST | 4 OST | 5–7* OST | | | |
| Cmpd 6 | 40 IR | 200 | 300 | 200 | 300 | 200 | 250 | 0 | 1756 | 0 |
| Cmpd 6 | 40 IR | 300 | 100 | 200 | 200 | 200 | 200 | 33.3 | 658 | 51.6 |
| Cmpd 9 | 10 SC | 200 | 300 | 300 | 200 | 100 | 250 | 0 | 840 | 38.2 |
| Cmpd 9 | 10 SC | 400 | 300 | 300 | 300 | 100 | 275 | 31.2 | 2482 | 0 |
| Cmpd 6 | 1.0 IV | 400 | DIED | | | | | | | |

TABLE 21A-continued

Test 21: Evaluation of 1,5-bis(4-(trifluoromethyl)phenyl)-3-formazancarbonitrile (Cmpd 6) and its Tetraethylammonium Salt (Cmpd 9), Administered by Several Routes, PEG 200 Formulations

| Treatment | Dose mg/kg & Route of Admin | Pre* OST | 1 OST | 2 OST | 3 OST | 4 OST | 5-7* OST | % Worm Egg Reduction OST | Total Worm Counts[1] | % Worm Reduction |
|---|---|---|---|---|---|---|---|---|---|---|
| VC | 0 SC | 200 | 400 | 300 | 200 | 300 | 250 | 0 | 1360 | — |

*Average of 3 days sampling
[1]At necropsy 7 days following treatment
IR = intraruminal
IV = intravenous
OST = *Ostertagia spp.*
SC = subcutaneous

TABLE 21B

Percent Insecticidal Activity Against *Phormia regina* ("L") and *Stomoxys calcitrans* ("A") Following 24 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 7 L | Day 7 A |
|---|---|---|---|---|---|---|---|---|---|---|---|---|---|---|---|---|---|---|---|
| Cmpd 6 | 40 IR | 0 | 0 | 0 | 10 | 0 | 10 | 0 | 20 | 0 | 0 | 0 | 0 | 0 | 10 | 0 | 10 | 0 | 0 |
| Cmpd 6 | 40 IR | 0 | 0 (10) | 0 | 0 | 0 | 0 | 100 | 50 | 0 | 0 | 0 | 10 | 0 | 0 | 0 | 10 | 0 | 10 |
| Cmpd 9 | 10 SC | 0 | 0 (10) | 0 | 10 | 0 | 10 | 0 | 0 | 0 | 0 | 0 | 0 | 0 | 0 | 0 | 0 | 0 | 0 |
| Cmpd 9 | 10 SC | 0 | 0 | 0 | 0 | 25 | 10 | 0 | 10 | 90 | 20 | 10 | 10 | 0 | 0 | 0 | 0 | 0 | 0 |
| Cmpd 6 | 1.0 IV | 0 | 0 | 25 | 50 | 10 | 10 | DIED | | | | | | | | | | | |
| VC | 0 SC | 0 | 0 | 0 | 0 | 0 | 0 | 0 | 0 | 0 | 10 | 0 | 0 | 0 | 0 | 0 | 0 | 0 | 0 |

(no.) actual mortality before adjustment

TABLE 21C

Percent Insecticidal Activity Against *Phormia regina* ("L") and *Stomoxys calcitrans* ("A") Following 48 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 7 L | Day 7 A |
|---|---|---|---|---|---|---|---|---|---|---|---|---|---|---|---|---|---|---|---|
| Cmpd 6 | 40 IR | 0 | 10 (60) | 0 | 10 (30) | 0 | 80 (80) | 90 | 100 | 0 | 20 (70) | 0 | 0 (10) | 0 | 10 (30) | 0 | 10 (10) | 0 | 0 (30) |
| Cmpd 6 | 40 IR | 0 | 0 (50) | 0 | 0 (10) | 0 | 10 (60) | 100 | 90 | 0 | 40 (90) | 0 | 10 (40) | 0 | 10 (60) | 0 | 0 (30) | 0 | 20 (70) |
| Cmpd 9 | 10 SC | 0 | 0 (10) | 0 | 10 (20) | 0 | 10 (10) | 0 | 70 | 0 | 90 (90) | 0 | 0 (20) | 0 | 0 (30) | 0 | 0 (30) | 0 | 0 (20) |
| Cmpd 9 | 10 SC | 0 | 0 (50) | 0 | 0 (80) | 100 | 80 | 0 | 90 | 100 | 90 | 25 | 40 (50) | 25 | 0 (40) | 0 | 0 | 0 | 30 (80) |
| Cmpd 6 | 1.0 IV | 0 | 0 (10) | 60 | 90 | 10 | 80 | DIED | | | | | | | | | | | |
| VC | 0 SC | 0 | 20 (70) | 0 | 20 (70) | 0 | 0 (50) | 0 | 0 (50) | 0 | 40 (90) | 0 | 10 (60) | 0 | 0 (10) | 0 | 0 (30) | 0 | 0 (50) |

TABLE 21D

Examination of Subcutaneous Injection Sites Ten Days After Treatment of Calves

| Treatment | Swelling | Diameter Size (cm) | State |
|---|---|---|---|
| Cmpd 9 | Yes | 15 | Firm |
| Cmpd 9 | Yes | 7.5 | Soft |
| VC | No | — | — |

TABLE 22A

Test 22: Evaluation of Salts of 1,5-bis(4-(trifluoromethyl)phenyl)-3-formazancarbonitrile in Cattle Administered Intraruminally Using Formulations L, M, and N

| Treatment | Dose mg/kg | Pre* OST | 1 OST | 2 OST | 3 OST | 4 OST | 10* OST | % Worm Egg Reduction OST |
|---|---|---|---|---|---|---|---|---|
| Cmpd 11, Form L | 16.26 | 350 | 300 | 0 | 0 | 400 | 300 | 14.3 |
| Cmpd 11, Form L | 16.26 | 700 | 200 | 0 | 0 | 200 | 500 | 28.6 |
| Cmpd 9, Form M | 13.40 | 1050 | 400 | 400 | 0 | 400 | 300 | 71.4 |
| Cmpd 9, Form M | 13.40 | 1050 | 500 | 0 | 0 | 400 | 300 | 71.4 |
| Cmpd 12, Form N | 17.70 | 650 | 300 | 0 | 0 | 100 | 100 | 76.9 |
| Cmpd 12, Form N | 17.70 | 400 | 200 | 100 | 0 | 500 | 200 | 50.0 |

TABLE 22A-continued

Test 22: Evaluation of Salts of
1,5-bis(4-(trifluoromethyl)phenyl)-3-
formazancarbonitrile in Cattle Administered
Intraruminally Using Formulations L, M, and N

Helminthologic Data

| Worm Eggs Per Gram of Feces (EPG) | % Worm Egg |
|---|---|

| | | | | | | | |
|---|---|---|---|---|---|---|---|
| VC | 0 | 1250 | 1800 | 900 | 1100 | 1100 | 900 | 12.0 |

Cmpd 9 = 1,5-bis(4-(trifluoromethyl)phenyl)-3-formazancarbonitrile tetraethylammonium salt
Cmpd 11 = 1,5-bis(4-(trifluoromethyl)phenyl)-3-formazancarbonitrile tetra-n-butylammonium salt
Cmpd 12 = 1,5-bis(4-(trifluoromethyl)phenyl)-3-formazancarbonitrile tetra-n-pentylammonium salt
*Average of 3 days sampling
OST = *Ostertagia ostertagi*

TABLE 22B

Percent Insecticidal Activity Against *Phormia regina* ("L") and *Stomoxys calcitrans* ("A")
Following 24 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A |
|---|---|---|---|---|---|---|---|---|---|---|---|---|---|
| Cmpd 11, Form L | 16.26 | 0 | 0 | 0 | 0 | 0 | 0 | 0 | 30 | 90 | 20 | 0 | 0 |
| Cmpd 11, Form L | 16.26 | 0 | 0 | 0 | 0 | 0 | 20 | 100 | 100 | 100 | 50 | 0 | 0 |
| Cmpd 9, Form M | 13.40 | 0 | 0 | 0 | 20 | 10 | 0 | 10 | 30 | 10 | 20 | 0 | 0 |
| Cmpd 9, Form M | 13.40 | 0 | 0 | 0 | 10 | 0 | 0 | 100 | 60 | 100 | 60 | 0 | 10 |
| Cmpd 12, Form N | 17.70 | 0 | 0 | 0 | 20 | 0 | 0 | 60 | 100 | 100 | 90 | 0 | 0 |
| Cmpd 12, Form N | 17.70 | 0 | 0 | 0 | 10 | 0 | 20 | 50 | 60 | 100 | 90 | 0 | 0 |
| VC | 0 | 0 | 10 | 0 | 20 | 0 | 0 | 20 | 0 | 0 | 10 | 0 | 20 |

TABLE 22C

Percent Insecticidal Activity Against *Phormia regina* ("L") and *Stomoxys calcitrans* ("A")
Following 48 hr in vitro Exposure

| Treatment | Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A |
|---|---|---|---|---|---|---|---|---|---|---|---|---|---|
| Cmpd 11, Form L | 16.26 | 0 | 0 | 0 | 10 | 0 | 10 | 0 | 90 | 100 | 100 | 0 | 20 |
| Cmpd 11, Form L | 16.26 | 0 | 0 | 0 | 10 | 75 | 100 | 100 | 100 | 100 | 100 | 0 | 30 |
| Cmpd 9, Form M | 13.40 | 0 | 20 | 0 | 20 | 10 | 90 | 30 | 100 | 10 | 60 | 0 | 10 |
| Cmpd 9, Form M | 13.40 | 0 | 0 | 0 | 10 | 0 | 30 | 100 | 100 | 100 | 90 | 0 | 30 |
| Cmpd 12, Form N | 17.70 | 0 | 10 | 0 | 30 | 0 | 60 | 90 | 100 | 100 | 100 | 0 | 80 |
| Cmpd 12, Form N | 17.70 | 0 | 0 | 0 | 10 | 0 | 20 | 90 | 100 | 100 | 100 | 0 | 20 |
| VC | 0 | 0 | 20 | 0 | 20 | 0 | 20 | 0 | 20 | 0 | 10 | 0 | 20 |

TABLE 23A

Test 23: Evaluation in Cattle of 1,5-bis(4-(trifluoromethyl)phenyl)-3-formazancarbonitrile
trimethyloctadecylammonium salt (Cmpd 13) Alone and in Combination With Oxfendazole,
Administered Intraruminally, Formulations O and P

| | | Helminthologic Data | | | | | | | | |
|---|---|---|---|---|---|---|---|---|---|---|
| | | Worm Eggs Per Gram of Feces (EPG) | | | | | | % Worm | | |
| | | | Days Following Treatment | | | | | Egg | Total Worm | % Worm |
| Treatment | Dose mg/kg | Pre* OST | 1 OST | 2 OST | 3 OST | 4 OST | 5-7* OST | Reduction OST | Counts[1] OST | Reduction OST |
| Cmpd 13 + oxfendazole | 18 + 10 | 1750 | 300 | 0 | 0 | 0 | 0 | 100 | 0 | 100 |
| Cmpd 13 + oxfendazole | 18 + 10 | 1300 | 100 | 0 | 0 | 0 | 0 | 100 | 0 | 100 |
| Cmpd 13 | 18 | 1300 | 1300 | 1400 | 1200 | 1100 | 1375 | 0 | N/D | N/D |
| Cmpd 13 | 18 | 500 | 500 | 600 | 500 | 700 | 600 | 0 | N/D | N/D |
| VC | 0 | 500 | 500 | 500 | 400 | 600 | 500 | 0 | N/D | N/D |

*Average of 3 days sampling
[1]At necropsy 7 days following treatment
N/D = not determined
OST = *Ostertagia ostertagi*

| Treatment | Dose mg/kg | Pre* OST | Days Following Treatment | | | | | Reduction OST |
|---|---|---|---|---|---|---|---|---|
| | | | 1 OST | 2 OST | 3 OST | 4 OST | 10* OST | |

TABLE 23B

Percent Insecticidal Activity Against *Phormia regina* ("L") and *Stomoxys calcitrans* ("A")
Following 24 hr in vitro Exposure

| Treatment | Dose mg/kg | Blood Sample | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|---|---|---|---|---|---|
| Cmpd 13 + oxfendazole | 18 + 10 | WB | 0 | 0 | 0 | 0 | 0 | 40 | 40 | 10 | 30 | 30 | 40 | 10 | 0 | 20 | 0 | 10 |
| Cmpd 13 + oxfendazole | 18 + 10 | S | 0 | 0 | 0 | 0 | 40 | 20 | 100 | 90 | 100 | 80 | 100 | 30 | 100 | 90 | 0 | 20 |
| Cmpd 13 + oxfendazole | 18 + 10 | WB | 0 | 20 | 0 | 30 | 0 | 10 | 80 | 0 | 80 | 10 | 40 | 20 | 0 | 0 | 0 | 0 |
| Cmpd 13 + oxfendazole | 18 + 10 | S | 0 | 10 | 0 | 0 | 90 | 30 | 100 | 100 | 100 | 90 | 100 | 60 | 100 | 70 | 0 | 20 |
| Cmpd 13 | 18 | WB | 0 | 10 | 0 | 10 | 0 | 0 | 0 | 10 | 0 | 0 | 0 | 10 | 0 | 0 | 0 | 0 |
| Cmpd 13 | 18 | S | 0 | 10 | 0 | 0 | 100 | 0 | 90 | 30 | 0 | 40 | 0 | 0 | 0 | 10 | 0 | 10 |
| Cmpd 13 | 18 | WB | 0 | 10 | 0 | 0 | 0 | 20 | 0 | 0 | 0 | 20 | 0 | 20 | 0 | 0 | 0 | 0 |
| Cmpd 13 | 18 | S | 0 | 10 | 0 | 0 | 100 | 40 | 90 | 60 | 50 | 30 | 0 | 0 | 0 | 10 | 0 | 10 |
| VC | 0 | WB | 0 | 10 | 0 | 10 | 0 | 0 | 0 | 10 | 0 | 0 | 0 | 10 | 0 | 0 | 0 | 0 |

TABLE 23B-continued

Percent Insecticidal Activity Against *Phormia regina* ("L") and *Stomoxys calcitrans* ("A")
Following 24 hr in vitro Exposure

| Treatment | Dose mg/kg | Blood Sample | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|---|---|---|---|---|---|
| VC | 0 | S | 0 | 0 | 0 | 10 | 0 | 0 | | | 0 | 0 | 10 | 0 | 0 | 0 | 0 | 0 |

WB = whole blood
S = serum

TABLE 23C

Percent Insecticidal Activity Against *Phormia regina* ("L") and *Stomoxys calcitrans* ("A")
Following 48 hr in vitro Exposure

| Treatment | Dose mg/kg | Blood Sample | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A |
|---|---|---|---|---|---|---|---|---|---|---|---|---|---|---|---|---|---|---|
| Cmpd 13 + oxfendazole | 18 + 10 | WB | 0 | 10 | 0 | 30 | 0 | 50 | 40 | 90 | 30 | 80 | 40 | 80 | 0 | 40 | 0 | 10 |
| Cmpd 13 + oxfendazole | 18 + 10 | S | 0 | 10 | 0 | 30 | 80 | 90 | 100 | 100 | 100 | 100 | 100 | 100 | 100 | 100 | 0 | 50 |
| Cmpd 13 + oxfendazole | 18 + 10 | WB | 0 | 30 | 0 | 40 | 0 | 30 | 90 | 90 | 90 | 90 | 40 | 80 | 0 | 30 | 0 | 10 |
| Cmpd 13 + oxfendazole | 18 + 10 | S | 0 | 10 | 0 | 10 | 100 | 100 | 100 | 100 | 100 | 100 | 100 | 90 | 100 | 90 | 0 | 30 |
| Cmpd 13 | 18 | WB | 0 | 20 | 0 | 10 | 0 | 10 | 0 | 40 | 0 | 10 | 0 | 10 | 0 | 10 | 0 | 10 |
| Cmpd 13 | 18 | S | 0 | 10 | 0 | 0 | 100 | 80 | 100 | 100 | 0 | 50 | 0 | 40 | 0 | 10 | 0 | 20 |
| Cmpd 13 | 18 | WB | 0 | 20 | 0 | 20 | 0 | 30 | 0 | 0 | 0 | 30 | 0 | 70 | 0 | 10 | 0 | 10 |
| Cmpd 13 | 18 | S | 0 | 20 | 0 | 20 | 100 | 80 | 100 | 100 | 60 | 80 | 0 | 50 | 0 | 20 | 0 | 20 |
| VC | 0 | WB | 0 | 20 | 0 | 20 | 0 | 30 | 0 | 10 | 0 | 20 | 0 | 20 | 0 | 0 | 0 | 20 |
| VC | 0 | S | 0 | 10 | 0 | 30 | 0 | 10 | 0 | 10 | 0 | 30 | 0 | 10 | 0 | 10 | 0 | 10 |

TABLE 24A

Test 24: Evaluation in Cattle of 1,5-bis(4-(trifluoromethylphenyl)-3-formazancarbonitrile trimethyloctadecylammonium salt (Cmpd 13), Administered Intraruminally, Formulation S Helminthologic Data

| Dose mg/kg | Worm Eggs Per Gram of Feces (EPG) Pre* | Days Following Treatment 1 | 2 | 3 | 4 | 5–7* | % Worm Egg Reduction | Total Worm Counts[1] | % Worm Reduction |
|---|---|---|---|---|---|---|---|---|---|
| 18 | 267 | 0 | 0 | 0 | 0 | 0 | 100 | 64** | 73.8 |
| 18 | 67 | 0 | 0 | 0 | 0 | 0 | 100 | 17** | 93.0 |
| VC | 167 | 300 | 300 | 400 | 300 | 225 | 0 | 244 | 0 |

*Average of 3 days sampling
**Ova appeared non-viable. Female worms had only 6–8 eggs in utero and were granular and unsegmented.
[1]At necropsy 7 days following treatment

TABLE 24B

Percent Insecticidal Activity against *Phormia regina* ("L") and *Stomoxys calcitrans* ("A")
Following 24 hr in vitro Exposure

| Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A |
|---|---|---|---|---|---|---|---|---|---|---|---|---|---|---|---|---|---|---|
| 18 | 0 | 0 | 0 | 0 | 0 | 10 | 25 | 20 | 0 | 40 | 0 | 10 | 0 | 0 | 0 | 0 | 0 | 0 |
| 18 | 0 | 20 | 0 | 0 | 0 | 10 | 100 | 70 | 0 | 0 | 0 | 10 | 0 | 0 | 0 | 0 | 0 | 0 |
| VC | 0 | 10 | 0 | 0 | 0 | 20 | 0 | 0 | 0 | 10 | 0 | 0 | 0 | 10 | 0 | 0 | 0 | 10 |

TABLE 24C

Percent Insecticidal Activity against *Phormia regina* ("L") and *Stomoxys calcitrans* ("A")
Following 48 hr in vitro Exposure

| Dose mg/kg | Day 0 L | Day 0 A | 30 Min L | 30 Min A | 5 Hr L | 5 Hr A | Day 1 L | Day 1 A | Day 2 L | Day 2 A | Day 3 L | Day 3 A | Day 4 L | Day 4 A | Day 5 L | Day 5 A | Day 6 L | Day 6 A |
|---|---|---|---|---|---|---|---|---|---|---|---|---|---|---|---|---|---|---|
| 18 | 0 | 30 | 0 | 30 | 0 | 40 | 90 | 100 | 60 | 80 | 0 | 30 | 0 | 20 | 0 | 20 | 0 | 10 |
| 18 | 0 | 20 | 0 | 30 | 0 | 60 | 100 | 100 | 0 | 50 | 0 | 0 | 0 | 30 | 0 | 10 | 0 | 20 |
| VC | 0 | 20 | 0 | 20 | 0 | 30 | 0 | 10 | 0 | 30 | 0 | 20 | 0 | 10 | 0 | 30 | 0 | 10 |

TABLE 25A

Test 25: Evaluation in Cattle of 1,5-bis(4-(trifluoromethylphenyl)-3-formazancarbonitrile trimethyloctadecylammonium salt (Cmpd 13), Administered Intraruminally as an Emulsion[2]

Helminthologic Data

| Dose mg/kg | Worm Eggs Per Gram of Feces (EPG) Pre* | Days Following Treatment 1 | 2 | 3 | 4 | 5–7* | 10 | % Worm Egg Reduction | Total Worm Counts[1] |
|---|---|---|---|---|---|---|---|---|---|
| 18 | 550 | 500 | 800 | 600 | 600 | 800 | 800 | 0 | ND |

TABLE 25A-continued

Test 25: Evaluation in Cattle of 1,5-bis(4-(trifluoromethylphenyl)-3-formazancarbonitrile trimethyloctadecylammonium salt (Cmpd 13), Administered Intraruminally as an Emulsion[2]

| Dose mg/kg | Helminthologic Data Worm Eggs Per Gram of Feces (EPG) Days Following Treatment | | | | | | | % Worm Egg Reduction | Total Worm Counts[1] |
|---|---|---|---|---|---|---|---|---|---|
| | Pre* | 1 | 2 | 3 | 4 | 5-7* | 10 | | |
| 18 | 750 | 600 | 1200 | 1750 | 900 | 750 | 800 | 0 | ND |
| 36 | 500 | 600 | 900 | 1000 | 700 | 650 | 500 | 0 | ND |
| 36 | 750 | 700 | 1100 | 600 | 500 | 400 | 400 | 46.7 | ND |
| VC | 350 | 500 | 600 | 800 | 600 | 500 | 400 | 0 | ND |

*Average of 3 days sampling
[1] At necropsy 10 days following treatment
[2] Formulation T diluted 1:1 with distilled water
ND = not determined

TABLE 25B

Percent Insecticidal Activity against *Phormia regina* ("L") and *Stomoxys calcitrans* ("A") Following 24 hr in vitro Exposure

| Dose mg/kg | Day 0 | | 30 Min | | 5 Hr | | Day 1 | | Day 2 | | Day 3 | | Day 4 | | Day 5 | | Day 6 | |
|---|---|---|---|---|---|---|---|---|---|---|---|---|---|---|---|---|---|---|
| | L | A | L | A | L | A | L | A | L | A | L | A | L | A | L | A | L | A |
| 18 | 0 | 30 | 0 | 30 | 10 | 30 | 100 | 20 | 0 | 30 | 0 | 10 | 0 | 10 | 0 | 10 | 0 | 40 |
| 18 | 0 | 20 | 0 | 10 | 10 | 0 | 100 | 100 | 0 | 40 | 0 | 10 | 0 | 50 | 0 | 30 | 0 | 10 |
| 36 | 0 | 20 | 0 | 20 | 100 | 50 | 100 | 90 | 90 | 60 | 0 | 20 | 0 | 30 | 0 | 10 | 0 | 20 |
| 36 | 0 | 30 | 0 | 40 | 100 | 20 | 100 | 40 | 0 | 0 | 0 | 0 | 0 | 40 | 0 | 30 | 0 | 10 |
| VC | 0 | 50 | 0 | 30 | 0 | 0 | 0 | 20 | 0 | 30 | 0 | 0 | 0 | 20 | 0 | 60 | 0 | 10 |

TABLE 25C

Percent Insecticidal Activity against *Phormia regina* ("L") and *Stomoxys calcitrans* ("A") Following 48 hr in vitro Exposure

| Dose mg/kg | Day 0 | | 30 Min | | 5 Hr | | Day 1 | | Day 2 | | Day 3 | | Day 4 | | Day 5 | | Day 6 | |
|---|---|---|---|---|---|---|---|---|---|---|---|---|---|---|---|---|---|---|
| | L | A | L | A | L | A | L | A | L | A | L | A | L | A | L | A | L | A |
| 18 | 0 | 40 | 0 | 40 | 90 | 100 | 100 | 100 | 0 | 80 | 0 | 70 | 0 | 20 | 0 | 40 | 0 | 50 |
| 18 | 0 | 30 | 0 | 10 | 90 | 80 | 100 | 100 | 100 | 100 | 0 | 40 | 0 | 50 | 0 | 40 | 0 | 20 |
| 36 | 0 | 40 | 0 | 30 | 100 | 90 | 100 | 100 | 100 | 100 | 0 | 50 | 0 | 50 | 0 | 40 | 0 | 30 |
| 36 | 0 | 30 | 0 | 50 | 100 | 80 | 100 | 100 | 10 | 80 | 0 | 0 | 0 | 50 | 0 | 40 | 0 | 10 |
| VC | 0 | 90 | 0 | 60 | 0 | 10 | 0 | 30 | 0 | 60 | 0 | 0 | 0 | 30 | 0 | 70 | 0 | 30 |

TESTS 26 AND 27

Trials against face fly (*Musca autumnalis*), horn fly (*Haematobia irritans*), and stable fly (*Stomoxys calcitrans*)

1,5-Bis(4-trifluoromethyl)phenyl)-3-formazancarbonitrile trimethyloctadecylammonium salt was evaluated in heifers against
  face fly, *Musca autumnalis*
  horn fly, *Haematobia irritans*
  stable fly, *Stomoxys calcitrans*

Two trials were conducted with the same heifers, two per treatment group and four groups. In the first trial, the compound was employed at rates of 9, 13.5 or 18 mg/kg of the compound; the fourth group received a vehicle control. In the second trial, the compound was employed at 27.0 or 36.0 mg/kg, and the two remaining groups received no treatment (control) and vehicle only (vehicle control). Formulation O was utilized. It and vehicle control were administered by intraruminal injection.

In both trials, various tests were employed to determine efficacy. Feces were collected and bioassayed for activity against first instar face fly and horn fly larvae. Adult horn flies and stable flies were introduced to the heifers and effects noted. Finally, blood was collected and both the blood and serum portion bioassayed against stable flies.

The results observed were as follows. The emergence of face fly and horn fly adults from feces collected 1 and 2 days after treatment was completely inhibited. Populations of adult horn flies feeding on the heifers were reduced at 27 mg/kg; populations of stable flies were not affected. Blood and serum bioassays likewise showed control, especially at the higher doses.

TEST 28

Test against ovine lungworm (*Dictyocaulus filaria*)

1,5-Bis(4-(trifluoromethyl)phenyl)-3-formazancarbonitrile trimethyloctadecylammonium salt was evaluated for the control of ovine lungworm, *Dictyocaulus filaria* in sheep. The compound, formulated as Formulation U, was administered by intraruminal injection to sheep which had previously been inoculated with lungworm larvae. The doses employed were 9, 18, or 36 mg/kg. A fourth group of sheep received only vehicle. Fecal samples were collected over a 7 to 9-day period following treatment, and the sheep were then euthanized and residual lungworms counted.

The results indicated efficacy of the compound against lungworm. The worm counts at necropsy showed reductions of 5.3%, 59.8% and 61.2%, at the three respective dose levels of the compound. Lungworm larval output in the feces was lower in the 18 and 36 mg/kg treatment groups.

TEST 29

Test against horn fly (*Haematobia irritans*), and stable fly (*Stomoxys calcitrans*)

1,5-Bis(4-(trifluoromethyl)phenyl)-3-formazancarbonitrile trimethyloctadecylammonium salt was evaluated for the control of horn flies, *Haematobia irritans* and stable flies, *Stomoxys calcitrans* on beef cattle. Eight animals were used, two per treatment group. The treatments were 18, 27, or 36 mg/kg of the compound or vehicle control. The formulation used was Formulation Q. The effect on horn flies was evaluated by releasing the flies on to the animals and determining mortality. The effect on stable flies was determined by allowing caged flies to feed on the cattle periodically. Feces were also collected and assayed against horn flies.

Horn flies fed on cattle on day 1 were significantly affected. Treatment induced mortality was 72, 95 and 86% for the 18, 27, and 36 mg/kg levels of compound, respectively. The number of surviving horn flies was lower in all treatments than in the controls on days 2 to 5. There was almost no effect of the treatments on stable flies fed only once on treated animals. Mortality produced in stable flies fed four times on the treated animals was statistically higher than mortality measured for either single or double fed flies for all three dosage levels. No immature horn flies emerged from fly seeded manure collected during the second day after treatment for all treatment levels. No flies emerged from manure collected from the 27 and 36 mg/kg levels on day 3 following treatment. This study demonstrated that intraruminal applications of the compound in cattle resulted in systemic transport of the drug or its metabolites in the treated animals.

TESTS 30 AND 31

Tests against the Atwood (ivermectin-resistant) strain of *Haemonchus contortus* in Sheep In a first test, 1,5-bis(4-(trifluoromethyl)phenyl)-3-formazancarbonitrile trimethyloctadecylammonium salt (Compound 13) was evaluated in lambs for the control of the Atwood (ivermectin-resistant) strain of *Haemonchus contortus*. There were two lambs per group and three groups. One group received the compound under evaluation at 36 mg/kg, Formulation R; the second group received the corresponding vehicle; and the third group received ivermectin at 0.2 mg/kg. The subject compound and the vehicle were each administered by a single intraruminal injection. The ivermectin was administered orally.

The lambs were maintained for seven days, then euthanized and the abomasa recovered and counts made. Feces were also collected and egg counts made. Results were as described in the following table.

TABLE 26A

Egg/gm counts and nematode recovery from the abomasa of lambs with Atwood strain *Haemonchus contortus*

| Treatment | Egg/gm in Feces (day) 0 | 3 days post treatment | 7 days post treatment | Haemonchus Male | Haemonchus Female | Trichostrongylus Male | Trichostrongylus Female |
|---|---|---|---|---|---|---|---|
| Vehicle | 2450 | 2900 | 1800 | 660 | 500 | 13 | 80 |
| Control | 4200 | 4100 | 4050 | 433 | 600 | 40 | 73 |
| Ivermectin | 1550 | 3150 | 3500 | 647 | 633 | 0 | 0 |
|  | 7750 | 4250 | 4600 | 733 | 833 | 0 | 0 |
| Cmpd 13 | 3750 | 0 | 0 | 0 | 0 | 13 | 53 |
|  | 3350 | 0 | 0 | 0 | 0 | 0 | 0 |

A followup study was done, with five animals per treatment group, and employing both ivermectin-susceptible and ivermectin-resistant strains of *Haemonchus contortus*. Ivermectin was included as a reference. Compound 13 was administered by intraruminal injection; ivermectin was administered per the product directions. The results were as set forth in the following table.

TABLE 26B

Helminthologic Data Collected From Sheep Infected With Ivermectin-Susceptible or Resistant *Haemonchus contortus* and Treated With Compound 13 or Ivermectin

| Test Group | No. Sheep & Parasite Type | Treatment | Dose mg/kg | Route | Eggs per Gram of Feces Pre | Eggs per Gram of Feces Day 7 | % Reduction EPG | Necropsy Worm Counts Mean Total Worms | % Worm Reduction |
|---|---|---|---|---|---|---|---|---|---|
| 1 | 5 SUS | Cmpd 13 | 2.25 | IR | 2080 | 3300 | 0 | 1013 | 22 |
| 2 | 5 RES | " | 2.25 | IR | 1430 | 2110 | 0 | 1200 | 1.2 |
| 3 | 5 SUS | " | 4.5 | IR | 3070 | 1620 | 47 | 847 | 35 |
| 4 | 5 RES | " | 4.5 | IR | 1600 | 1730 | 0 | 695 | 43 |
| 5 | 5 SUS | " | 9 | IR | 2030 | 1870 | 7.8 | 407 | 69 |
| 6 | 5 RES | " | 9 | IR | 950 | 240 | 75 | 50 | 96 |
| 7 | 5 SUS | Ivermectin | 0.2 | Oral | 1590 | 0 | 100 | 5 | 99.6 |
| 8 | 5 RES | Ivermectin | 0.2 | Oral | 960 | 1560 | 0 | 460 | 62* |
| 9 | 5 SUS | VC | 0 | IR | 2940 | 2720 | 7.5 | 1303 | 0 |
| 10 | 5 RES | VC | 0 | IR | 4450 | 2780 | 37.5 | 1215 | 0 |

IR = intraruminal
SUS = ivermectin-susceptible *Haemonchus contortus*
RES = ivermectin-resistant *Haemonchus contortus*
*indicating that the resistant trait may be weakening

TEST 32

Test against ticks in cattle 1,5-Bis(4-(trifluoromethyl)phenyl)-3-formazancarbonitrile was evaluated, alone and in combination with oxfendazole, in cattle for the control of ticks (*Amblyomma maculatum* and *Dermacentor variabilis*). The dose was 18 or 36 mg/kg. Administration was by intraruminal injection, using Formulation R; oxfendazole was also administered by a separate intraruminal injection. Eight heifers weighing between 180 and 222 kg were employed, allotted to four treatment groups. Each was infected on days -2, 0, 1, 2, and 4, with unfed ticks of both species. The ticks were retained in compartments attached to the bodies of the animals.

Blood samples were taken prior to treatment and daily thereafter, and analyzed by the same in vitro bioassay reported above for larval blow fly and adult stable fly. In general, all dosages of 1,5-bis(4-(trifluoromethyl)phenyl)-3-formazancarbonitrile were active in the 48 hour blood sample following 48 hours in vitro exposure. The higher dose (36 mg/kg) was active for 3 days. For blood samples from animals treated with both 1,5-bis(4-(trifluromethyl)phenyl)-3-formazancarbonitrile and oxfendazole, activity in this bioassay was extended to 5 days following treatment. The animals were also observed for the effect on the ticks. Results at day 35 showed modest control of ticks, as reported in the following tables.

TABLE 27

Percent of Ticks Replete and Ovipositing

TABLE 27A

Activity in Calves Infested With *Amblyomma americanum* Ticks.

| Treatment | No. Ticks Collected | No. Ticks Replete | No. Ticks ovipositing | % Collected Ticks Replete | % Replete Ticks Ovipositing |
| --- | --- | --- | --- | --- | --- |
| VC | 30 | 17 | 16 | 57 | 88 |
| Cmpd 13 18 mg/kg | 31 | 14 | 2 | 45 | 14 |
| Cmpd 13 36 mg/kg | 26 | 14 | 4 | 54 | 29 |
| Cmpd 13 36 mg/kg + oxfendazole 10 mg/kg | 29 | 4 | 2 | 14 | 50 |

TABLE 27B

Activity in Calves Infested With *Dermacentor variabilis* Ticks.

| Treatment | No. Ticks Collected | No. Ticks Replete | No. Ticks ovipositing | % Collected Ticks Replete | % Replete Ticks Ovipositing |
| --- | --- | --- | --- | --- | --- |
| VC | 32 | 22 | 10 | 69 | 45 |
| Cmpd 13 18 mg/kg | 36 | 34 | 16 | 94 | 47 |
| Cmpd 13 36 mg/kg | 37 | 29 | 11 | 78 | 38 |
| Cmpd 13 36 mg/kg + oxfendazole 10 mg/kg | 33 | 21 | 6 | 64 | 29 |

TEST 33

Test against common scabies mite in cattle 1,5-Bis(4-(trifluoromethyl)phenyl)-3-formazancarbonitrile (Compound 13) was evaluated in cattle, alone and in combination with oxfendazole, for the control of common scabies mite (*Psoroptes ovis*). Twelve heifers weighing between 179 and 239 kg were employed, allocated to four treatment groups. Administration was by intraruminal injection, at doses of 18 and 36 mg/kg; oxfendazole was administered by a separate intraruminal injection, at a dose of 10 mg/kg.

The animals were infested by placing onto the withers area a scraping of hair and epidermal matter from a donor animal. To determine the efficacy of treatment, two one-inch square areas were scraped, and the collected hair and mites evaluated for the number of mites. The mite counts were as reported in the following table.

TABLE 28

Activity Against Common Scabies Mite

| Treatment | Dose mg/kg | | Day-1 | Day 2 | Day 4 | Day 7 | Day 14 | Day 21 | Day 28 | Day 35 |
| --- | --- | --- | --- | --- | --- | --- | --- | --- | --- | --- |
| VC | 0 | Avg. No. of Mites | 156 | 93.33 | 145 | 244.33 | 211.66 | 214.33 | 195.5 | 176.5 |
| Cmpd 13 | 18 | Avg. No. of Mites | 102.33 | 57.33 | 38.33 | 82.33 | 126.66 | 96.33 | 121.66 | 58.5 |
| | | % Control | | 38.57% | 73.56% | 66.30% | 40.15% | 55.05% | 37.76% | 66.85% |
| Cmpd 13 | 36 | Avg. No. of Mites | 103.33 | 124.33 | 68.66 | 165.66 | 421.33 | 252.66 | 353.66 | 175.33 |
| | | % Control | | 0% | 52.64% | 32.19% | 0% | 0% | 0% | 0.66% |
| Cmpd 13 + oxfendazole | 36 + 10 | Avg. No. of Mites | 81 | 28 | 9.66 | 7.66 | 6.33 | 32.33 | 38.66 | 150 |
| | | % Control | | 69.99% | 93.56% | 96.86% | 97.0% | 84.91% | 80.22% | 15.01% |

TEST 34

Test against fleas and ticks in dogs 1,5-Bis(4-(trifluoromethyl)phenyl)-3-formazancarbonitrile, as its tetramethylammonium salt (Compound 8) and trimethyloctadecylammonium salt (Compound 13) was evaluated for the control of fleas (*Ctenocephalides felis*) and ticks (*Rhipicephalus sanguineus*) in beagle dogs. Twelve dogs, averaging 11.8 kg and infested with fleas, were allocated to four treatment groups: vehicle control, Compound 8 at 24 mg/kg, Compound 13 at 36 mg/kg, and Compound 13 at 36 mg/kg plus oxfendazole at 10 mg/kg. The vehicle control and Compounds 8 and 13 were administered by oral capsule (Formulation W); oxfendazole was administered by liquid gavage. Reinfestations were done at day 5 for fleas and at days 3 and 6 for ticks. The number of fleas and ticks was averaged for each group. Percent control of fleas and ticks was rated in two ways: by reference to the beginning population in the same treatment group and, for groups receiving a formazan, by reference to the population in the control group on the same day. Results were as set forth in the following tables.

TABLE 29A

Activity against Fleas

| Treatment | Dose mg/kg | Number of Fleas | | | | |
|---|---|---|---|---|---|---|
| | | Day 0 | Day 1 | Day 3 | Day 6 | Day 8 |
| VC | 0 | 86 | 79 | 75 | 91.7 | 78.7 |
| % Reduction from Day 0 | — | — | 8.1 | 12.7 | −6.6 | 8.4 |
| Cmpd 8 | 24 | 90 | 11.3 | 2 | 49.3 | 29.3 |
| % Reduction from Day 0 | — | — | 87.4 | 97.7 | 45.2 | 67.4 |
| % Reduction from Control | — | — | 85.7 | 97.3 | 46.2 | 62.8 |
| Cmpd 13 | 36 | 91.7 | 17 | 0 | 33.3 | 20.3 |
| % Reduction from Day 0 | — | — | 81.5 | 100 | 63.7 | 77.8 |
| % Reduction from Control | — | — | 80.2 | 100 | 63.7 | 74.2 |
| Cmpd 13/ oxfendazole | 36/10 | 85.3 | — | 0 | 18.3 | 8.3 |
| % Reduction from Day 0 | — | — | 100 | 100 | 78.5 | 90.3 |
| % Reduction from Control | — | — | 100 | 100 | 80 | 89.5 |

TABLE 29B

Activity against Ticks

| Treatment | Dose mg/kg | Number of Ticks | | | | |
|---|---|---|---|---|---|---|
| | | Day 0 | Day 1 | Day 3 | Day 6 | Day 8 |
| VC | 0 | 13.7 | 13.7 | 13.3 | 21 | 20 |
| % Reduction from Day 0 | — | — | 0 | 2.9 | −53 | −45 |
| Cmpd 8 | 24 | 18 | 4 | 2 | 14 | 13 |
| % Reduction from Day 0 | — | — | 77.7 | 88.8 | 22.2 | 27.7 |
| % Reduction from Control | — | — | 70.8 | 85 | 33.3 | 35 |
| Cmpd 13 | 36 | 17 | 8.3 | 4 | 17 | 13.6 |
| % Reduction from Day 0 | — | — | 51.1 | 95.6 | 0 | 20 |
| % Reduction from Control | — | — | 39.4 | 69.9 | 19 | 32 |
| Cmpd 13/ oxfendazole | 36/10 | 13 | 2.7 | 0.67 | 17.6 | 14.3 |
| % Reduction from Day 0 | — | — | 79.2 | 94.8 | −35.3 | −10 |
| % Reduction from Control | — | — | 80.3 | 94.9 | 10 | 28.5 |

TEST 35

Test against multiple parasites in sheep 1,5-Bis(4-(trifluoromethyl)phenyl)-3-formazancarbonitrile was evaluated for the control of *Haemonchus contortus*, Ostertagia spp., *Trichostrongylus colubriformis* and others in sheep. The compound was administered daily for six continuous days, as an oral drench. The formulation employed was an aqueous suspension. The control sheep were dosed daily with 10 ml of an aqueous suspension (vehicle lacking formazan).

The tapeworm population was reduced by 50% and the *Nematodirus spathiger* population was reduced 72.3%. Results of other parasites were as set forth in the following tables.

TABLE 30A

*Haemonchus contortus* Worm Eggs Per Gram of Feces in Sheep Treated by Single Oral Drench of 2.5 mg/kg Bodyweight for Six Days Using Compound 6 in Aqueous Suspension

| Treatment | Dose mg/kg | Worm Eggs Per Gram of Feces | | | | | | | % Worm Egg Reduction | Total Worm Counts[1] |
|---|---|---|---|---|---|---|---|---|---|---|
| | | Pre | 1 | 2 | 3 | 4 | 5–8* | 12 | | |
| Cmpd 6 | 2.5 × 6 | 11550 | 13200 | 700 | 0 | 0 | 0 | — | 100 | 0 |
| | 2.5 × 6 | 8100 | 7100 | 200 | 0 | 0 | 0 | — | 100 | 0 |
| | 2.6 × 6 | 15900 | 14500 | 1600 | 0 | 0 | 0 | — | 100 | 0 |
| | 2.5 × 6 | 10700 | 10700 | 1000 | 0 | 0 | 0 | — | 100 | 0 |
| | 2.5 × 6 | 7800 | 8100 | 0 | 0 | 0 | 0 | — | 100 | 0 |
| | 2.5 × 6 | 3050 | 3100 | 0 | 0 | 0 | 0 | — | 100 | 0 |
| | | | | | | | | | Avg 100 | Avg 0 |
| VC | 0 | 4850 | 5300 | 4100 | 3900 | 4300 | 4325 | — | 0 | 4155 |
| | 0 | 11800 | 9400 | 8400 | 7700 | 7800 | 7325 | — | 38 | 3782 |
| | 0 | 11400 | 11600 | 9700 | 8700 | 7600 | 7825 | — | 31 | 3172 |
| | 0 | 2800 | 2300 | 4700 | 4200 | 4100 | 4450 | — | 0 | 2145 |
| | | | | | | | | | Avg 17.25 | Avg 3313.5 |

*Average of 4 days sampling
[1]At necropsy 6 days following treatment

TABLE 30B

Trichostrongyle Worm Eggs Per Gram of Feces in Sheep Treated by Single Oral Drench of 2.5 mg/kg Bodyweight for Six Days Using Compound 6 in Aqueous Suspension

| Treatment | Dose mg/kg | Worm Eggs Per Gram of Feces | | | | | | | % Worm Egg Reduction | Total Worm Counts[1] |
|---|---|---|---|---|---|---|---|---|---|---|
| | | Pre | 1 | 2 | 3 | 4 | 5–8* | 12 | | |
| Cmpd 6 | 2.5 × 6 | 1750 | 1600 | 1400 | 700 | 600 | 300 | — | 83 | 218 |
| | 2.5 × 6 | 1000 | 900 | 600 | 1000 | 500 | 400 | — | 60 | 211 |
| | 2.5 × 6 | 1850 | 1600 | 1400 | 1900 | 1100 | 900 | — | 51 | 348 |
| | 2.5 × 6 | 1150 | 1300 | 1500 | 1400 | 1300 | 950 | — | 17 | 305 |
| | 2.5 × 6 | 850 | 1000 | 600 | 500 | 500 | 300 | — | 65 | 58 |
| | 2.5 × 6 | 650 | 500 | 200 | 400 | 400 | 300 | — | 54 | 71 |
| | | | | | | | | | Avg 55 | Avg 201.8 |

TABLE 30B-continued

Trichostrongyle Worm Eggs Per Gram of Feces in Sheep
Treated by Single Oral Drench of 2.5 mg/kg Bodyweight for Six Days
Using Compound 6 in Aqueous Suspension

| Treatment | Dose mg/kg | Worm Eggs Per Gram of Feces | | | | | | | % Worm Egg Reduction | Total Worm Counts[1] |
|---|---|---|---|---|---|---|---|---|---|---|
| | | Pre | 1 | 2 | 3 | 4 | 5–8* | 12 | | |
| VC | 0 | 450 | 700 | 500 | 600 | 700 | 675 | — | 0 | 466 |
| | 0 | 1100 | 800 | 600 | 600 | 800 | 825 | — | 25 | 113 |
| | 0 | 1150 | 1200 | 1100 | 1400 | 1200 | 1275 | — | 0 | 177 |
| | 0 | 800 | 500 | 900 | 900 | 1000 | 1000 | — | 0 | 281 |
| | | | | | | | | | Avg 6.25 | Avg 259.3 |

*Average of 4 days sampling
[1]At necropsy 6 days following treatment

TABLE 30C

Helminthologic Data Collected from Sheep Treated by Oral Drench
Formulation of 2.5 mg Compound 6 per kg Each Day for Six Days

| Treatment | No. Sheep | Worm Eggs Per Gram | | | | | | Average Worm Counts at Necropsy | | | | | |
|---|---|---|---|---|---|---|---|---|---|---|---|---|---|
| | | Haemonchus | | | Trichostrongyles | | | Abomasum | | | | Sm. Intestine | |
| | | Pre | 7 Days | % Red | Pre | 7 Days | % Red | HC | % Red | Ost | % Red | Tr | % Red |
| Cmpd 6 | 6 | 9517 | 0 | 100 | 1100 | 525 | 52.3 | 0 | 100 | 137 | 8.6 | 201.8 | 22.2 |
| VC | 4 | 5056 | 5981 | 0 | 875 | 944 | 0 | 3314 | — | 150 | — | 259.3 | — |

HC = Haemonchus
Ost = Ostertagia
Tr = Trichostrongylus
Red = Reduction

TEST 36

Test against multiple parasites in sheep

Compounds 6, 8, and 13 were evaluated in sheep for the control of multiple parasites: *Haemonchus contortus*, *Trichostrongylus colubriformis*, *Ostertagia spp.*, and *Monezia expensa* (tape worm). There were four animals per treatment group. Administration was by oral gavage of an aqueous suspension of the respective compound. Compound dosing was at amounts equivalent to 5 mg/kg of the parent compound, Compound 6. The test was continued for ten days, at which time the animals were euthanized and internal worm counts made.

Activity was determined by egg count per gram of feces, in vitro assay of serum samples, and worm counts in the abomasum and small intestine at necropsy. Results were as set forth in the following tables.

TABLE 31A

Haemonchus contortus Worm Eggs Per Gram of Feces in Sheep
Treated by an Oral Gavage of Compound 6 and Salts in Aqueous Suspension

| Rx No. | Treatment | Dose mg/kg | Worm Eggs Per Gram of Feces | | | | | | % Worm Egg Reduction | Total Worm Counts[1] | % Worm Reduction |
|---|---|---|---|---|---|---|---|---|---|---|---|
| | | | Pre* | 1 | 2 | 3 | 4 | 5–7* | | | |
| 1 | Cmpd 6 | 5 | 633 | 800 | 0 | 0 | 0 | 0 | 100 | 0 | 100 |
| | | 5 | 1000 | 1300 | 0 | 0 | 0 | 0 | 100 | 0 | 100 |
| | | 5 | 1600 | 800 | 100 | 0 | 0 | 0 | 100 | 0 | 100 |
| | | 5 | 3833 | 2700 | 0 | 0 | 0 | 0 | 100 | 0 | 100 |
| 2 | Cmpd 8 | 6 | 733 | 200 | 0 | 0 | 0 | 0 | 100 | 13** | 97.6 |
| | | 6 | 400 | 0 | 0 | 0 | 0 | 0 | 100 | 0 | 100 |
| | | 6 | 1767 | 1000 | 100 | 0 | 0 | 0 | 100 | 0 | 100 |
| | | 6 | 0 | 0 | 0 | 0 | 0 | 0 | — | 0 | — |
| 3 | Cmpd 13 | 9 | 0 | 0 | 0 | 0 | 0 | 0 | 0 | — | — |
| | | 9 | 1200 | 300 | 0 | 0 | 0 | 0 | 100 | 18 | 96.6* |
| | | 9 | 700 | 100 | 0 | 0 | 0 | 0 | 100 | 0 | 100 |
| | | 9 | 3067 | 900 | 300 | 0 | 0 | 0 | 100 | 0 | 100 |
| 4 | VC | 0 | 1867 | 1900 | 2600 | 2800 | 2400 | 2400 | 0 | 441 | — |
| | VC | 0 | 1500 | 3100 | 2400 | 2200 | 2300 | 2300 | 0 | 626 | — |

*Average of 2 days sampling
[1]At necropsy 7 days following treatment
**very small immature

TABLE 31B

Trichostrongyle Worm Eggs Per Gram of Feces in Sheep
Treated by an Oral Gavage of Compound 6 and Salts in Aqueous Suspension

| Rx No. | Treatment | Dose mg/kg | Worm Eggs Per Gram of Feces | | | | | | % Worm Egg Reduction |
|---|---|---|---|---|---|---|---|---|---|
| | | | Pre* | 1 | 2 | 3 | 4 | 5–7* | |
| 1 | Cmpd 6 | 5 | 300 | 500 | 100 | 0 | 0 | 200 | 33 |
| | | 5 | 867 | 900 | 400 | 600 | 500 | 450 | 48 |
| | | 5 | 0 | 0 | 0 | 0 | 0 | 0 | — |
| | | 5 | 2300 | 900 | 800 | 900 | 700 | 700 | 70 |

TABLE 31B-continued

Trichostrongyle Worm Eggs Per Gram of Feces in Sheep
Treated by an Oral Gavage of Compound 6 and Salts in Aqueous Suspension

| Rx No. | Treatment | Dose mg/kg | Worm Eggs Per Gram of Feces | | | | | | % Worm Egg Reduction |
|---|---|---|---|---|---|---|---|---|---|
| | | | Pre* | 1 | 2 | 3 | 4 | 5-7* | |
| 2 | Cmpd 8 | 6 | 367 | 200 | 200 | 300 | 100 | 300 | 19 |
| | | 6 | 200 | 300 | 700 | 200 | 300 | 300 | 0 |
| | | 6 | 1167 | 700 | 300 | 300 | 200 | 150 | 87 |
| | | 6 | 500 | 800 | 400 | 300 | 500 | 450 | 10 |
| 3 | Cmpd 13 | 9 | 300 | 300 | 200 | 200 | 100 | 100 | 67 |
| | | 9 | 667 | 100 | 0 | 0 | 0 | 150 | 78 |
| | | 9 | 0 | 0 | 0 | 0 | 0 | 0 | — |
| | | 9 | 833 | 400 | 300 | 100 | 400 | 650 | 22 |
| 4 | VC | 0 | 833 | 600 | 900 | 700 | 600 | 800 | 4 |
| | VC | 0 | 433 | 1300 | 900 | 800 | 700 | 650 | 0 |

*Average of 2 days sampling

TABLE 31C

Summary and Necropsy Data - Helminthologic Data Collected from Sheep Treated
With Oral Drench Formulations of Compound 6 and Salts in Aqueous Suspension

| Treatment | No. Sheep | Worm Eggs Per Gram | | | | | | Average Worm Counts at Necropsy | | | | | |
|---|---|---|---|---|---|---|---|---|---|---|---|---|---|
| | | Haemonchus | | | Trichostrongyles | | | Abomasum | | | | Sm. Intestine | |
| | | Pre | 7 Days | % Red | Pre | 7 Days | % Red | HC | % Red | Ost | % Red | Tr | % Red |
| Cmpd 6 | 4 | 1767 | 0 | 100 | 1156 | 450 | 61 | 0 | 100 | 101 | 73 | 21 | 89 |
| Cmpd 8 | 3 | 967 | 0 | 100 | 559 | 300 | 46 | 4.3* | 99.2 | 80 | 79 | 42 | 79 |
| Cmpd 13 | 3 | 1656 | 0 | 100 | 600 | 300 | 50 | 6* | 99 | 47 | 87 | 86 | 57 |
| VC | 2 | 1684 | 2350 | 0 | 633 | 725 | 0 | 534 | — | 373 | — | 198 | — |

*immature stages
HC = Haemonchus
Ost = Ostertagia
Tr = Trichostrongylus
Red = Reduction

TABLE 31D

Percent Insecticidal Activity Against *Phormia regina* Following 24 hr in vitro Exposure

| Treatment | Dose mg/kg | Pre | 1 HR | 4 HR | 8 HR | 12 HR | 24 HR | 36 HR | Day 2 | Day 3 | Day 4 | Day 5 |
|---|---|---|---|---|---|---|---|---|---|---|---|---|
| Cmpd 6 | 5.0 | 0 | 0 | 100 | 100 | 100 | 100 | 0 | 0 | 0 | 0 | 0 |
| | 5.0 | 0 | 0 | 100 | 100 | 100 | 100 | 100 | 0 | 0 | 0 | 0 |
| | 5.0 | 0 | 100 | 100 | 100 | 100 | 100 | 100 | 0 | 0 | 0 | 0 |
| | 5.0 | 0 | 0 | 100 | 100 | 100 | 100 | 80 | 0 | 0 | 0 | 0 |
| Cmpd 8 | 6.0 | 0 | 0 | 100 | 100 | 100 | 100 | 100 | 0 | 0 | 0 | 0 |
| | 6.0 | 0 | 100 | 100 | 100 | 100 | 100 | 100 | 0 | 0 | 0 | 0 |
| | 6.0 | 0 | 100 | 100 | 100 | 100 | 100 | 100 | 0 | 0 | 0 | 0 |
| | 6.0 | 0 | 100 | 100 | 100 | 100 | 100 | 100 | 10 | 0 | 0 | 0 |
| Cmpd 13 | 9.0 | 0 | 0 | 100 | 100 | 100 | 100 | 100 | 100 | 0 | 0 | 0 |
| | 9.0 | 0 | 0 | 100 | 100 | 100 | 100 | 100 | 100 | 0 | 0 | 0 |
| | 9.0 | 0 | 100 | 100 | 100 | 100 | 100 | 100 | 100 | 0 | 0 | 0 |
| | 9.0 | 0 | 100 | 100 | 100 | 100 | 100 | 100 | 0 | 0 | 0 | 0 |
| VC | 0 | 0 | 0 | 0 | 0 | 0 | 0 | 0 | 0 | 0 | 0 | 0 |
| VC | 0 | 0 | 0 | 0 | 0 | 0 | 0 | 0 | 0 | 0 | 0 | 0 |

TABLE 31E

Percent Insecticidal Activity Against *Phormia regina* Following 48 hr in vitro Exposure

| Treatment | Dose mg/kg | Pre | 1 HR | 4 HR | 8 HR | 12 HR | 24 HR | 36 HR | Day 2 | Day 3 | Day 4 | Day 5 |
|---|---|---|---|---|---|---|---|---|---|---|---|---|
| Cmpd 6 | 5.0 | 0 | 0 | 100 | 100 | 100 | 100 | 50 | 0 | 0 | 0 | 0 |
| | 5.0 | 0 | 0 | 100 | 100 | 100 | 100 | 100 | 0 | 0 | 0 | 0 |
| | 5.0 | 0 | 100 | 100 | 100 | 100 | 100 | 100 | 0 | 0 | 0 | 0 |
| | 5.0 | 0 | 0 | 100 | 100 | 100 | 100 | 95 | 0 | 0 | 0 | 0 |
| Cmpd 8 | 6.0 | 0 | 0 | 100 | 100 | 100 | 100 | 100 | 0 | 0 | 0 | 0 |
| | 6.0 | 0 | 100 | 100 | 100 | 100 | 100 | 100 | 0 | 0 | 0 | 0 |
| | 6.0 | 0 | 100 | 100 | 100 | 100 | 100 | 100 | 0 | 0 | 0 | 0 |
| | 6.0 | 0 | 100 | 100 | 100 | 100 | 100 | 100 | 90 | 0 | 0 | 0 |
| Cmpd 13 | 9.0 | 0 | 0 | 100 | 100 | 100 | 100 | 100 | 100 | 0 | 0 | 0 |
| | 9.0 | 0 | 0 | 100 | 100 | 100 | 100 | 100 | 100 | 40 | 0 | 0 |
| | 9.0 | 0 | 100 | 100 | 100 | 100 | 100 | 100 | 100 | 80 | 0 | 0 |
| | 9.0 | 0 | 100 | 100 | 100 | 100 | 100 | 100 | 0 | 0 | 0 | 0 |
| VC | 0 | 0 | 0 | 0 | 0 | 0 | 0 | 0 | 0 | 0 | 0 | 0 |
| VC | 0 | 0 | 0 | 0 | 0 | 0 | 0 | 0 | 0 | 0 | 0 | 0 |

In addition, activity was noted against tapeworms. Tapeworms were completely eliminated from two

I claim:

1. A method for protecting a vertebrate animal against a blood-ingesting parasite or a non-blood-ingesting intestinal parasite which comprises administering to the animal an effective amount of an active agent which is a compound of the formula:

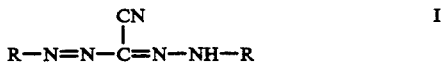

wherein each R independently represents a moiety of the formula:

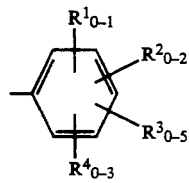

wherein
R$^1$ is cyano;
R$^2$ is nitro;
R$^3$ is bromo, chloro, or fluoro;
R$^4$ is iodo or a group of the formula —R$^5{}_n$R$^6$ wherein n represents 0 or 1,
R$^5$ represents
—O—,
—S—,
—SO—,
—SO$_2$, or
—OSO$_2$—, and
R$^6$ represents
—CF$_3$,
—CF$_2$CF$_2$H,
—CH$_2$CF$_3$, or
—C$_2$F$_5$;
with the following limitations:
(1) at least one R bears at least one substituent,
(2) when an R contains one or more R$^1$, R$^2$, or R$^4$ substituents, the total number of substituents on that R is not more than 3; or a physiologically acceptable salt thereof.

2. The method of Claim 1 for protecting a vertebrate animal against a blood-ingesting parasite.

3. The method of Claim 2 wherein the active agent is 1,5-bis(4-(trifluoromethyl)phenyl)-3-formazancarbonitrile or a physiologically acceptable salt thereof.

4. The method of Claim 3 wherein the active agent is 1,5-bis(4-(trifluoromethyl)phenyl)-3-formazancarbonitrile.

5. The method of Claim 3 wherein the active agent is the levamisole salt of 1,5-bis(4-(trifluoromethyl)-phenyl)-3-formazancarbonitrile.

6. The method of Claim 3 wherein the active agent is a quaternary ammonium salt of 1,5-bis(4-(trifluoromethyl)phenyl)-3-formazancarbonitrile of the formula:

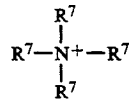

wherein each R$^7$ is independently selected from the group consisting of alkyl of from 1 to 20 carbon atoms, with the total number of carbon atoms in all of the R$^7$ groups being from 4 to 40.

7. The method of Claim 6 wherein the active agent is 1,5-bis(4-(trifluoromethyl)phenyl)-3-formazancarbonitrile tetramethylammonium salt.

8. The method of Claim 6 wherein the active agent is 1,5-bis(4-(trifluoromethyl)phenyl)-3-formazancarbonitrile tetraethylammonium salt.

9. The method of Claim 6 wherein the active agent is 1,5-bis(4-(trifluoromethyl)phenyl)-3-formazancarbonitrile tetra-n-propylammonium salt.

10. The method of claim 6 wherein the active agent is 1,5-bis(4-(trifluoromethyl)phenyl)-3-formazancarbonitrile tetra-n-butylammonium salt.

11. The method of claim 6 wherein the active agent is 1,5-bis(4-(trifluoromethyl)phenyl)-3-formazancarbonitrile trimethyloctadecylammonium salt.

12. The method of claim 2 wherein the vertebrate animal is a fish.

13. The method of claim 12 wherein the active agent is 1,5-bis(4-(trifluoromethyl)phenyl)-3-formazancarbonitrile or a physiologically acceptable salt thereof.

14. The method of claim 2 wherein the vertebrate animal is a bird.

15. The method of claim 14 wherein the active agent is 1,5-bis(4-(trifluoromethyl)phenyl)-3-formazancarbonitrile or a physiologically acceptable salt thereof.

16. The method of claim 2 wherein the vertebrate animal is a mammal.

17. The method of claim 16 wherein the active agent is 1,5-bis(4-(trifluoromethyl)phenyl)-3-formazancarbonitrile or a physiologically acceptable salt thereof.

18. The method of claim 16 wherein the mammal is a cow.

19. The method of claim 18 where the blood ingesting parasite is an Ostertagia species.

20. The method of claim 19 wherein the active agent is 1,5-bis(4-(trifluoromethyl)phenyl)-3-formazancarbonitrile or a physiologically acceptable salt thereof.

21. The method of claim 16 wherein the mammal is a sheep.

22. The method of claim 21 wherein the blood ingesting parasite is a Haemonchus species.

23. The method of claim 22 wherein the active agent is 1,5-bis(4-(trifluoromethyl)phenyl)-3-formazancarbonitrile or a physiologically acceptable salt thereof.

24. The method of claim 22 wherein the Haemonchus species is an ivermectin-resistant Haemonchus species.

25. The method of claim 24 wherein the active agent is 1,5-bis(4-(trifluoromethyl)phenyl)-3-formazancarbonitrile or a physiologically acceptable salt thereof.

26. The method of claim 16 wherein the vertebrate animal is a cat or dog.

27. The method of claim 26 wherein the blood ingesting parasite is a flea or tick.

28. The method of claim 27 wherein the active agent is 1,5-bis(4-(trifluoromethyl)phenyl)-3-formazancarbonitrile or a physiologically acceptable salt thereof.

29. The method of claim 1 for protecting a vertebrate animal against a non-blood-ingesting intestinal parasite.

30. The method of claim 29 wherein the active agent is 1,5-bis(4-(trifluoromethyl)phenyl)-3-formazancarbonitrile or a physiologically acceptable salt thereof.

31. A method for inhibiting the growth of parasitic organisms in feces of a warm blooded animal which comprises administering to the animal an effective amount of an active agent which is a compound of the formula:

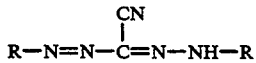

wherein each R independently represents a moiety of the formula:

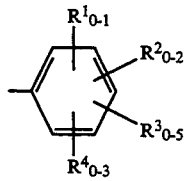

wherein
R$^1$ is cyano;
R$^2$ is nitro;
R$^3$ is bromo, chloro, or fluoro;
R$^4$ is iodo or a group of the formula —R$^5_n$R$^6$ wherein n represents 0 or 1,
R$^5$ represents
—O—,
—S—,
—SO—,
—SO$_2$, or
—OSO$_2$—, and
R$^6$ represents
—CF$_3$,
—CF$_2$CF$_2$H,
—CH$_2$CF$_3$, or
—C$_2$F$_5$;
with the following limitations:
(1) at least one R bears at least one substituent,
(2) when an R contains one or more R$^1$, R$^2$, or R$^4$ substituents, the total number of substituents on that R is not more than 3; or a physiologically acceptable salt thereof.

32. The method of claim 31 wherein the active agent is 1,5-bis(4-(trifluromethyl)phenyl)-3-formazancarbonitrile or a physiologically acceptable salt thereof.

33. A method for protecting a vertebrate animal against a parasite which comprises administering to the animal both a first active agent which is a compound of the formula:

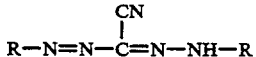

wherein each R independently represents a moiety of the formula:

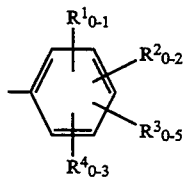

wherein
R$^1$ is cyano;
R$^2$ is nitro;
R$^3$ is bromo, chloro, or fluoro;
R$^4$ is iodo or a group of the formula —R$^5_n$R$^6$ wherein n represents 0 or 1,
R$^5$ represents
—O—,
—S—,
—SO—,
—SO$_2$, or
—OSO$_2$—, and
R$^6$ represents
—CF$_3$,
—CF$_2$CF$_2$H,
—CH$_2$CF$_3$, or
—C$_2$F$_5$;
with the following limitations:
(1) at least one R bears at least one substituent,
(2) when an R contains one or more R$^1$, R$^2$, or R$^4$ substituents, the total number of substituents on that R is not more than 3; or a physiologically acceptable salt thereof; as well as a second active agent, which is a compound selected from the group consisting of
albendazole,
fenbendazole,
flubendazole,
mebendazole,
oxfendazole,
oxibendazole,
ricobendazole,
thiabendazole,
triclavendazole,
levamisole,
morantel,
pyrantel, and
piperazine; said first and second active agents being administered in amounts which together are effective to control the parasite.

34. The method of claim 33 wherein the first active agent is 1,5-bis(4-(trifluoromethyl)phenyl)-3-formazancarbonitrile or a physiologically acceptable salt thereof.

35. The method of claim 34 wherein the second active agent is oxfendazole.

36. The method of claim 34 wherein the second active agent is levamisole.

37. A compound of the formula:

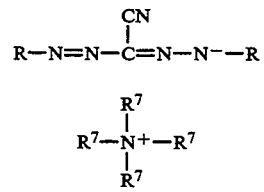

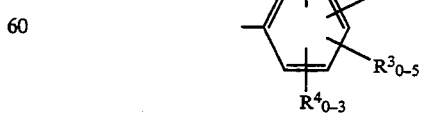

wherein each R independently represents a moiety of the formula:

wherein
R$^1$ is cyano;
R$^2$ is nitro;
R$^3$ is bromo, chloro, or fluoro;

$R^4$ is iodo or a group of the formula $-R^{5a}{}_nR^6$ wherein n represents 0 or 1, $R^{5a}$ represents
—O—,
—S—,
—SO—, or
—SO$_2$, and $R^6$ represents
—CF$_3$,
—CF$_2$CF$_2$H,
—CH$_2$CF$_3$, or
—C$_2$F$_5$;

with the following limitations:
(1) at least one R bears at least one substituent,
(2) when an R contains one or more $R^1$, $R^2$, or $R^4$ substituents, the total number of substituents on that R is not more than 3; and each $R^7$ is independently selected from the group consisting of alkyl of from 1 to 20 carbon atoms, with the total number of carbon atoms in all of the $R^7$ groups being from 4 to 40.

38. A compound of claim 37 which is any

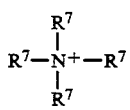

salt of 1,5-bis(4-(trifluoromethyl)phenyl)-3-formazancarbonitrile.

39. The compound of claim 38 which is 1,5-bis(4-(trifluoromethyl)phenyl)-3-formazancarbonitrile tetramethylammonium salt.

40. The compound of claim 38 which is 1,5-bis(4-(trifluoromethyl)phenyl)-3-formazancarbonitrile tetraethylammonium salt.

41. The compound of claim 38 which is 1,5-bis(4-(trifluoromethyl)phenyl)-3-formazancarbonitrile tetra-n-propylammonium salt.

42. The compound of claim 38 which is 1,5-bis(4-(trifluoromethyl)phenyl)-3-formazancarbonitrile tetra-n-butylammonium salt.

43. The compound of claim 38 which is 1,5-bis(4-(trifluoromethyl)phenyl)-3-formazancarbonitrile tetra-n-pentylammonium salt.

44. The compound of claim 38 which is 1,5-bis(4-(trifluoromethyl)phenyl)-3-formazancarbonitrile trimethyloctadecylammonium salt.

45. A compound of the formula:

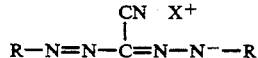

wherein each R independently represents a moiety of the formula:

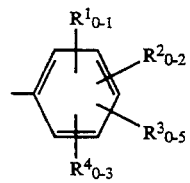

wherein
$R^1$ is cyano;
$R^2$ is nitro;
$R^3$ is bromo, chloro, or fluoro;
$R^4$ is iodo or a group of the formula $-R^5{}_nR^6$ wherein n represents 0 or 1, $R^5$ represents
—O—,
—S—,
—SO—,
—SO$_2$, or
—OSO$_2$—, and $R^6$ represents
—CF$_3$,
—CF$_2$CF$_2$H,
—CH$_2$CF$_3$, or
—C$_2$F$_5$;

with the following limitations:
(1) at least one R bears at least one substituent,
(2) when an R contains one or more $R^1$, $R^2$, or $R^4$ substituents, the total number of substituents on that R is not more than 3; and wherein X$^+$ is a cation of levamisole, morantel, pyrantel, or piperazine.

46. The compound of Claim 45 wherein

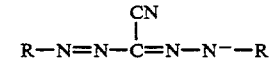

is the anion from 1,5-bis(4-(trifluoromethyl)phenyl)-3-formazancarbonitrile.

47. The compound of Claim 46 wherein X$^+$ is a cation from levamisole.

48. A compound of the formula

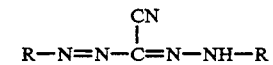

wherein each R independently represents a moiety of the formula:

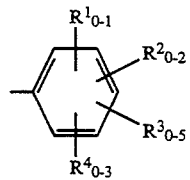

wherein
$R^1$ is cyano;
$R^2$ is nitro;
$R^3$ is bromo, chloro, or fluoro;
$R^4$ is iodo or a group of the formula $-R^5{}_nR^6$ wherein n represents 0 or 1, $R^5$ represents
—O—,
—S—,
—SO—,
—SO$_2$, or
—OSO$_2$—, and $R^6$ represents
—CF$_3$,
—CF$_2$CF$_2$H,
—CH$_2$CF$_3$, or
—C$_2$F$_5$;

with the following limitations:

(1) at least one R bears at least one substituent which is —$R^5{}_nR^6$ wherein n is 1 and $R^5$ is —$OSO_2$—;

(2) when an R contains one or more $R^1$, $R^2$, or $R^4$ substituents, the total number of substituents on that R is not more than 3; or a physiologically acceptable salt thereof.

49. The compound of Claim 48 which is 1,5-bis(4-(trifluoromethylsulfonyloxy)phenyl)-3-formazancarbonitrile or a physiologically acceptable salt thereof.

* * * * *